United States Patent
Kim et al.

(10) Patent No.: US 12,225,814 B2
(45) Date of Patent: Feb. 11, 2025

(54) COMPOUND FOR ORGANIC OPTOELECTRONIC DIODE, COMPOSITION FOR ORGANIC OPTOELECTRONIC DIODE, ORGANIC OPTOELECTRONIC DIODE AND DISPLAY DEVICE

(71) Applicant: SAMSUNG SDI CO., LTD., Yongin-si (KR)

(72) Inventors: Changwoo Kim, Suwon-si (KR); Seungjae Lee, Suwon-si (KR); Hyung Sun Kim, Suwon-si (KR); Dong Wan Ryu, Suwon-si (KR); Chang Ju Shin, Suwon-si (KR); Kipo Jang, Suwon-si (KR); Sung-Hyun Jung, Suwon-si (KR); Juyeon Jung, Suwon-si (KR); Handong Chu, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 681 days.

(21) Appl. No.: 16/955,128

(22) PCT Filed: Dec. 31, 2018

(86) PCT No.: PCT/KR2018/016993
§ 371 (c)(1),
(2) Date: Jun. 18, 2020

(87) PCT Pub. No.: WO2019/132632
PCT Pub. Date: Jul. 4, 2019

(65) Prior Publication Data
US 2020/0388766 A1   Dec. 10, 2020

(30) Foreign Application Priority Data

Dec. 29, 2017   (KR) .................. 10-2017-0184865
Dec. 31, 2018   (KR) .................. 10-2018-0173877

(51) Int. Cl.
C07D 405/14   (2006.01)
C09K 11/06   (2006.01)
(Continued)

(52) U.S. Cl.
CPC ......... H10K 85/654 (2023.02); *C07D 405/14* (2013.01); *C09K 11/06* (2013.01);
(Continued)

(58) Field of Classification Search
CPC ............. H01L 51/0064; H01L 51/0067; H01L 51/0073; H01L 51/0074; H01L 51/0085;
(Continued)

(56) References Cited

U.S. PATENT DOCUMENTS

2016/0028021 A1   1/2016   Zeng et al.
2018/0301639 A1*  10/2018  Zeng .................. C07D 487/04

FOREIGN PATENT DOCUMENTS

CN   106471093 A   3/2017
CN   106883220 A   6/2017
(Continued)

OTHER PUBLICATIONS

International Search Report dated May 4, 2019 for PCT/KR2018/016993.
(Continued)

*Primary Examiner* — Jennifer A Boyd
*Assistant Examiner* — Rachel Simbana
(74) *Attorney, Agent, or Firm* — Lee IP Law, P.C.

(57) ABSTRACT

Provided are: a compound for an organic optoelectronic diode; a composition for an organic optoelectronic diode including the same; an organic optoelectronic diode including the composition for the organic optoelectronic diode as a host; and a display device including the organic optoelectronic diode.

14 Claims, 1 Drawing Sheet

(51) Int. Cl.
    *H10K 50/11*     (2023.01)
    *H10K 50/12*     (2023.01)
    *H10K 59/00*     (2023.01)
    *H10K 85/30*     (2023.01)
    *H10K 85/60*     (2023.01)
    *H10K 101/00*    (2023.01)
    *H10K 101/10*    (2023.01)

(52) U.S. Cl.
    CPC ....... *H10K 85/342* (2023.02); *H10K 85/6574* (2023.02); *C09K 2211/1029* (2013.01); *C09K 2211/1033* (2013.01); *C09K 2211/185* (2013.01); *H10K 50/11* (2023.02); *H10K 2101/10* (2023.02)

(58) Field of Classification Search
    CPC ............. H01L 51/5016; H01L 51/0072; H01L 2251/5384; H01L 27/32; H01L 51/5024; C07D 405/14; C09K 11/06; C09K 2211/1029; C09K 2211/1033; C09K 2211/185; C09K 2211/1059; C09K 2211/1088; H10K 85/652; H10K 85/654; H10K 85/6574
    See application file for complete search history.

(56) References Cited

FOREIGN PATENT DOCUMENTS

| | | | |
|---|---|---|---|
| CN | 108368078 A | 8/2018 | |
| CN | 111315740 A | 6/2020 | |
| KR | 10-2016-0018433 A | 2/2016 | |
| KR | 10-2017-0037276 A | 4/2017 | |
| KR | 10-2017-0089599 A | 8/2017 | |
| KR | 10-2017-0122023 A | 11/2017 | |
| KR | 10-2018-0010130 A | 1/2018 | |
| TW | 201811773 A | 4/2018 | |
| TW | 201920102 A | 6/2019 | |
| WO | WO-2012087955 A1 * | 6/2012 | ........... C09K 11/025 |
| WO | WO 2017/171420 A1 | 5/2017 | |

OTHER PUBLICATIONS

Chinese Office action and Search Report dated Jan. 20, 2023.
Chinese Office Action (including a search report) dated Sep. 1, 2023, of the corresponding Chinese Patent Application No. 201880084026.5.

* cited by examiner

[Figure 1]
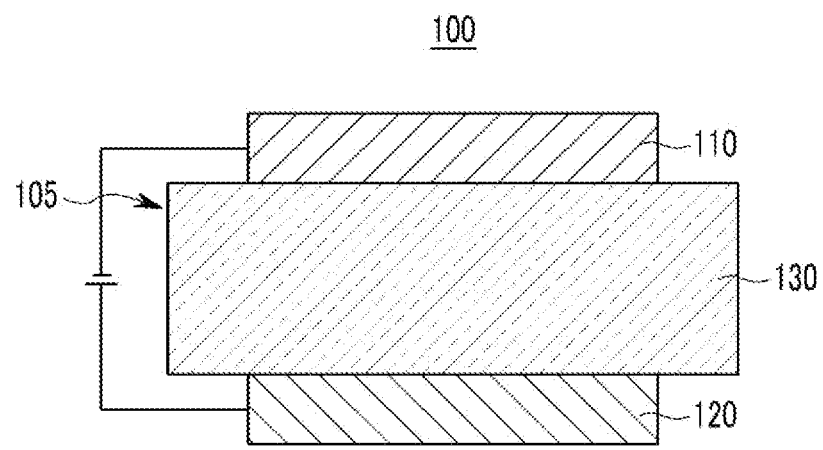
[Figure 2]
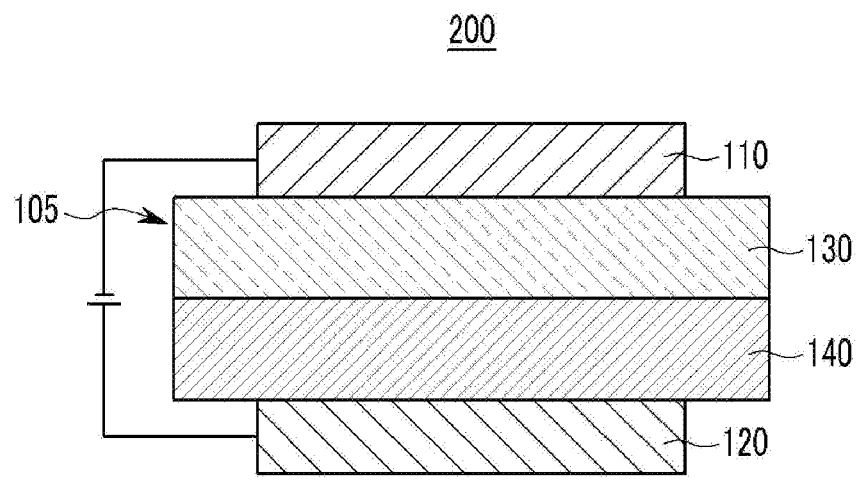

COMPOUND FOR ORGANIC OPTOELECTRONIC DIODE, COMPOSITION FOR ORGANIC OPTOELECTRONIC DIODE, ORGANIC OPTOELECTRONIC DIODE AND DISPLAY DEVICE

CROSS REFERENCE TO RELATED APPLICATIONS

This is the U.S. national phase application based on PCT Application No. PCT/KR2018/016993, filed Dec. 31, 2018, which is based on Korean Patent Application No. 10-2017-0184865, filed Dec. 29, 2017, and Korean Patent Application No. 10-2018-0173877, filed Dec. 31, 2018, the entire contents of all of which are hereby incorporated by reference.

TECHNICAL FIELD

A compound for an organic optoelectronic diode, a composition for an organic optoelectronic diode including the same, an organic optoelectronic diode including the composition for the organic optoelectronic diode as a host, and a display device including the organic optoelectronic diode are related.

BACKGROUND ART

An organic optoelectronic diode is a device that converts electrical energy into photoenergy, and vice versa.

An organic optoelectronic diode may be classified as follows in accordance with its driving principles. One is a photoelectric diode where excitons are generated by photoenergy, separated into electrons and holes, and are transferred to different electrodes to generate electrical energy, and the other is a light emitting diode where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may include at least one layer selected from, for example a hole injection layer, a hole transport layer, an electron blocking layer, an electron transport layer, an electron injection layer, and a hole blocking layer in order to improve efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic diode capable of realizing an organic optoelectronic diode having low driving and high efficiency.

Another embodiment provides a composition for an organic optoelectronic diode including the compound for the organic optoelectronic diode.

Another embodiment provides an organic optoelectronic diode including the composition for an organic optoelectronic diode.

Another embodiment provides a display device including the organic optoelectronic diode.

Technical Solution

According to one embodiment, a compound for an organic optoelectronic diode represented by Chemical Formula 1 is provided.

[Chemical Formula 1]

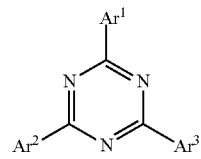

In Chemical Formula 1, $Ar^1$ is a substituted or unsubstituted C6 to C20 aryl group, $Ar^2$ is represented by one of Chemical Formula 2A, Chemical Formula 3A, and Chemical Formula 4A, and $Ar^3$ is represented by one of Chemical Formula 2B, Chemical Formula 3B, and Chemical Formula 4B,

[Chemical Formula 2A]

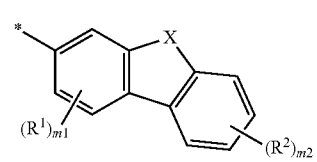

[Chemical Formula 3A]

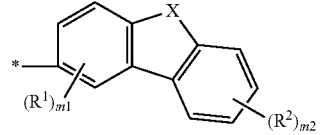

[Chemical Formula 4A]

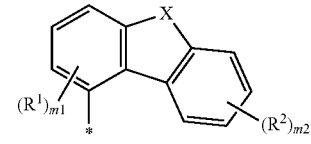

[Chemical Formula 2B]

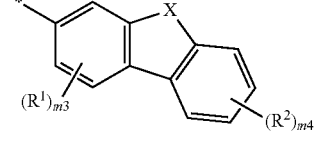

-continued

[Chemical Formula 3B]

$(R^1)_{m3}$ ... $(R^2)_{m4}$

[Chemical Formula 4B]

$(R^1)_{m3}$ ... $(R^2)_{m4}$

In Chemical Formula 2A, Chemical Formula 3A, Chemical Formula 4A, Chemical Formula 2B, Chemical Formula 3B, and Chemical Formula 4B, X is O or S, $R^1$ and $R^2$ are independently a substituted or unsubstituted C6 to C20 aryl group, provided that $R^1$ and $R^2$ are not linked to form a fused ring, m1 to m4 are independently an integer of 0 to 3, and m1+m2+m3+m4≠0, and

* is a linking point.

According to another embodiment, a composition for an organic optoelectronic diode including the compound for the organic optoelectronic diode is provided.

According to another embodiment, an organic optoelectronic diode including the composition for the organic optoelectronic diode, as a host is provided.

According to another embodiment, a display device including the organic optoelectronic diode is provided.

Advantageous Effects

A low driving/high efficiency organic optoelectronic diode may be realized.

DESCRIPTION OF THE DRAWINGS

FIGS. 1 and 2 are cross-sectional views showing organic light emitting diodes according to embodiments.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C10 alkyl group, a C6 to C20 aryl group, or a C2 to C20 heterocyclic group. In a specific example of the present invention, the "substituted" refers to replacement of at least one hydrogen by deuterium, a C1 to C4 alkyl group, a C6 to C12 aryl group, or a C2 to C12 heterocyclic group. More specifically, "substituted" refers to replacement of at least one hydrogen of a substituent or a compound by deuterium, a C1 to C5 alkyl group, phenyl group, a biphenyl group, a terphenyl group, a naphthyl group, a benzofuranyl group, a benzothiophenyl group, a dibenzofuranyl group, a dibenzothiophenyl group, or a carbazolyl group. In addition, in the most specific examples of the present invention, "substituted" refers to replacement of at least one hydrogen of a substituent or a compound by deuterium, a methyl group, an ethyl group, a propyl group, a butyl group, a phenyl group, a para-biphenyl group, a meta-biphenyl group, a dibenzofuranyl group, a dibenzothiophenyl group, or a carbazolyl group.

In the present specification when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, or two or more hydrocarbon aromatic moieties are fused directly or indirectly to provide a non-aromatic fused ring. For example, a fluorenyl group may be included.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one hetero atom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one hetero atom selected from N, O, S, P, and Si instead of carbon (C). Two or more heteroaryl groups are linked by a sigma bond directly, or when the C2 to C60 heteroaryl group includes two or more rings, the two or more rings may be fused. When the heteroaryl group is a fused ring, each ring may include 1 to 3 hetero atoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or combination thereof, but is not limited thereto.

In the present specification, hole characteristics refer to an ability to donate an electron to form a hole when an electric field is applied, and that a hole formed in the anode may be easily injected into a light emitting layer, and a hole formed in a light emitting layer may be easily transported into an anode and transported in the light emitting layer due to conductive characteristics according to a highest occupied molecular orbital (HOMO) level.

In addition, electron characteristics refer to an ability to accept an electron when an electric field is applied, and that an electron formed in a cathode may be easily injected into a light emitting layer, and an electron formed in a light emitting layer may be easily transported into a cathode and transported in the light emitting layer due to conductive characteristics according to a lowest unoccupied molecular orbital (LUMO) level.

Hereinafter, a compound for an organic optoelectronic diode is described.

The compound for the organic optoelectronic diode is represented by Chemical Formula 1.

[Chemical Formula 1]

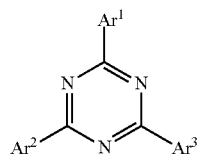

In Chemical Formula 1, $Ar^1$ is a substituted or unsubstituted C6 to C20 aryl group, $Ar^2$ is represented by one of Chemical Formula 2A, Chemical Formula 3A, and Chemical Formula 4A, and $Ar^3$ is represented by one of Chemical Formula 2B, Chemical Formula 3B, and Chemical Formula 4B,

[Chemical Formula 2A]

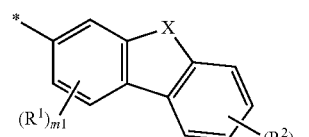

[Chemical Formula 3A]

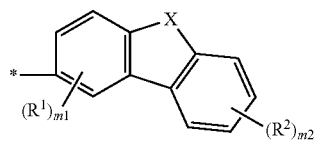

[Chemical Formula 4A]

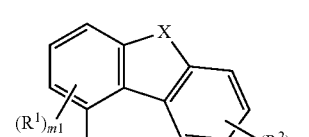

[Chemical Formula 2B]

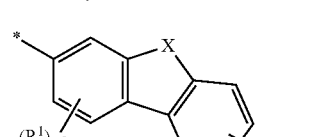

[Chemical Formula 3B]

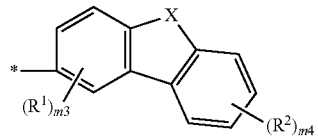

[Chemical Formula 4B]

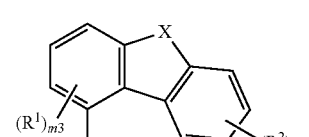

In Chemical Formula 2A, Chemical Formula 3A, Chemical Formula 4A, Chemical Formula 2B, Chemical Formula 3B, and Chemical Formula 4B, X is O or S, $R^1$ and $R^2$ are independently a substituted or unsubstituted C6 to C20 aryl group, provided that $R^1$ and $R^2$ are not linked to form a fused ring, m1 to m4 are independently an integer of 0 to 3, and m1+m2+m3+m4≠0, and \* is a linking point.

The compound for the organic optoelectronic diode according to the present invention has triazine in the center and two dibenzofuran and/or dibenzothiophene rings as substituents, wherein at least one of these two dibenzofuran and/or dibenzothiophene rings necessarily has an aryl group as a substituent, and the aryl group includes no aryl group that is a fused ring. Since the compound having two dibenzofuran and/or dibenzothiophene rings as substituents with triazine in the center and thus has an effect of improving electron mobility, a low driving/high efficiency device may be manufactured. In addition, since at least one of these two dibenzofuran and/or dibenzothiophene rings necessarily has an aryl group as substituents, and the aryl group includes no fused ring aryl group, a material having a low deposition temperature and a high glass transition temperature based on the same molecular weight may be synthesized by finely tuning a deposition temperature and a glass transition temperature. The fused ring may be, for example, an aryl group such as a naphthyl group and the like as an aryl group sharing a carbon-carbon bond.

For example, $Ar^2$ and $Ar^3$ may independently be represented by Chemical Formula 2-1, Chemical Formula 2-2, Chemical Formula 2-3, Chemical Formula 3-1, Chemical Formula 3-2, Chemical Formula 3-3, Chemical Formula 4-1, or Chemical Formula 4-2, provided that $Ar^2$ and $Ar^3$ are not simultaneously represented by Chemical Formula 2-3, $Ar^2$ and $Ar^3$ are not simultaneously represented by Chemical Formula 3-3, and $Ar^2$ and $Ar^3$ are not simultaneously represented by Chemical Formula 4-2.

[Chemical Formula 2-1]

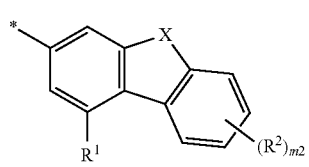

[Chemical Formula 2-2]

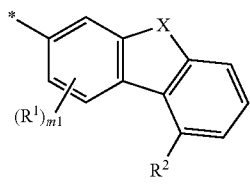

[Chemical Formula 2-3]

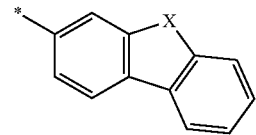

[Chemical Formula 3-1]

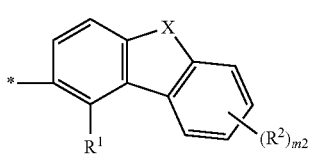

[Chemical Formula 3-2]

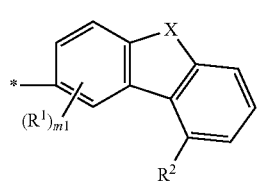

[Chemical Formula 3-3]

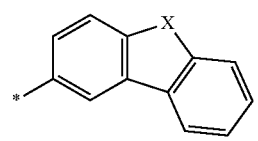

[Chemical Formula 4-1]

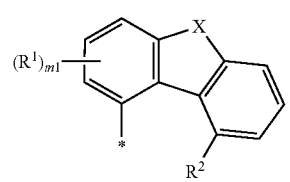

[Chemical Formula 4-2]

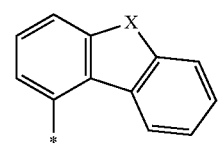

In Chemical Formula 2-1, Chemical Formula 2-2, Chemical Formula 2-3, Chemical Formula 3-1, Chemical Formula 3-2, Chemical Formula 3-3, Chemical Formula 4-1, and Chemical Formula 4-2, X is O or S, $R^1$ and $R^2$ are independently a substituted or unsubstituted C6 to C20 aryl group, provided that $R^1$ and $R^2$ are not linked to form a fused ring, m1 to m4 are independently an integer of 0 to 3, and m1+m2+m3+m4≠0, and \* is a linking point.

For example, m1 and m2 may independently be an integer of 0 or 1.

For example, $R^1$ and $R^2$ may independently be a substituted or unsubstituted phenyl group or a substituted or unsubstituted biphenyl group.

For example, $R^1$ and $R^2$ may independently be selected from the substituents of Group I.

[Group I]

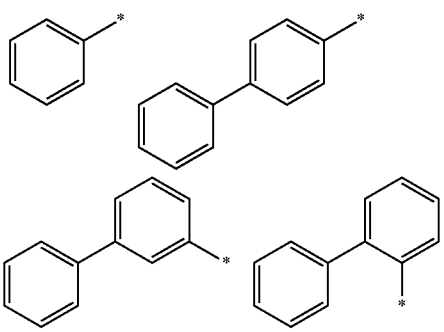

In Group I, * is a linking point.

For example, Ar¹ may be a substituted or unsubstituted phenyl group, a substituted or unsubstituted biphenyl group, a substituted or unsubstituted terphenyl group, or a substituted or unsubstituted naphthyl group.

The compound for the organic optoelectronic diode represented by Chemical Formula 1 may be selected from the compounds of Group 1, but is not limited thereto.

[Group 1]

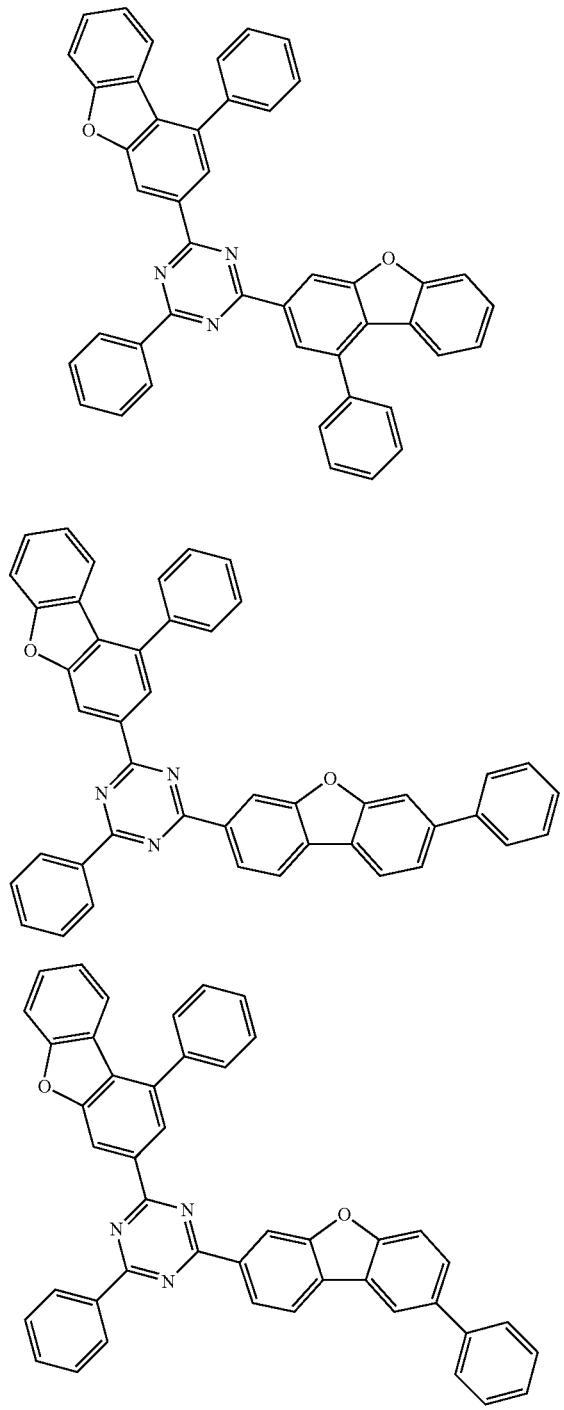

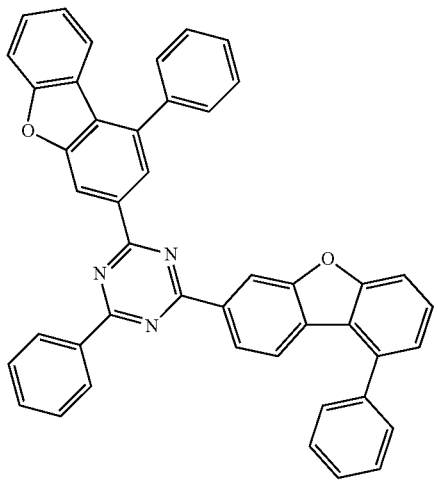

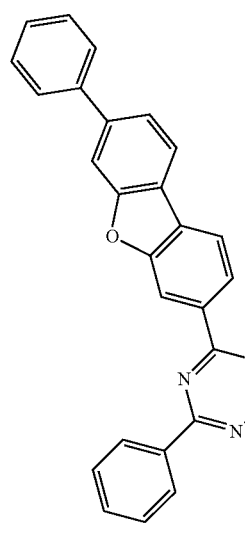

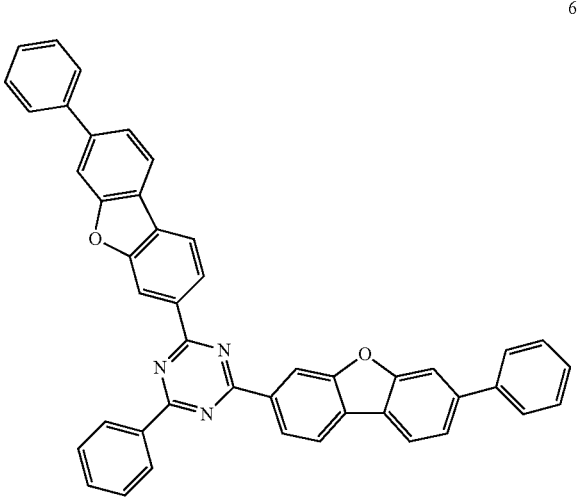

7
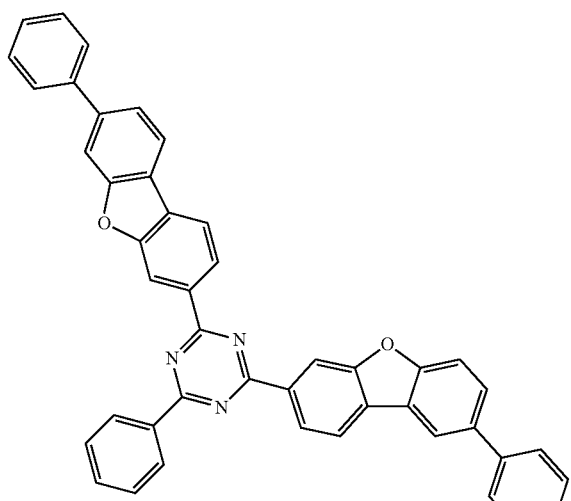
8
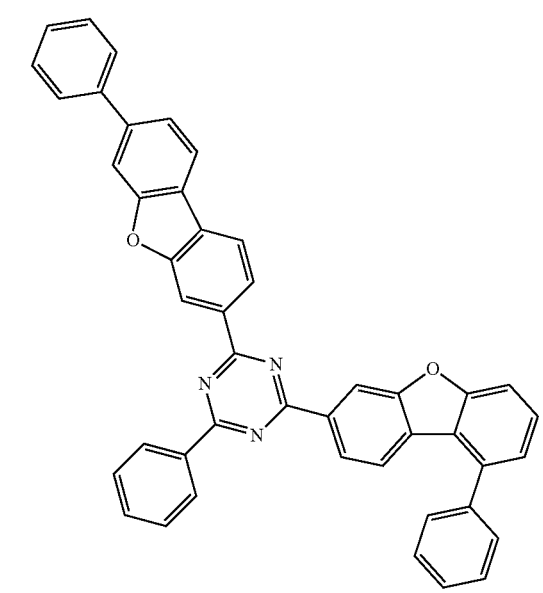
9
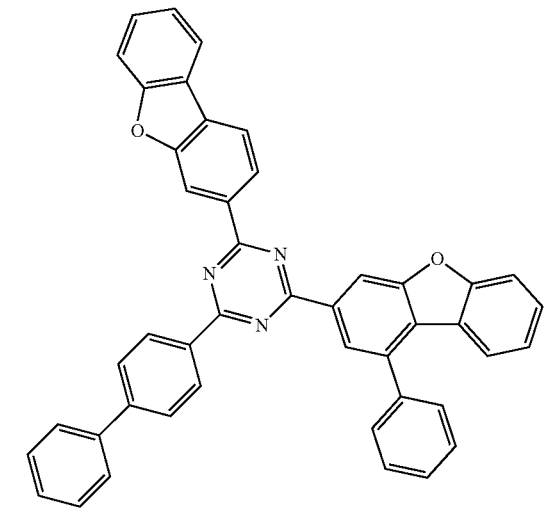
10
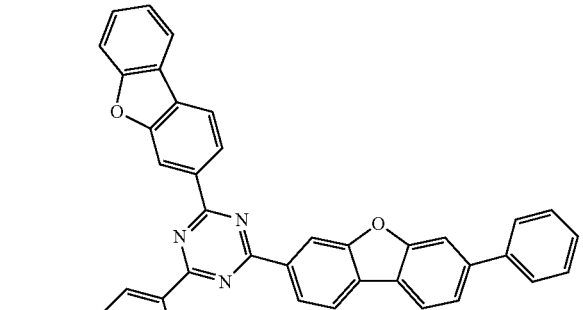
11
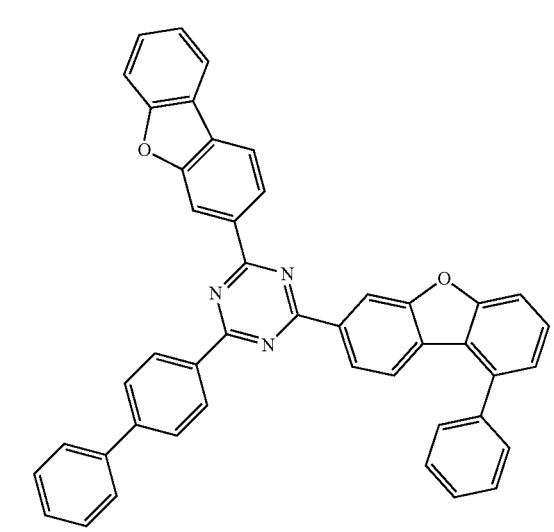
12

13
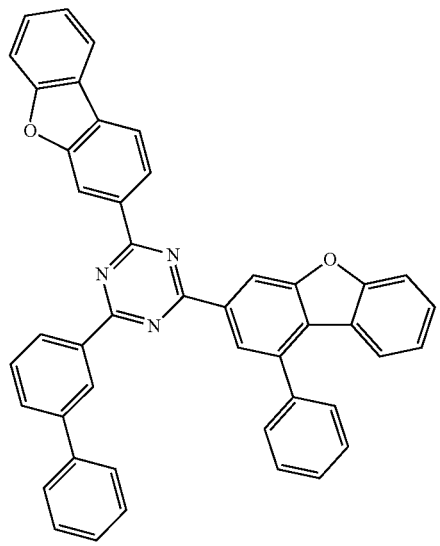
14
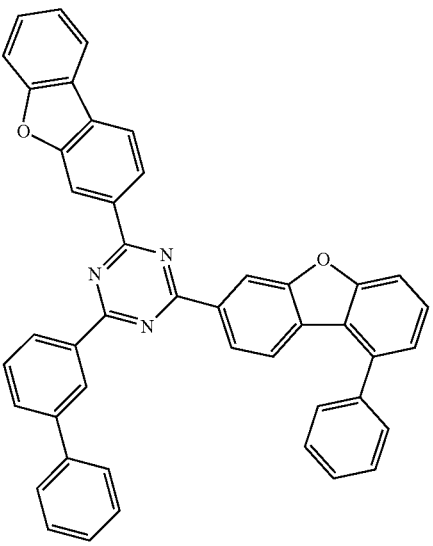
15
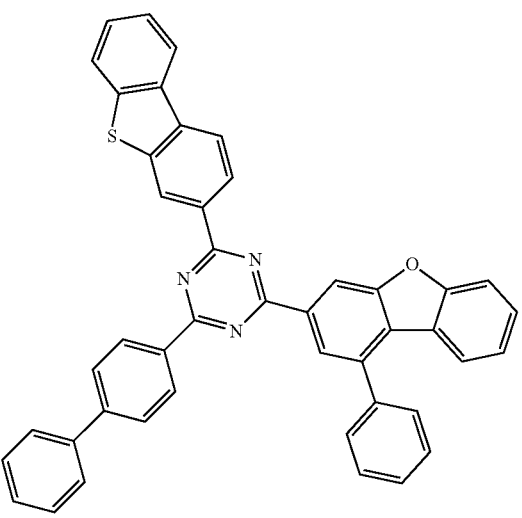
16
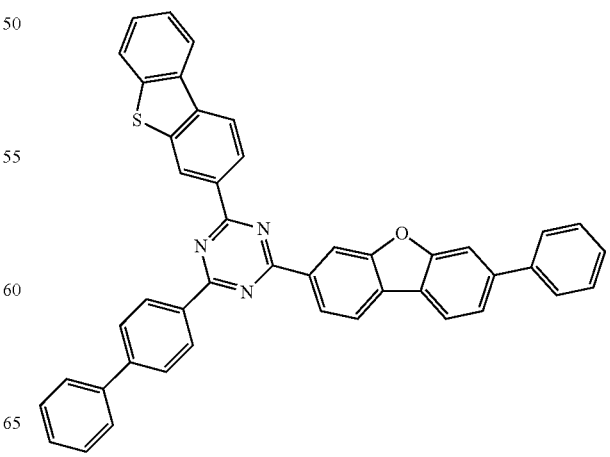

19
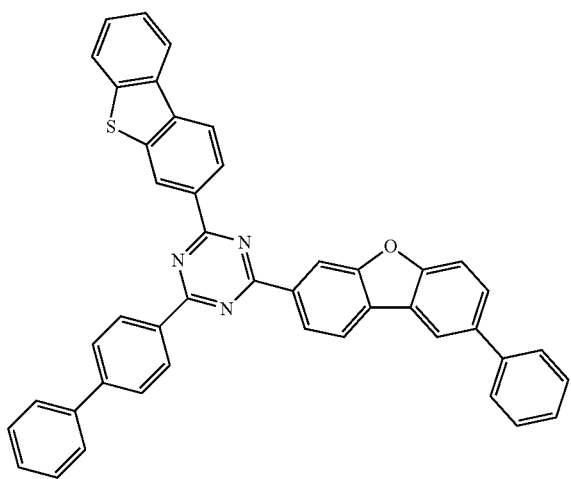
20
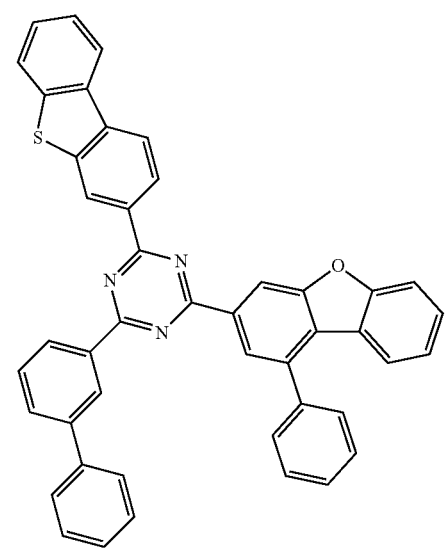
21
22
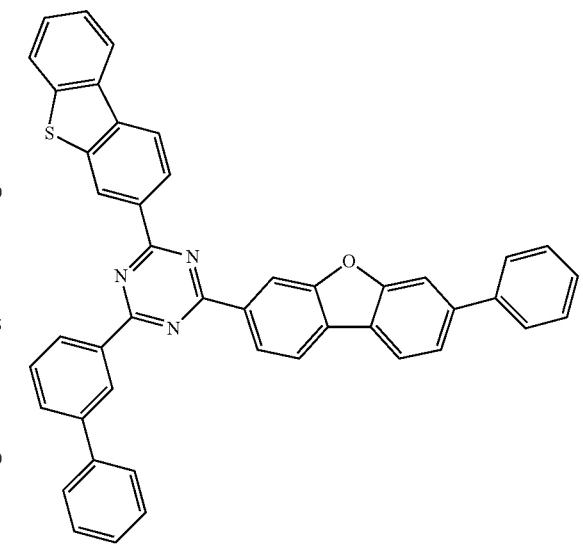
23
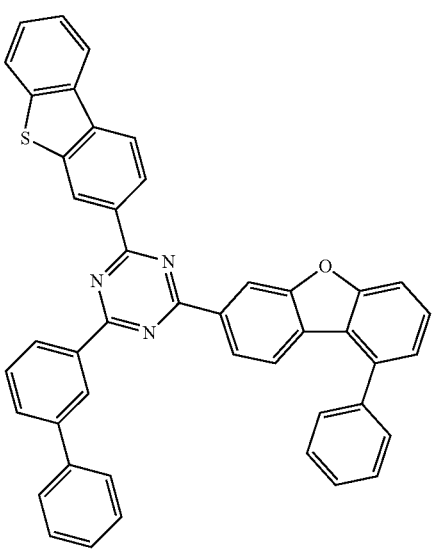
24

25
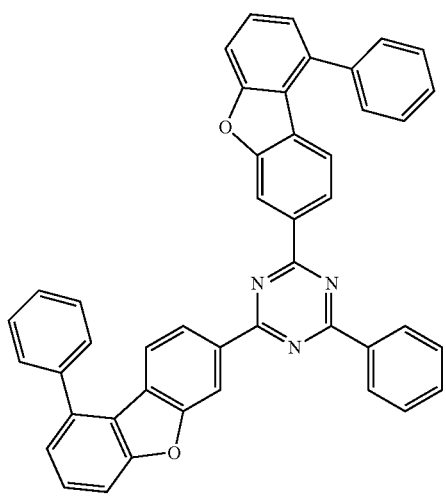
26
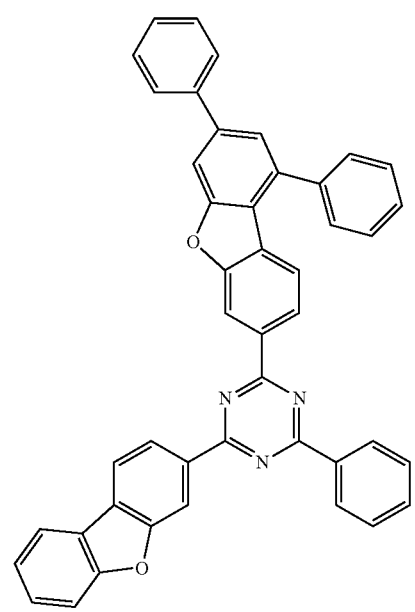
27
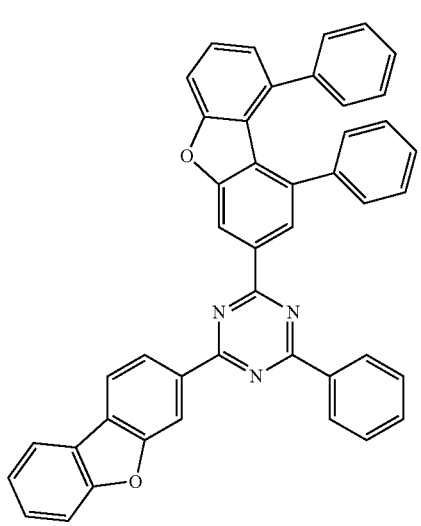
28
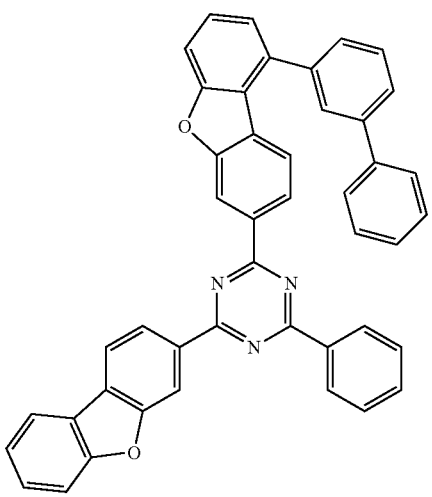
29
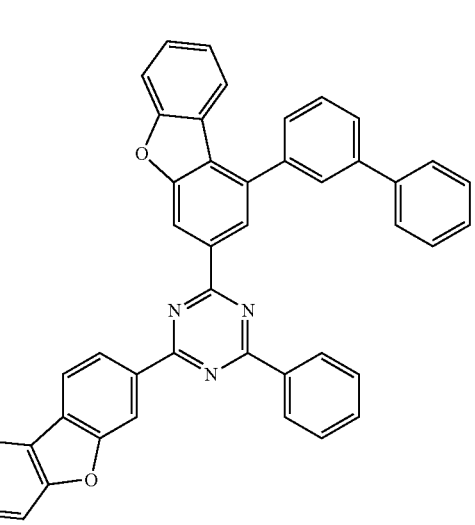
30
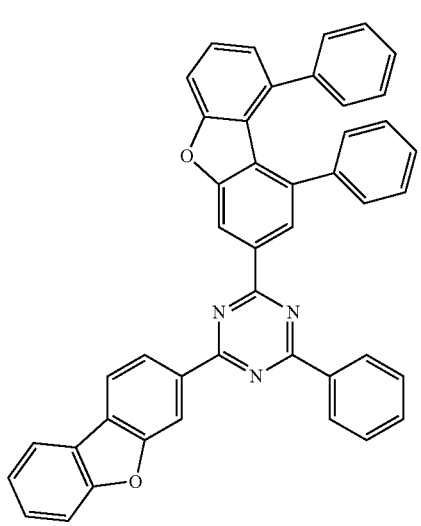

31
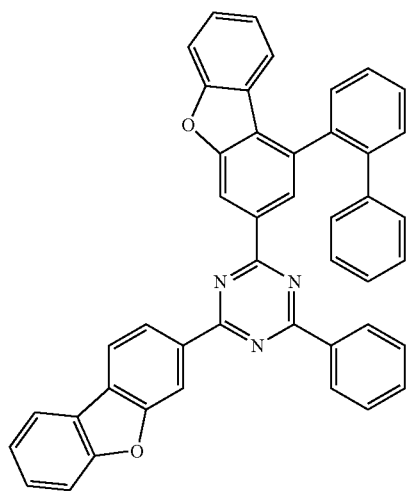
32
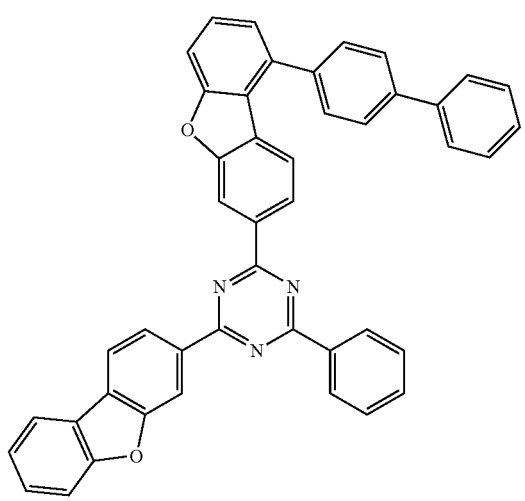
33
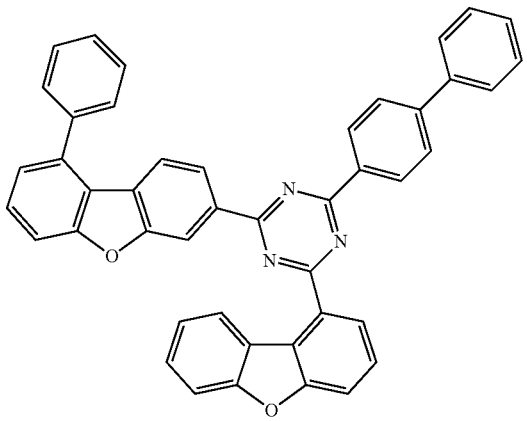
34
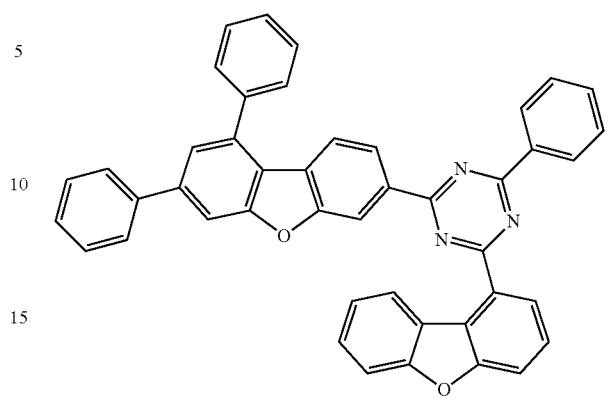
35
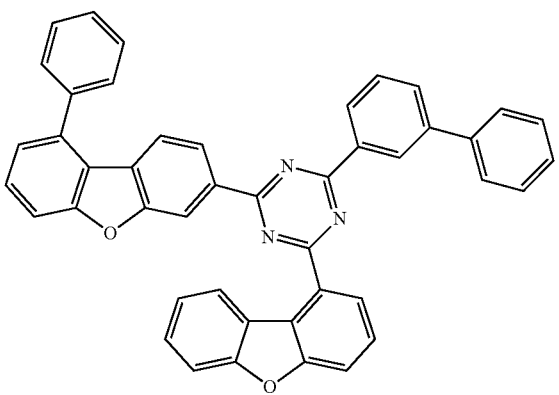
36

37
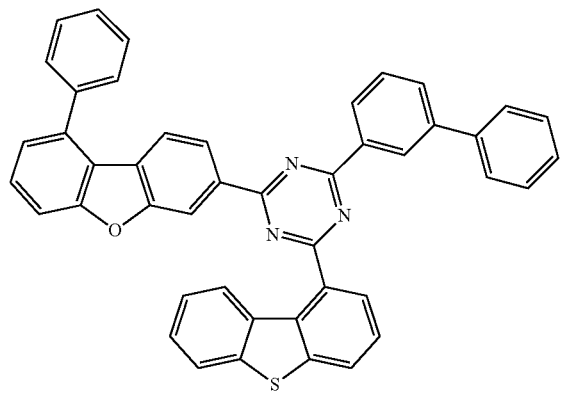
38
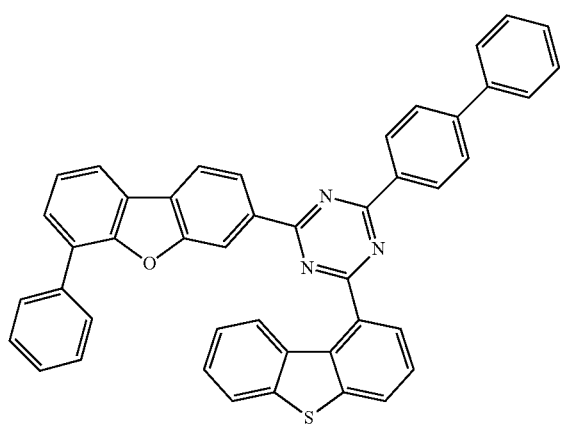
40
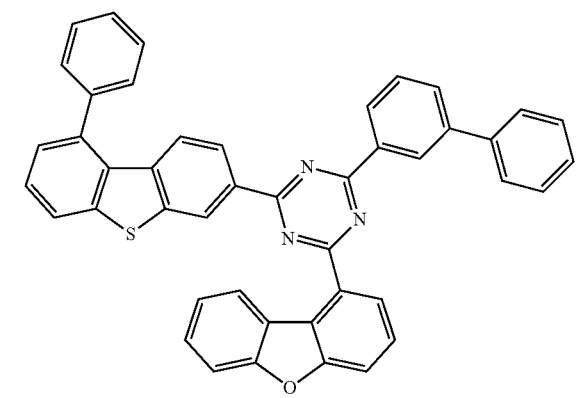
41
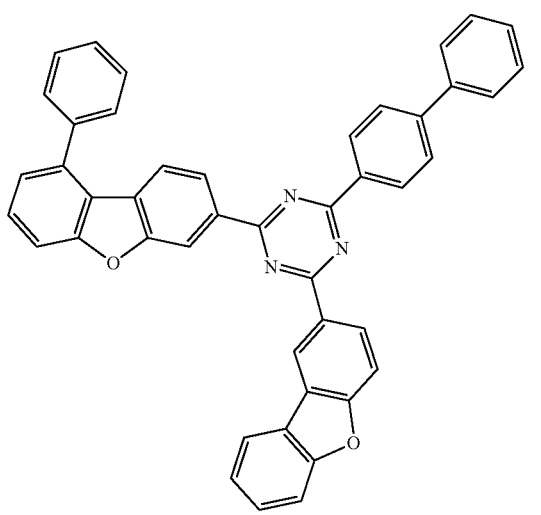
39
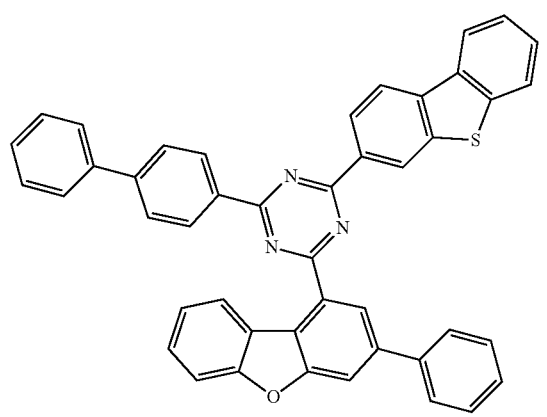
42
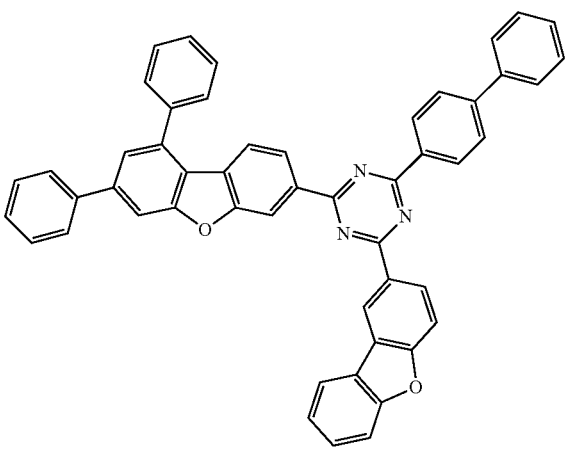

43
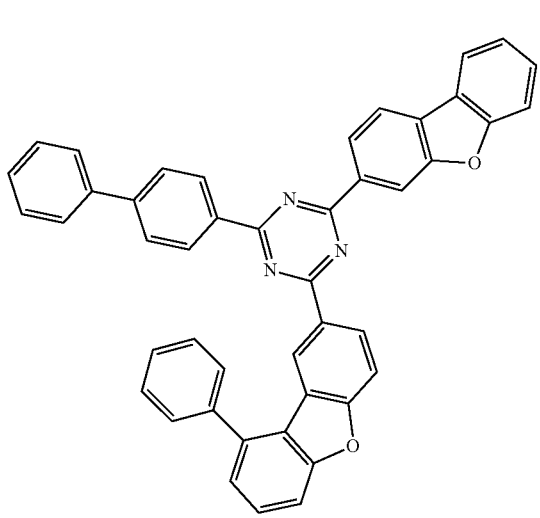
44
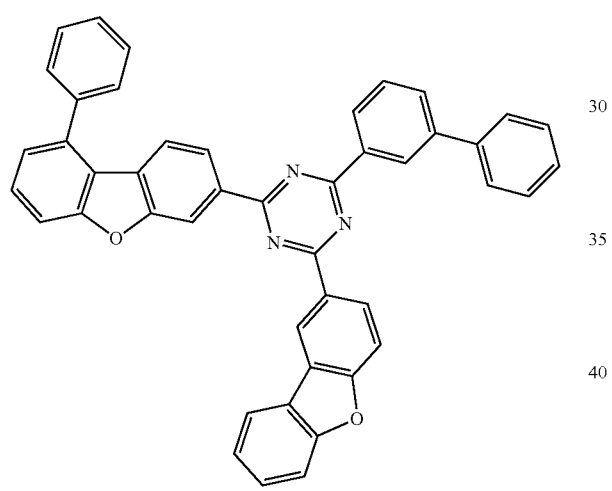
45
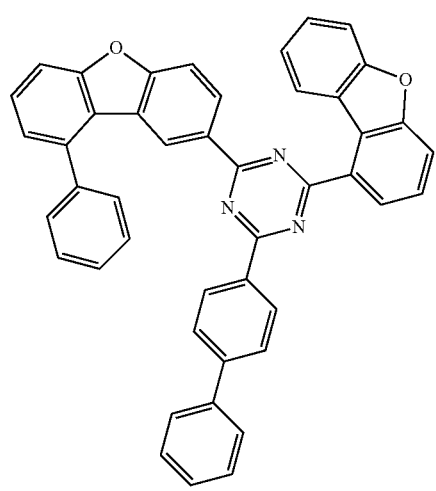
46
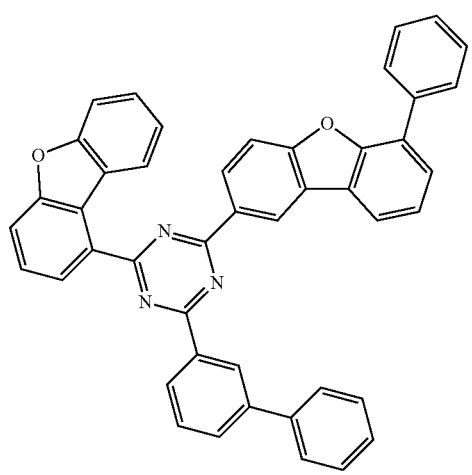
47
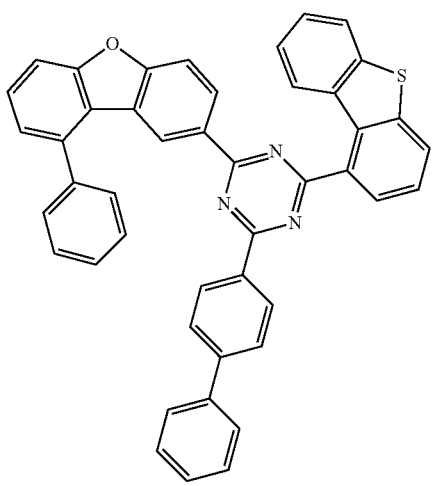
48
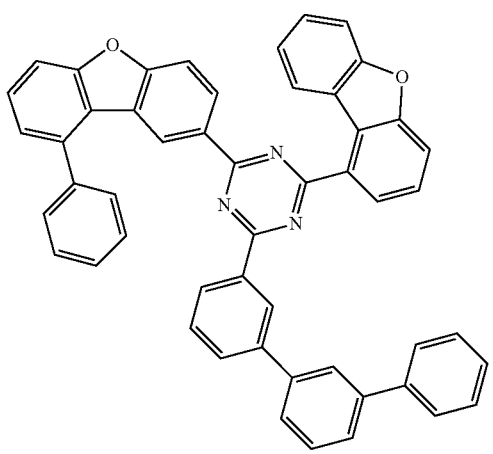

49
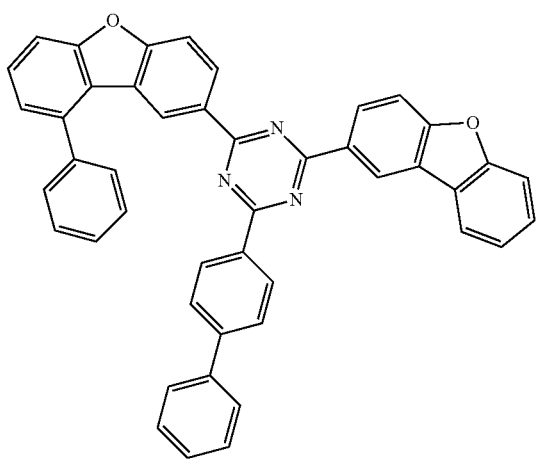
52
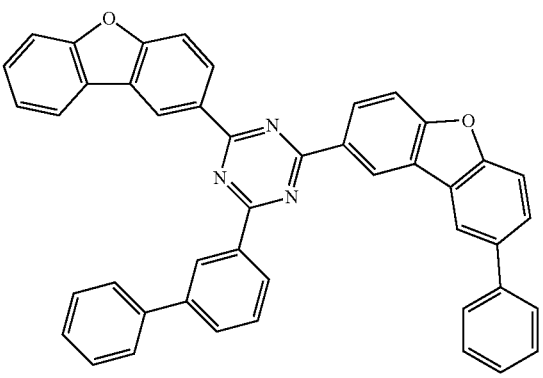
50
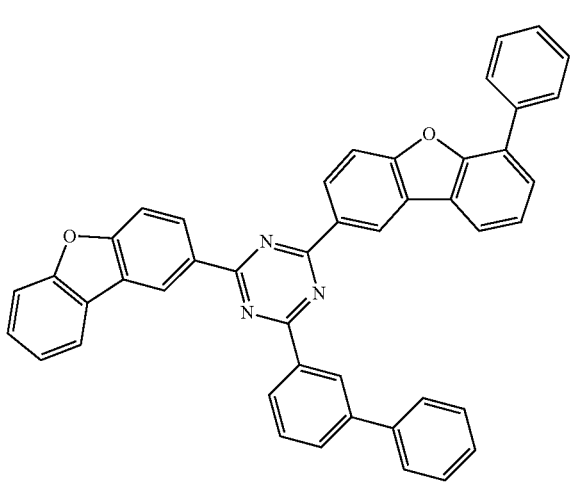
53
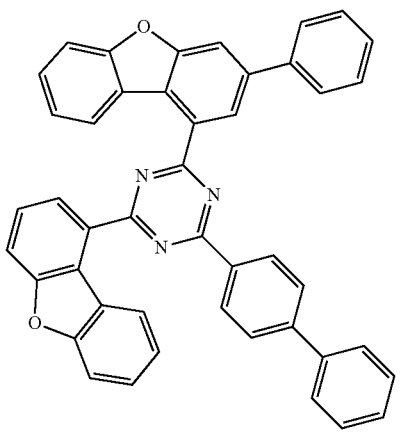
51
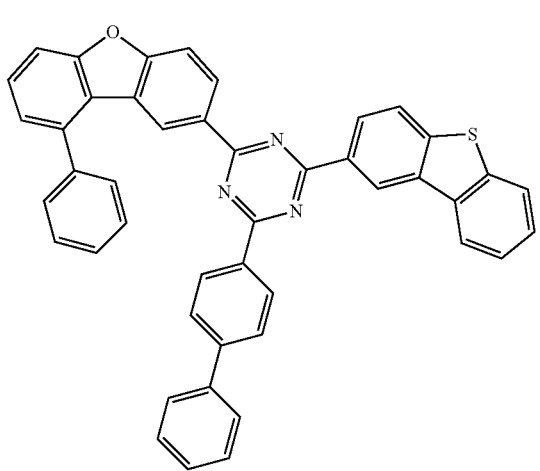
54
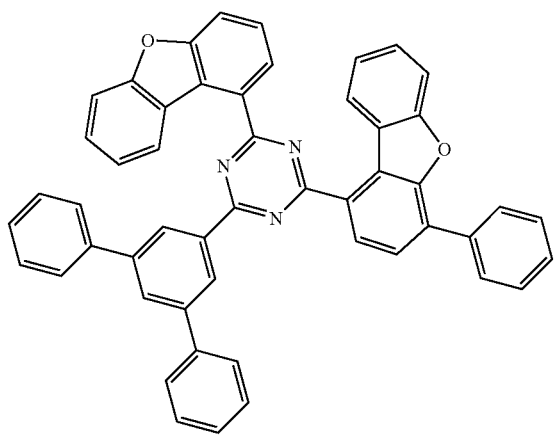

55

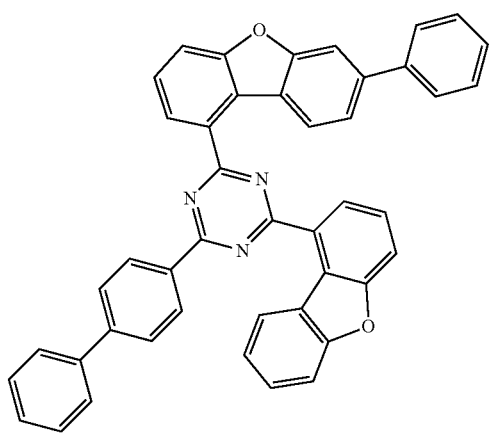

56

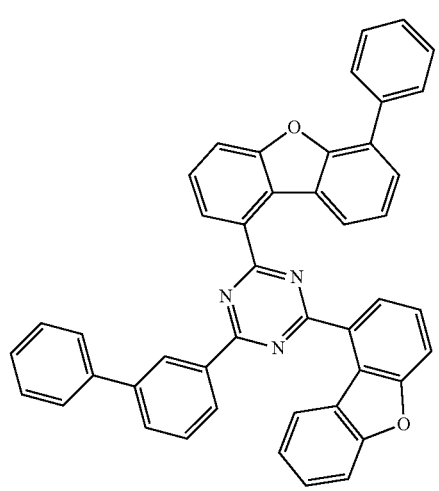

57

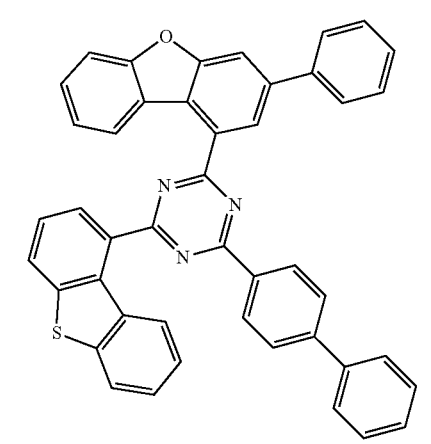

58

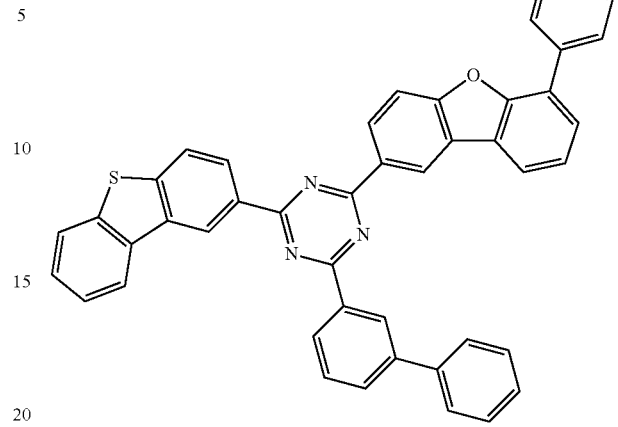

59

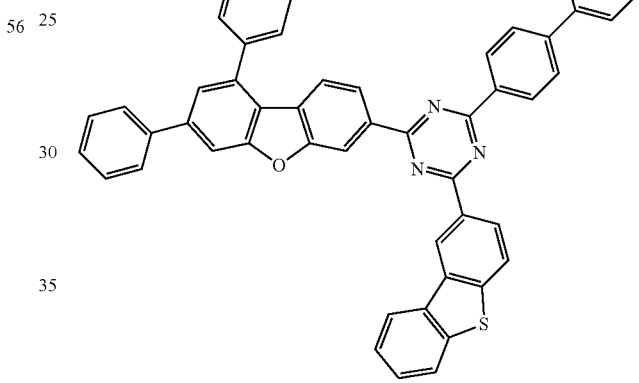

60

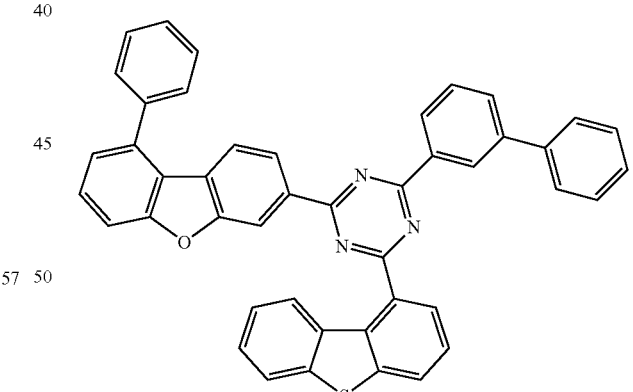

In addition, the compound for the organic optoelectronic diode represented by Chemical Formula 1 may be applied to an organic optoelectronic diode alone or in a form of a composition, or may be applied to an organic optoelectronic diode in a form of a composition together with another compound for an organic optoelectronic diode.

That is, according to another embodiment, a composition for an organic optoelectronic diode including the compound for the organic optoelectronic diode represented by Chemical Formula 1 is provided.

Hereinafter, an organic optoelectronic diode according to another embodiment is described.

The organic optoelectronic diode may be any element to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic diode is described referring to drawings.

FIGS. 1 and 2 are cross-sectional views of an organic light emitting diode according to embodiments.

Referring to FIG. 1, an organic optoelectronic diode 100 according to an embodiment includes an anode 120 and a cathode 110 facing each other and an organic layer 105 disposed between the anode 120 and cathode 110.

The anode 120 may be made of a conductor having a large work function to help hole injection and may be for example made of a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al, and $BaF_2$/Ca, but is not limited thereto.

The organic layer 105 includes a light emitting layer 130.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

An organic optoelectronic diode according to an embodiment includes an anode and a cathode facing each other, and an organic layer between the anode and the cathode, wherein the organic layer includes at least one of a hole injection layer, a hole transport layer, a light emitting layer, and an electron transport layer and the light emitting layer includes a composition for an organic optoelectronic diode including the compound represented by Chemical Formula 1, as a first host.

For example, the light emitting layer may further include a first host represented by Chemical Formula 1 and a compound (second host) represented by a combination of Chemical Formula 6 and Chemical Formula 7.

[Chemical Formula 6]

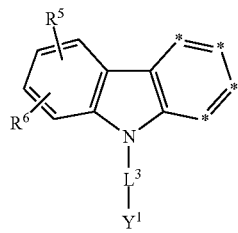

[Chemical Formula 7]

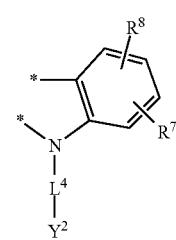

In Chemical Formula 6 to Chemical Formula 7, $Y^1$ and $Y^2$ are independently a substituted or unsubstituted C6 to C20 aryl group, or a substituted or unsubstituted C2 to C30 heterocyclic group, two adjacent *'s in Chemical Formula 6 are linked to Chemical Formula 7,

*'s of Chemical Formula 6 not linked to Chemical Formula 7 is independently $C-L^a-R^b$, $L^a$, $L^3$, and $L^4$ are independently a single bond, or a substituted or unsubstituted C6 to C20 arylene group, and $R^b$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

The compound represented by the combination of Chemical Formulae 6 and 7 may be combined along with indolocarbazole as a second host and thus balance between holes and electron and resultantly, realize low driving/high efficiency characteristics.

Simultaneously, when additionally combined with a phosphorescent dopant including a dibenzofuranyl group, a dibenzothiophenyl group, or derivative groups thereof including N which will be described later, an advantage of the combinations such as packing host and dopant materials, energy transfer, and the like may be secured.

The compound represented by the combination of Chemical Formula 6 and Chemical Formula 7 may be represented by one of Chemical Formula 6A, Chemical Formula 6B, Chemical Formula 6C, and Chemical Formula 6D.

[Chemical Formula 6A]

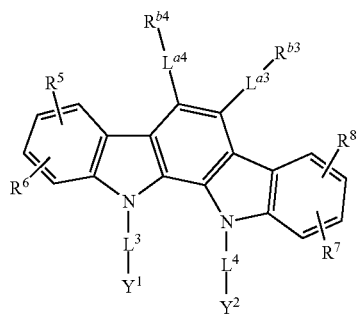

[Chemical Formula 6B]

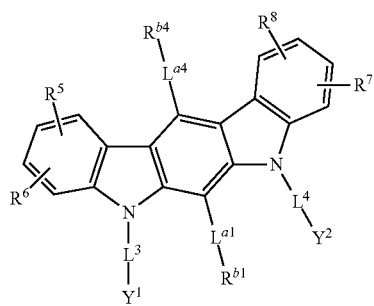

[Chemical Formula 6C]

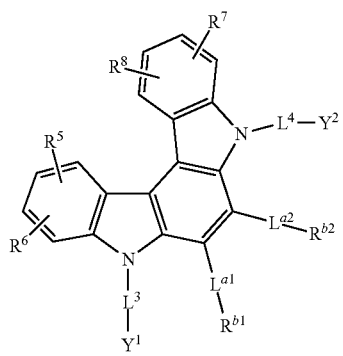

[Chemical Formula 6D]

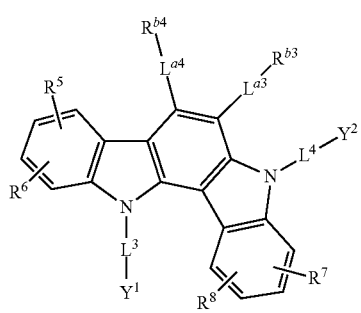

In Chemical Formula 6A to Chemical Formula 6D, $Y^1$ and $Y^2$ are independently a substituted or unsubstituted C6 to C20 aryl group or a substituted or unsubstituted C2 to C30 heterocyclic group, $L^{a1}$ to $L^{a4}$, $L^3$, and $L^4$ are independently a single bond or a substituted or unsubstituted C6 to C20 arylene group, and $R^{b1}$ to $R^{b4}$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

For example, $Y^1$ and $Y^2$ may independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group and $R^{b1}$ to $R^{b4}$ and $R^5$ to $R^8$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

$Y^1$, $Y^2$, $R^{b1}$ to $R^{b4}$, and $R^5$ to $R^8$ may be selected from, for example, the substituents of Group II.

[Group II]

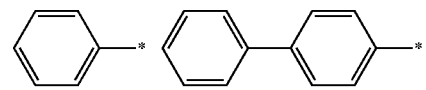

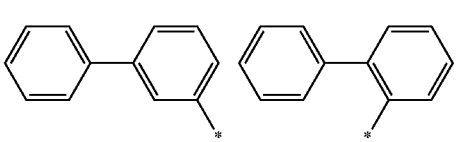

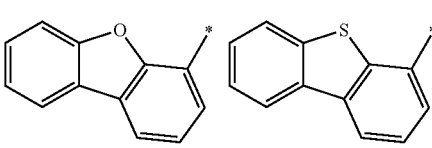

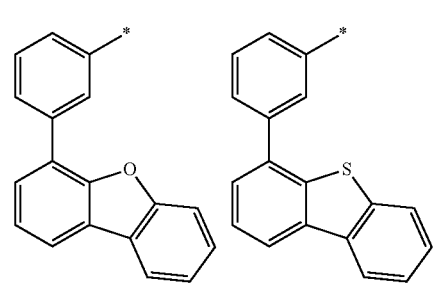

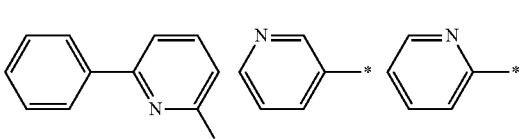

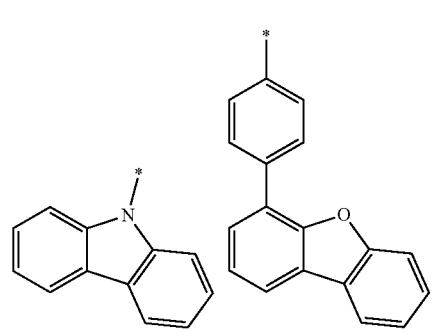

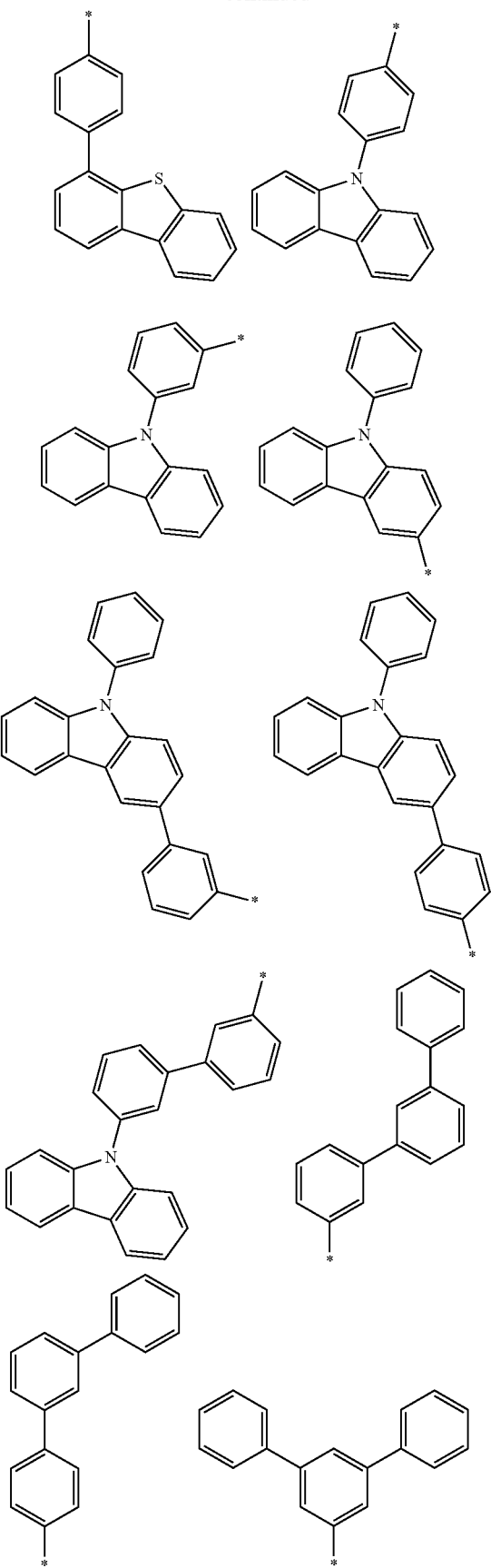

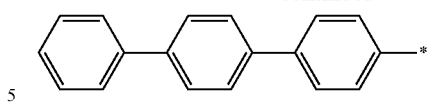

In Group II, * is a linking point.

In addition, in an embodiment of the present invention, $L^{a1}$ to $L^{a4}$ and $L^3$ and $L^4$ may independently be a single bond, a substituted or unsubstituted para-phenylene group, a substituted or unsubstituted meta-phenylene group, or a substituted or unsubstituted biphenylene group, and in a specific embodiment, $L^{a1}$ to $L^{a4}$ and $L^3$ and $L^4$ may independently be a single bond, a substituted or unsubstituted para-phenylene group, or a substituted or unsubstituted meta-phenylene group, and desirably, $L^{a1}$ to $L^{a4}$ and $L^3$ and $L^4$ may independently be a single bond or a para-phenylene group.

The second host may be selected from compounds of Group 2, but is not limited thereto.

[Group 2]

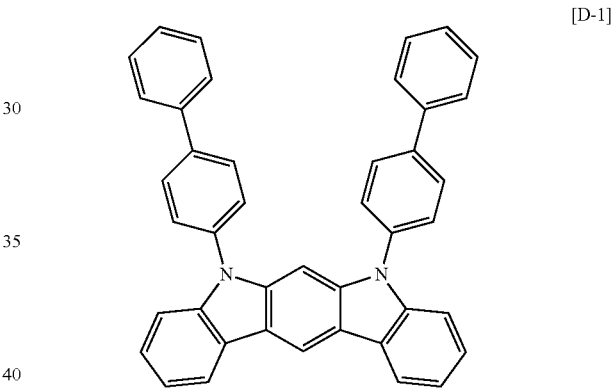

[D-1]

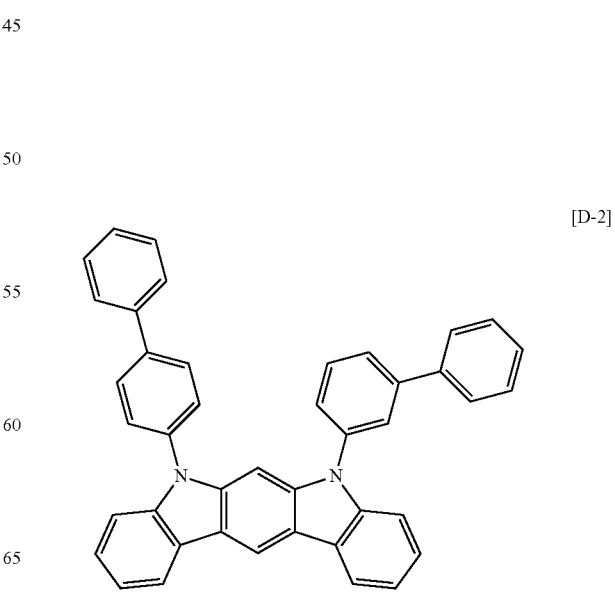

[D-2]

[D-3]
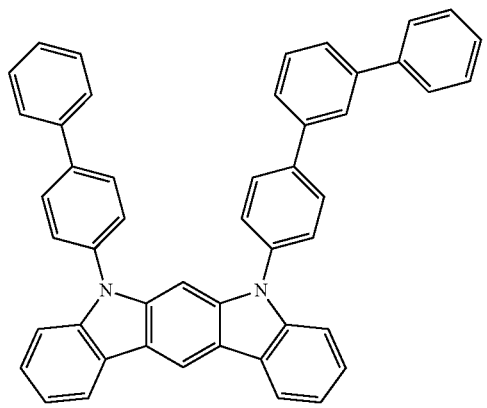
[D-4]
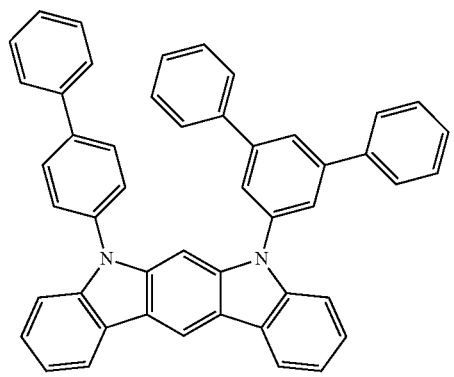
[D-5]
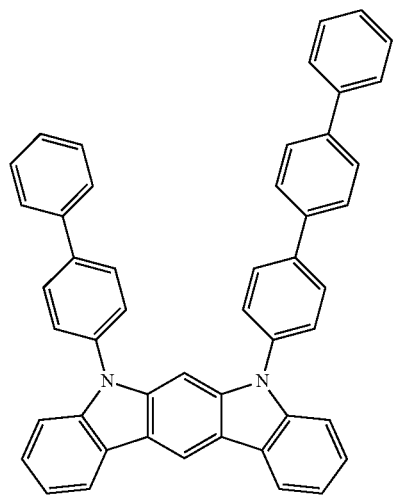
[D-6]
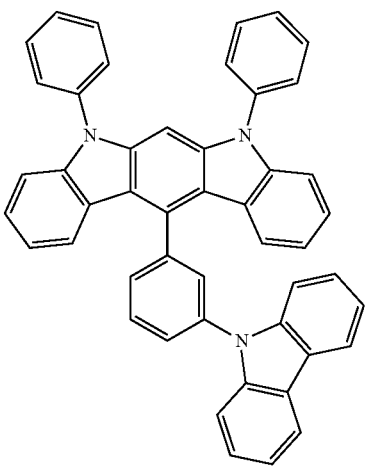
[D-7]
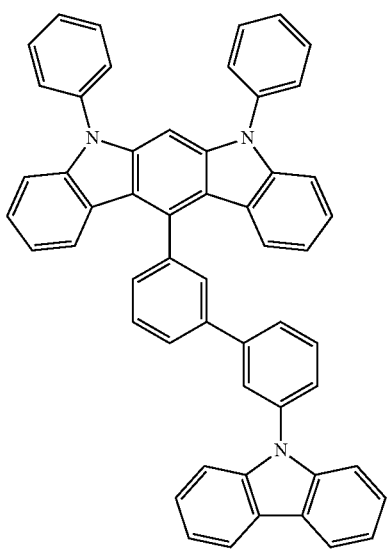
[D-8]
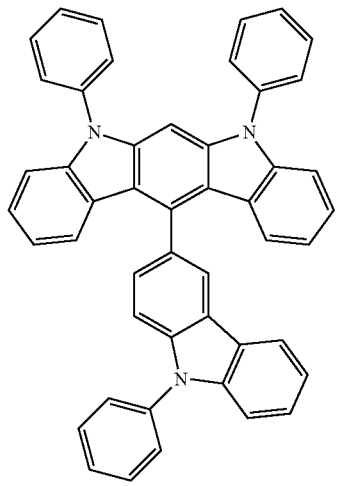

[D-9]
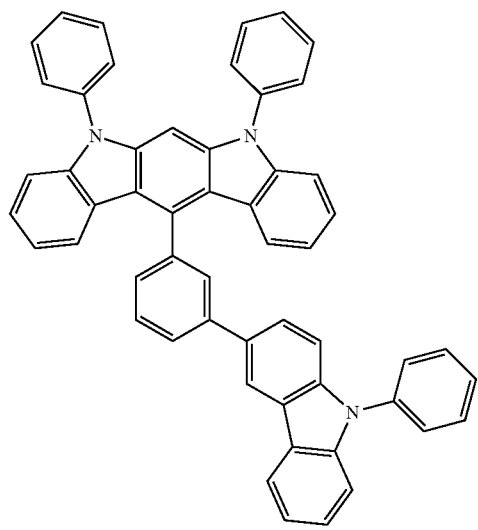
[D-10]
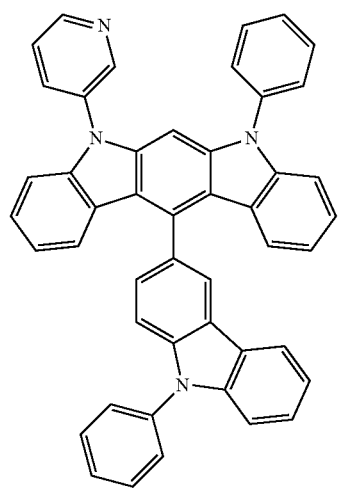
[D-11]
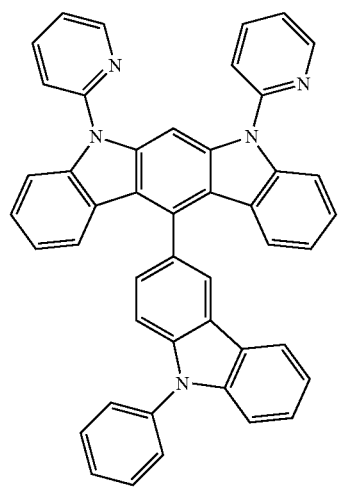
[D-12]
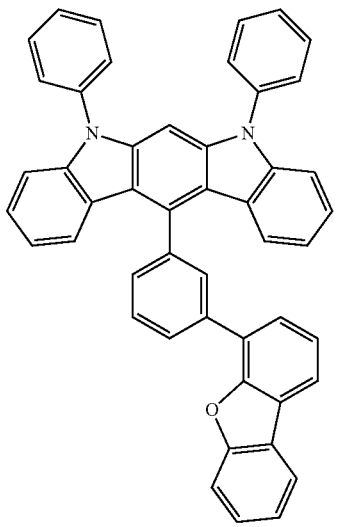
[D-13]
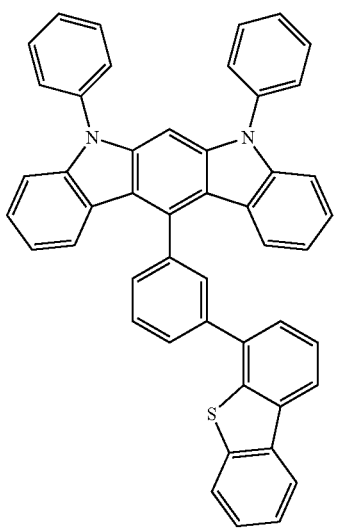
[D-14]
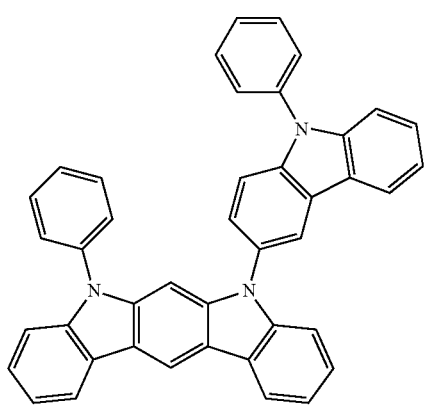

-continued
[D-15]
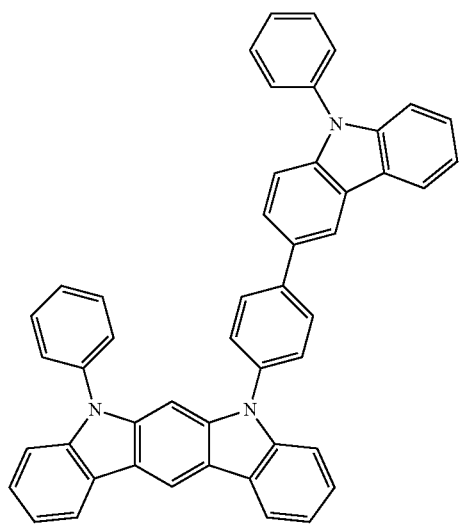
[D-18]
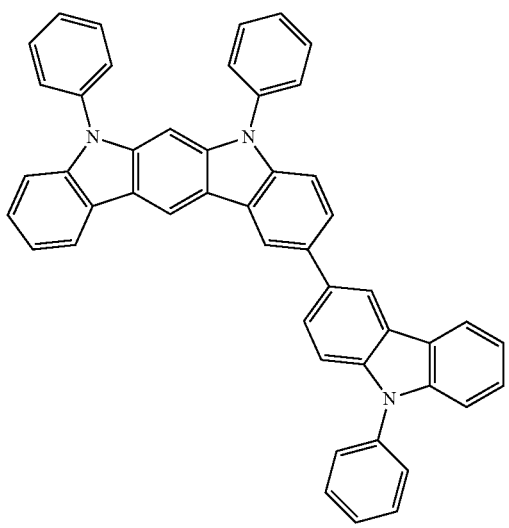
[D-16]
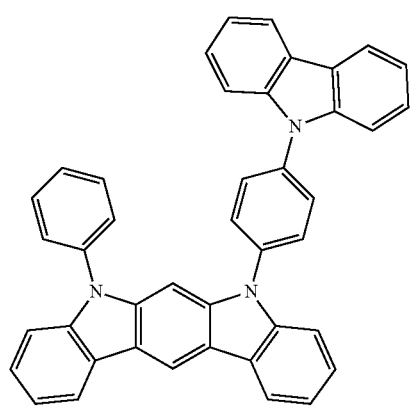
[D-19]
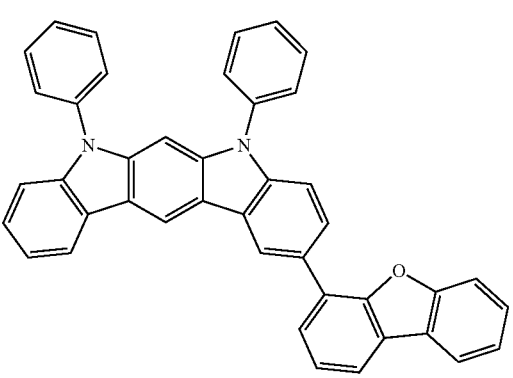
[D-17]
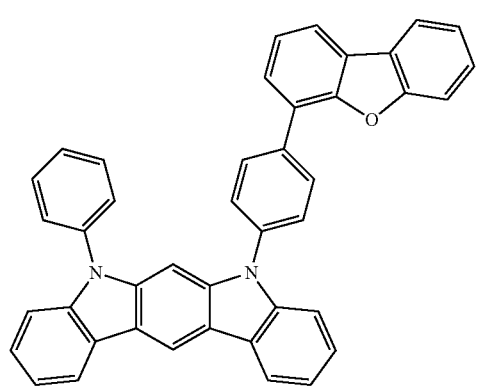
[D-20]
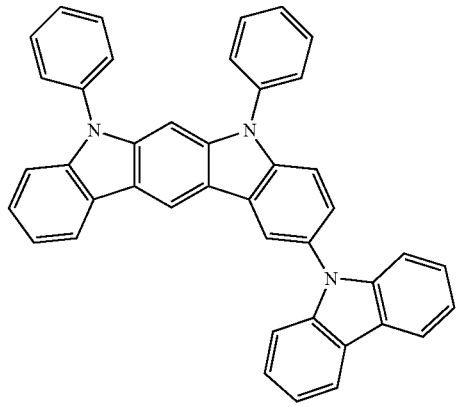

[D-21]
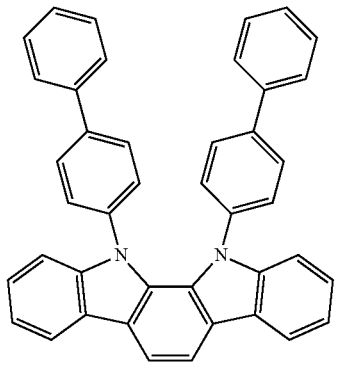
[D-22]
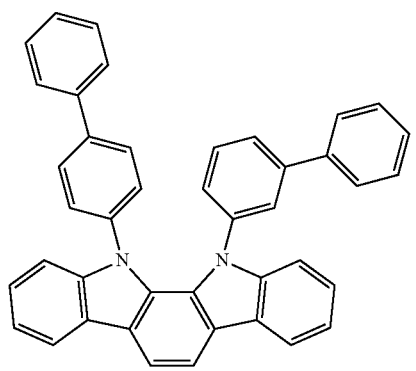
[D-23]
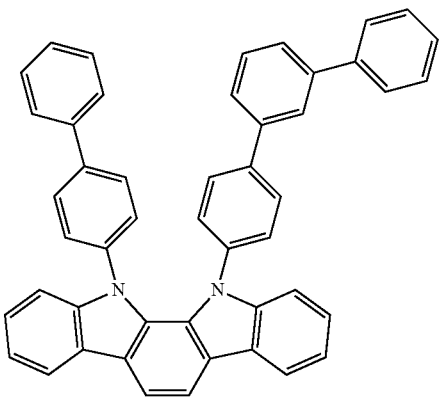
[D-24]
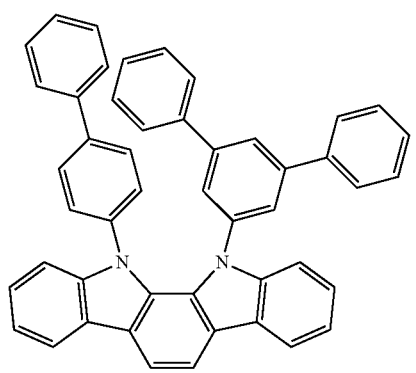
[D-25]
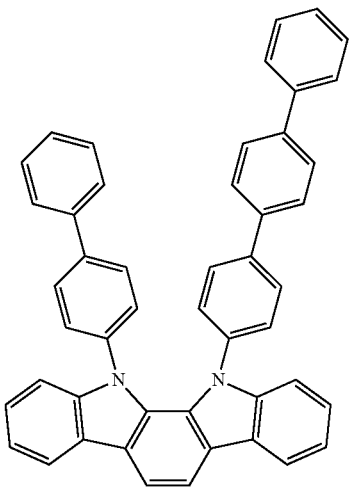
[D-26]
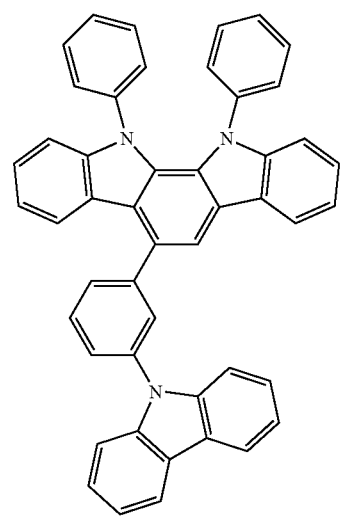
[D-27]
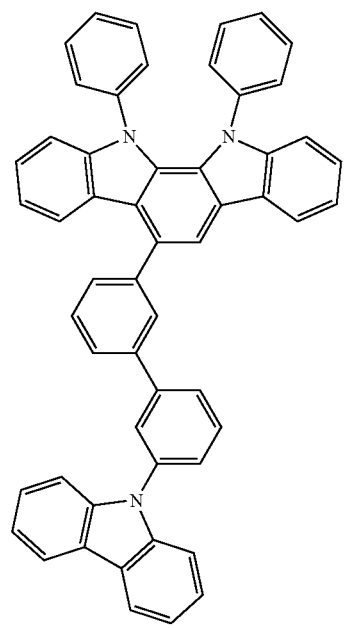

[D-28]
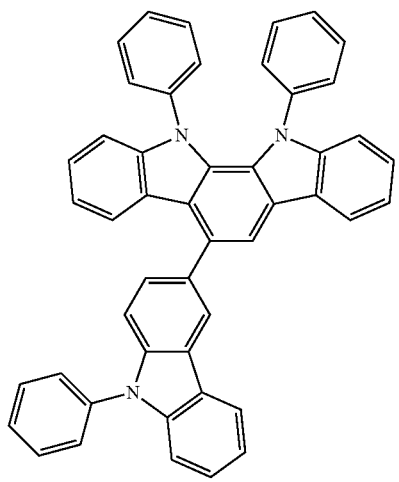
[D-31]
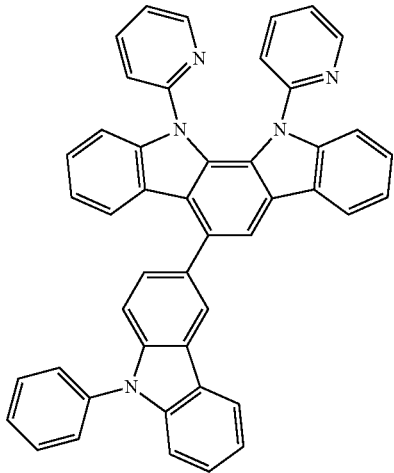
[D-29]
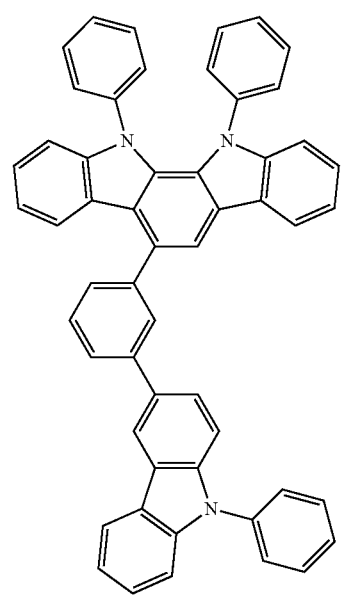
[D-32]
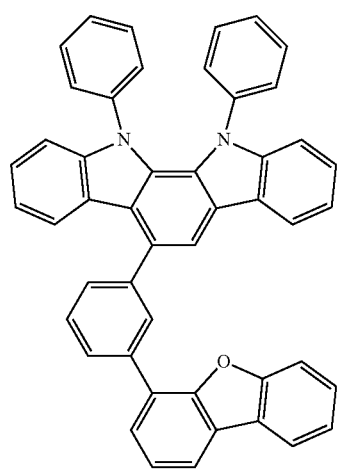
[D-30]
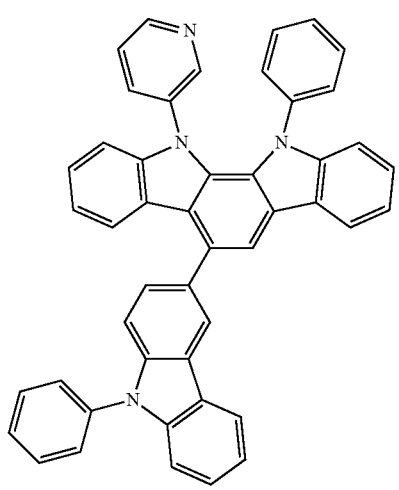
[D-33]
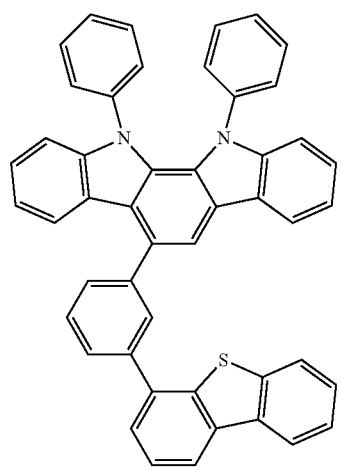

[D-34]
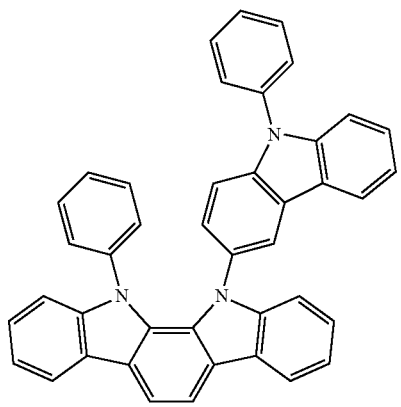
[D-35]
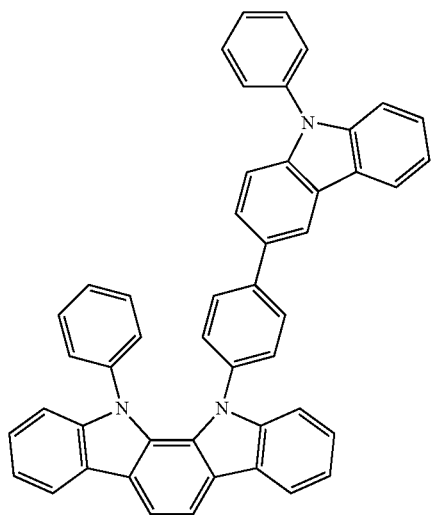
[D-36]
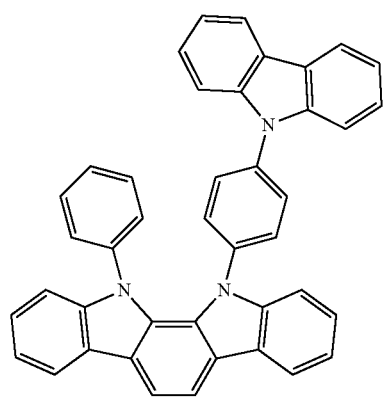
[D-37]
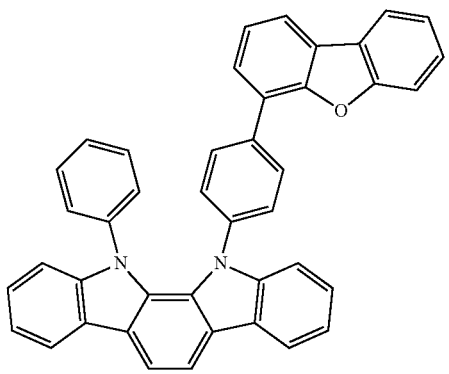
[D-38]
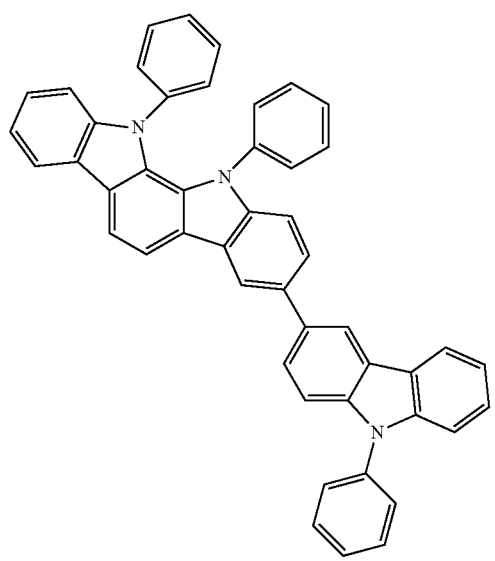
[D-39]
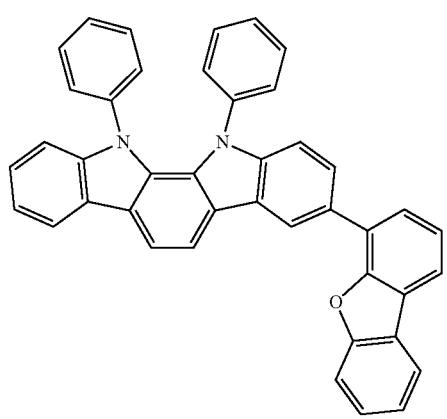

[D-40]
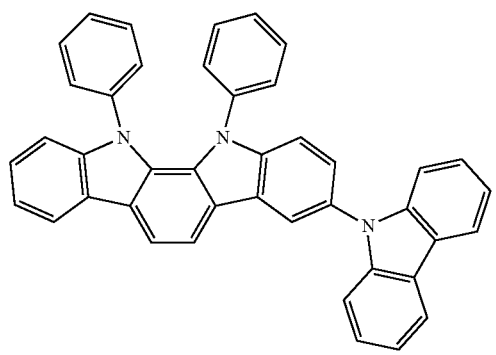
[D-43]
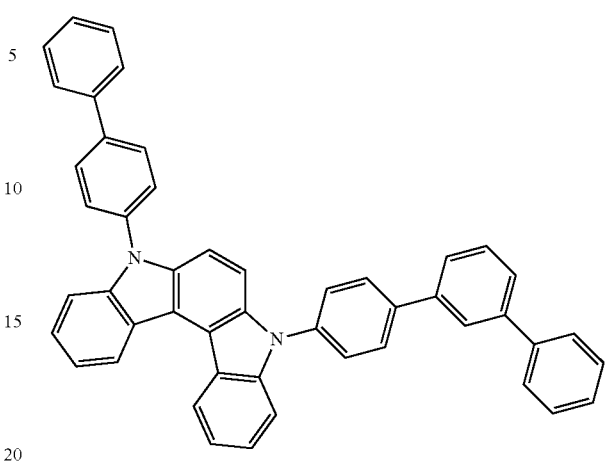
[D-41]
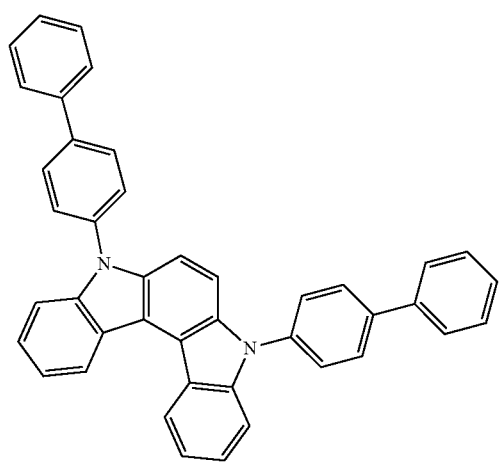
[D-44]
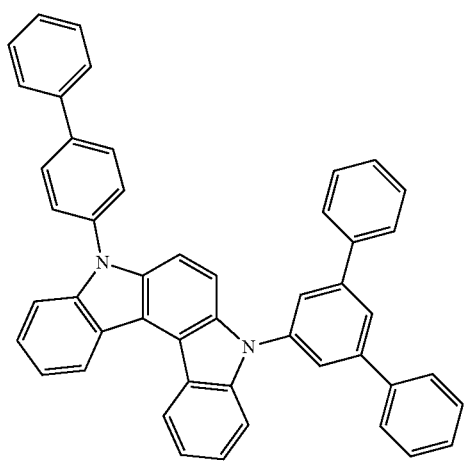
[D-42]
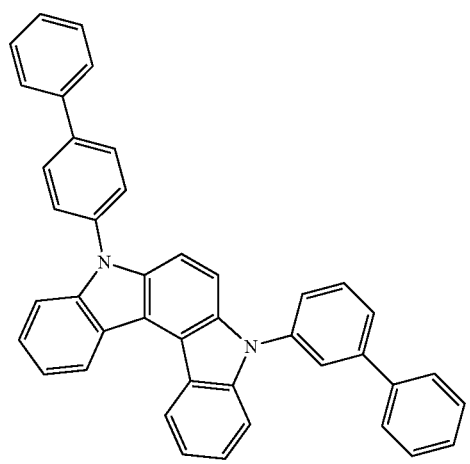
[D-45]
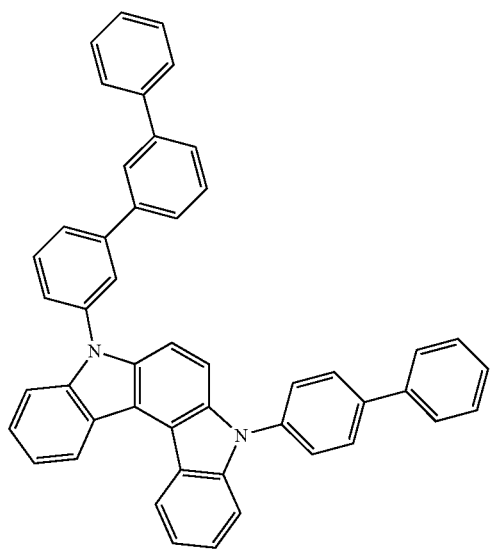

[D-46]
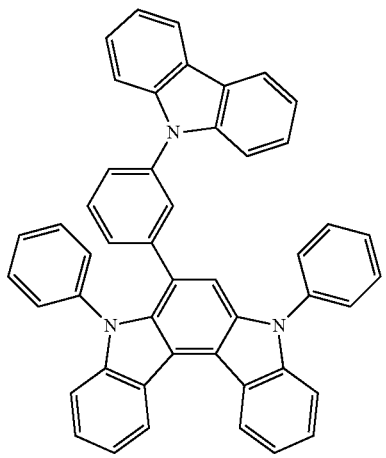
[D-47]
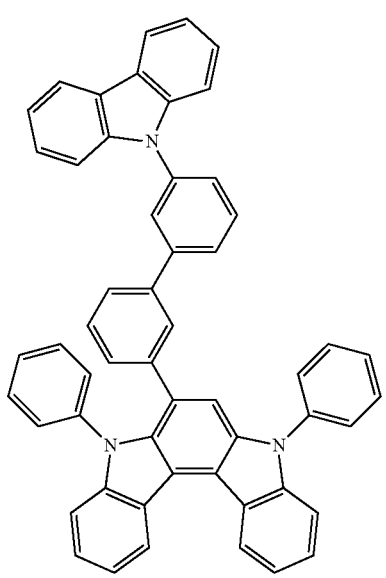
[D-48]
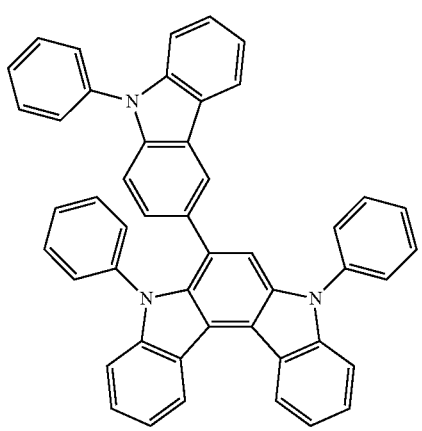
[D-49]
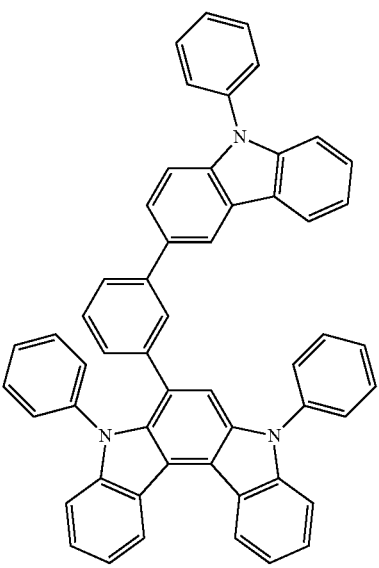
[D-50]
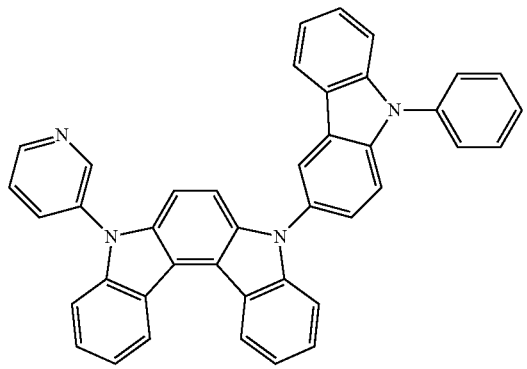
[D-51]
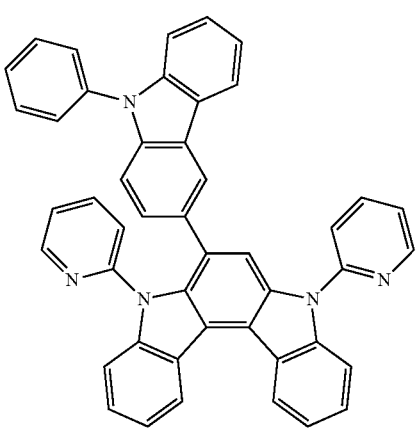

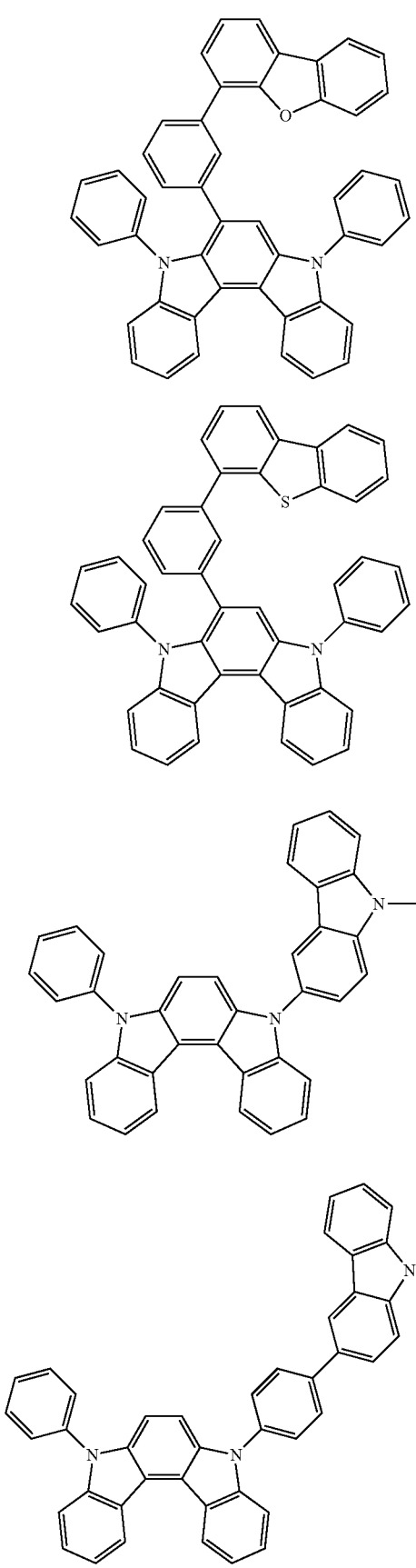

[D-59]
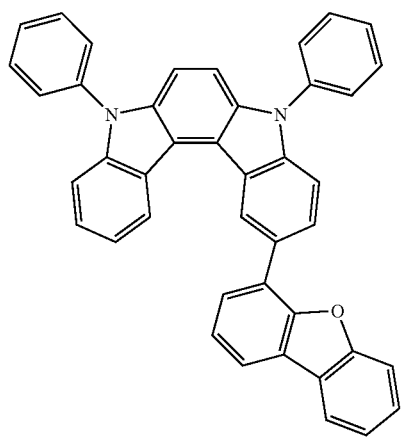
[D-60]
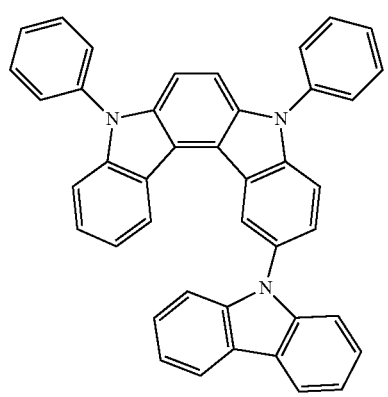
[D-61]
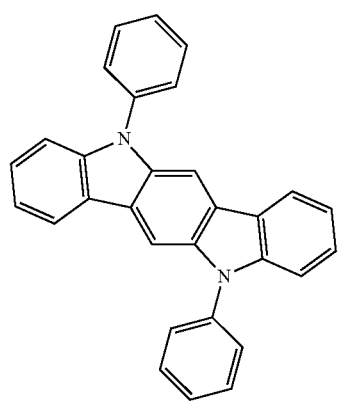
[D-62]
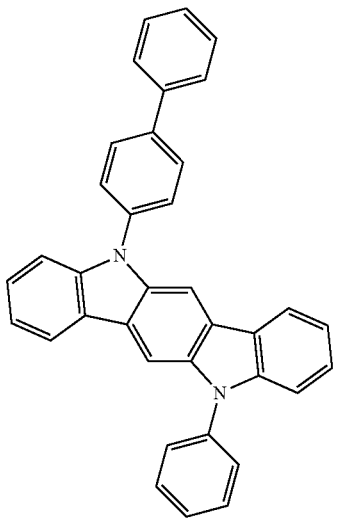
[D-63]
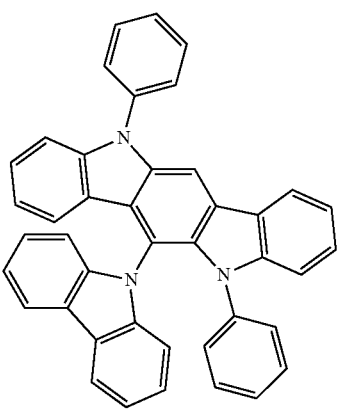
[D-64]
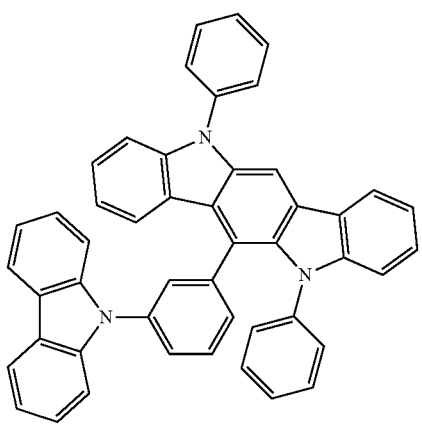

[D-65]
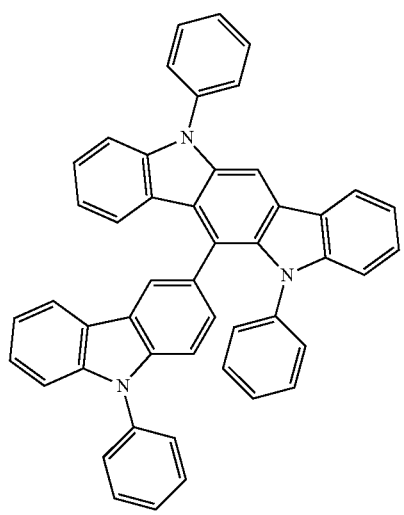
[D-68]
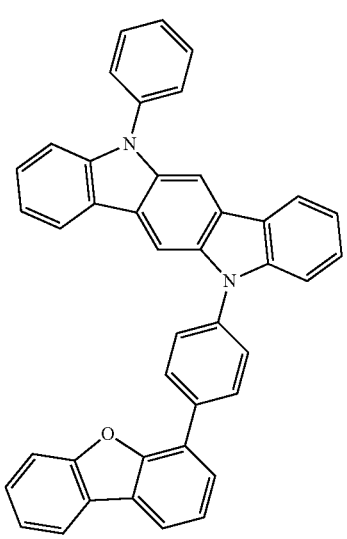
[D-66]
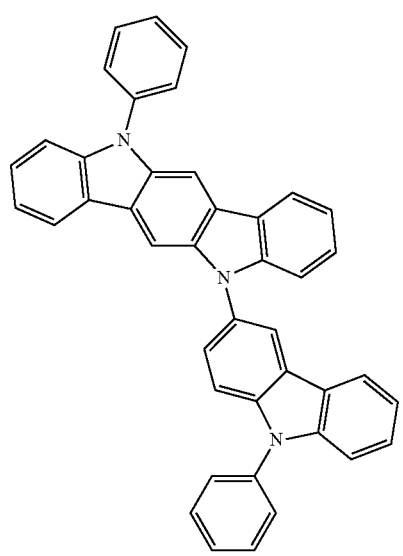
[D-69]
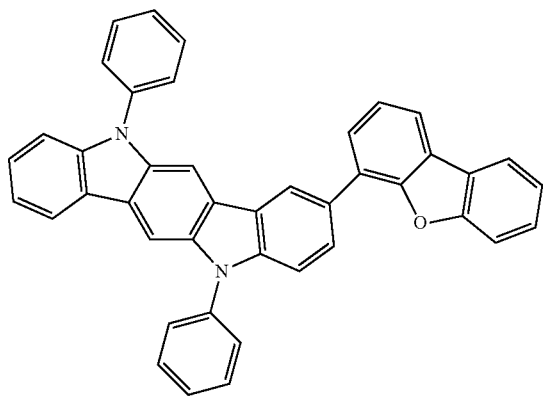
[D-67]
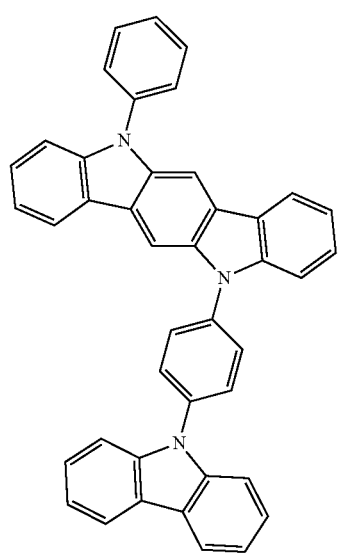
[D-70]
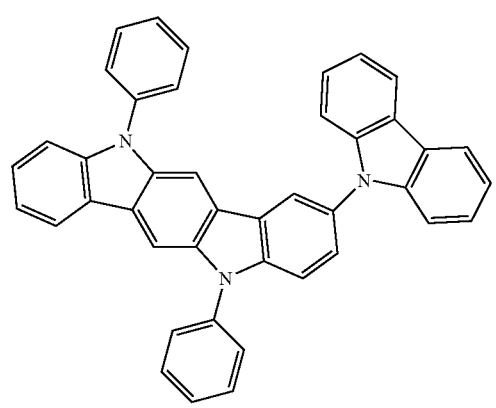

[D-71]
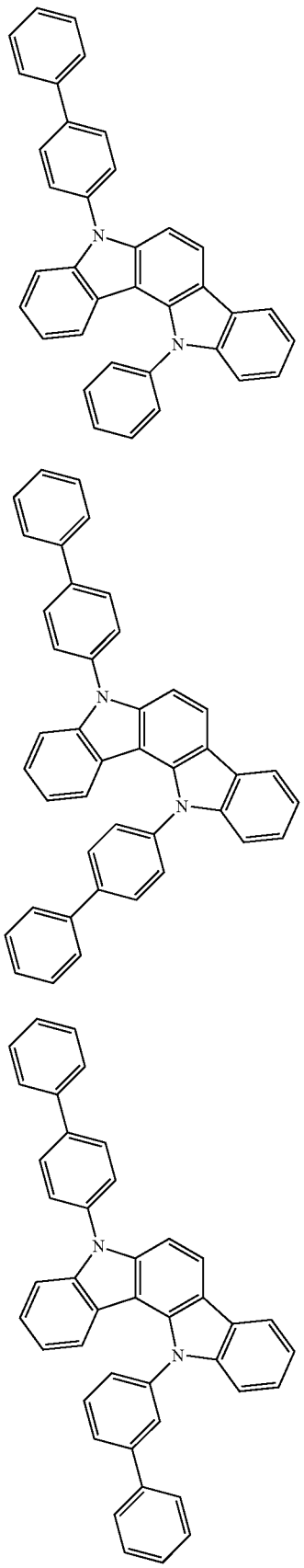
[D-72]
[D-73]
[D-74]
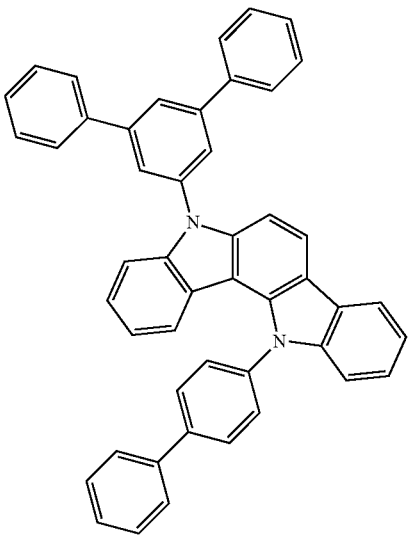
[D-75]
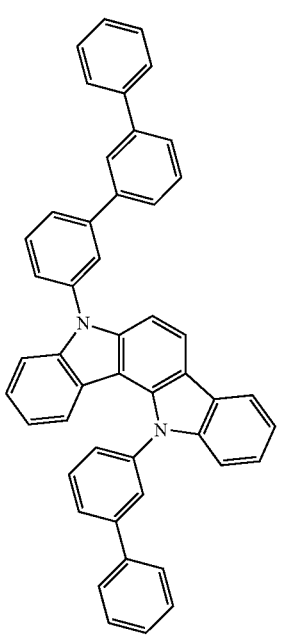
[D-76]
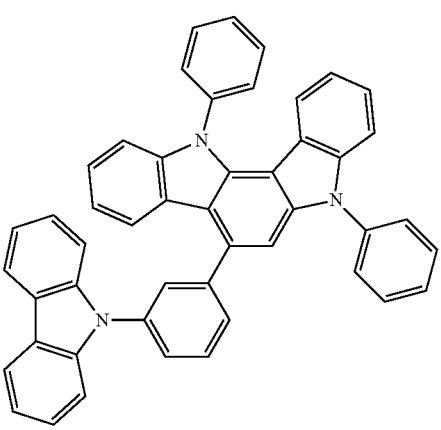

[D-77]
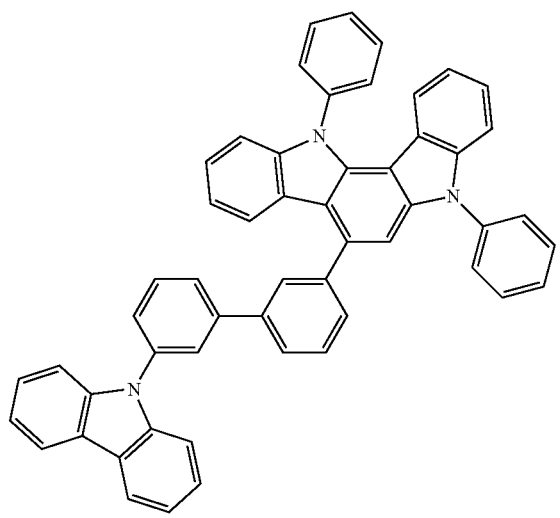
[D-78]
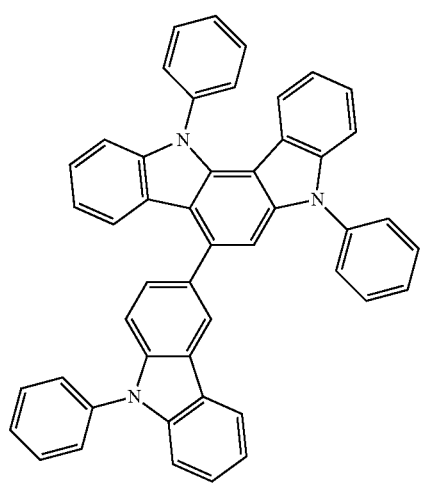
[D-79]
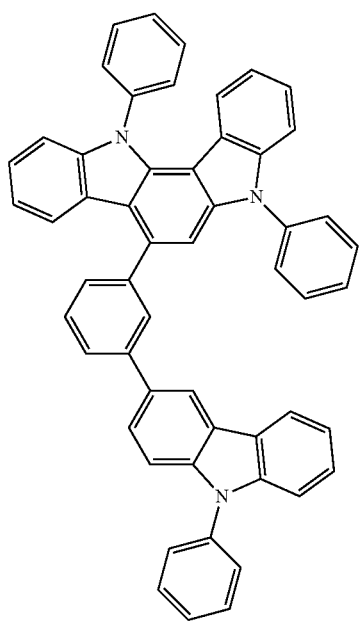
[D-80]
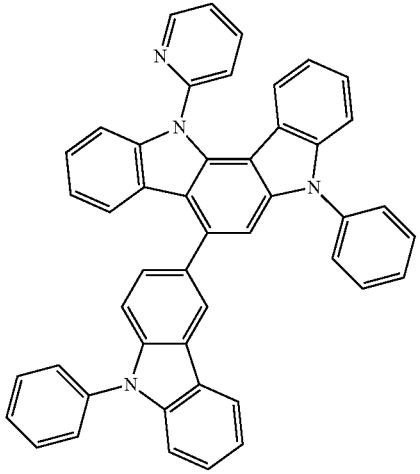
[D-81]
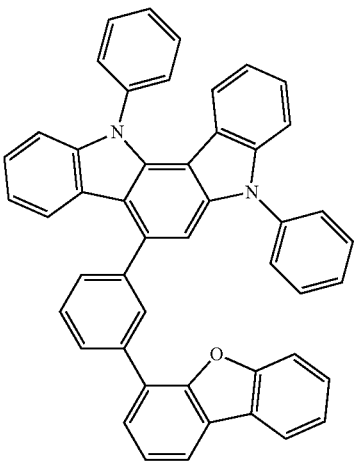
[D-82]
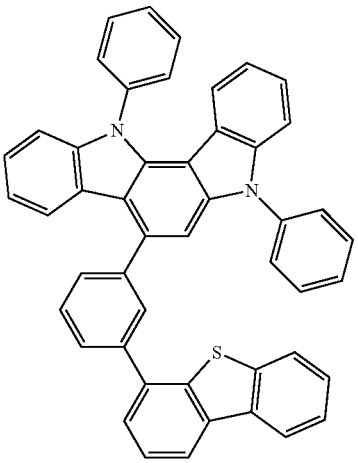

-continued
[D-83]
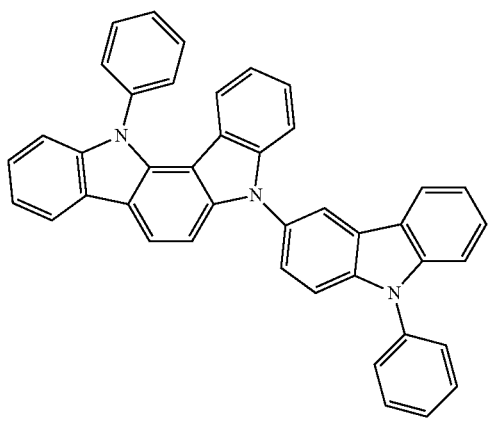
[D-84]
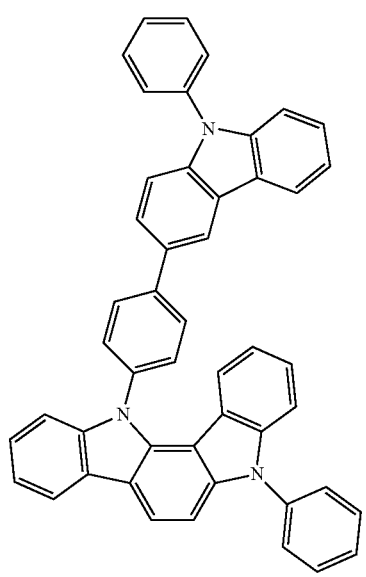
[D-85]
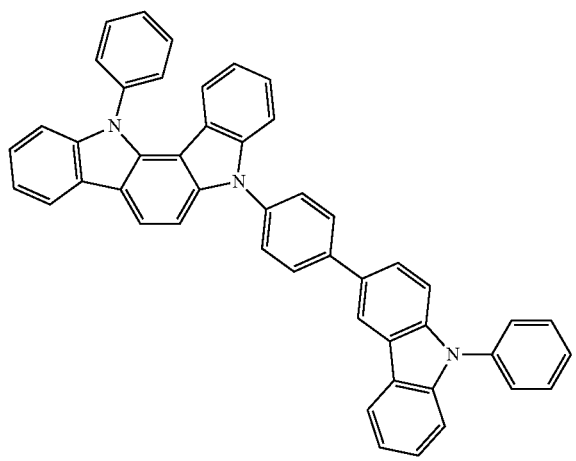
-continued
[D-86]
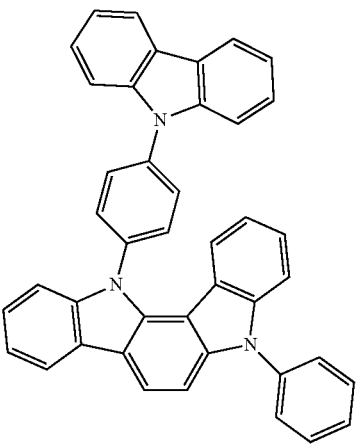
[D-87]
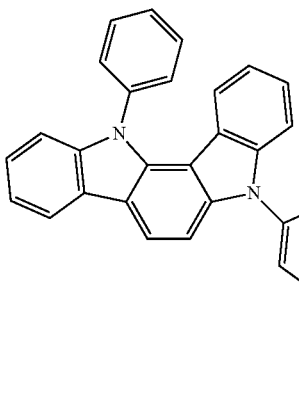
[D-88]
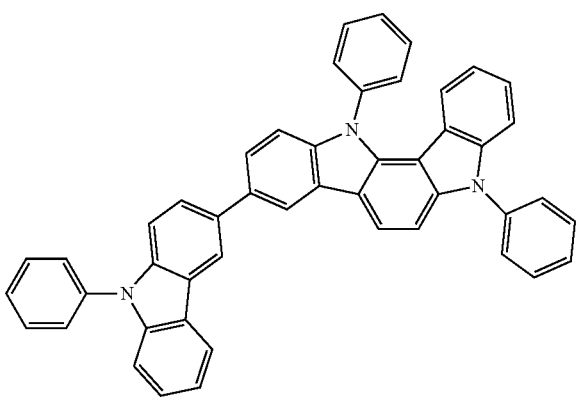

[D-89]
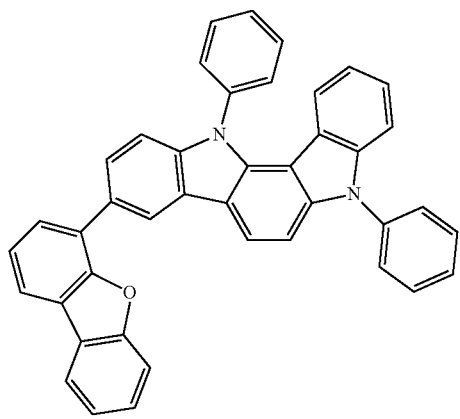
[D-90]
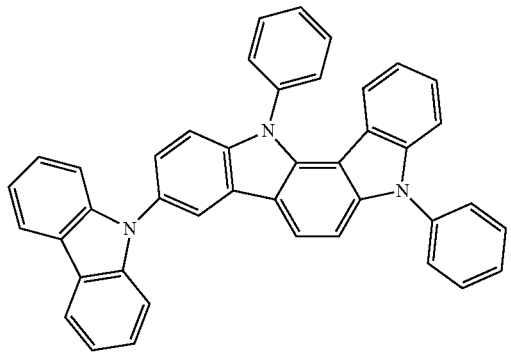
[D-91]
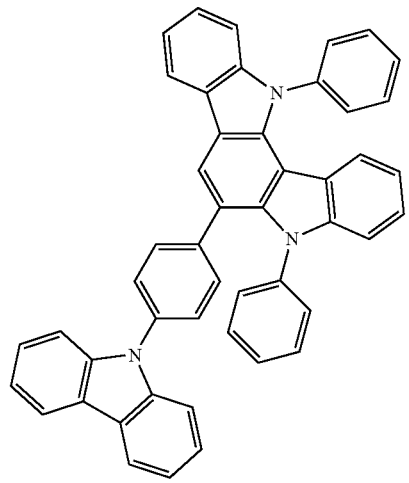
[D-92]
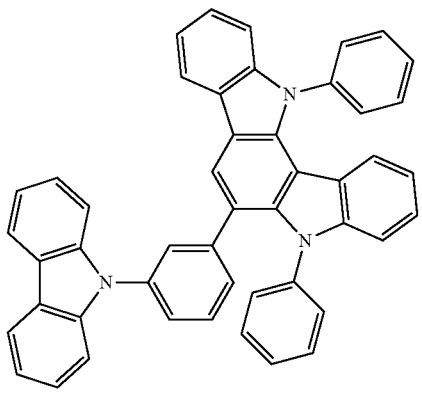
[D-93]
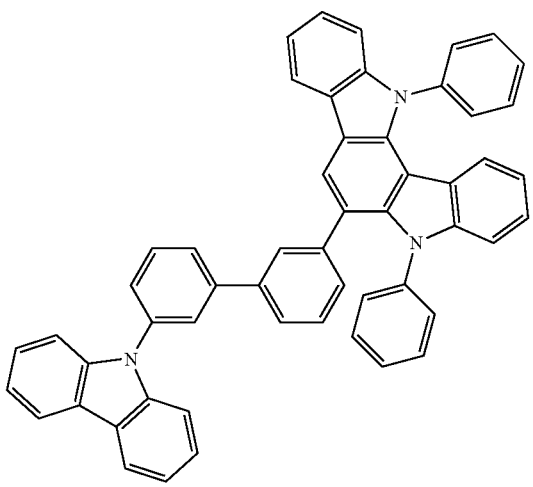
[D-94]
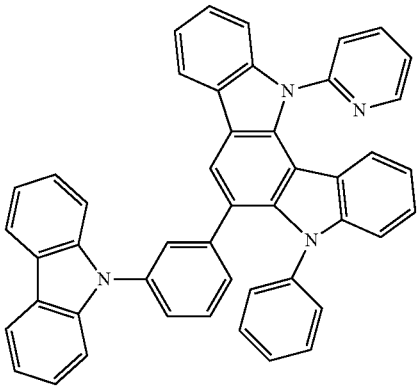

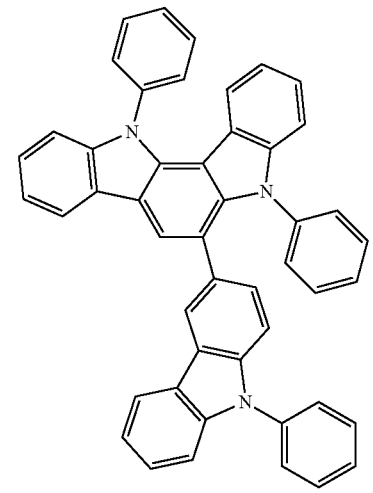
[D-95]

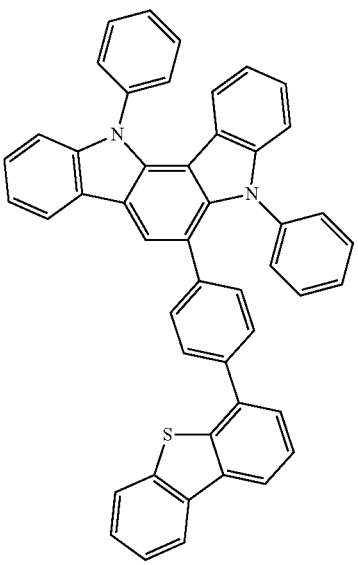
[D-98]

[D-96]

[D-97]

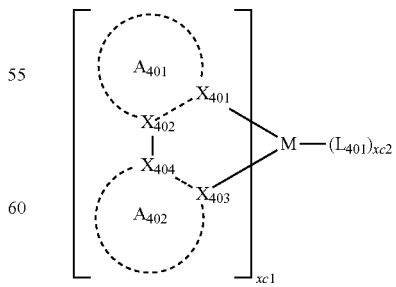

Indolocarbazole as a second host may be combined with the first host material to balance the first host material (the compound represented by Chemical Formula 1) having fast and stable electron transport characteristics and the second host material having fast and stable hole transport characteristics and thus to secure a low driving/long life-span host set having a high glass transition temperature relative to a molecular weight.

Simultaneously, the host set may be combined with a phosphorescent dopant that will be described later to secure a combination/matching advantage of packing of the host and dopant materials, an energy transport, and the like and thereby obtain characteristics of a low driving voltage, a long life-span, and high efficiency.

The first host and the second host in the present invention may be mixed with a known phosphorescent dopant that is an organometal compound including one of Ir, Pt, Os, Ti, Zr, Hf, Eu, Tb, Tm, Fe, Co, Ni, Ru, Rh, Pd, or a combination thereof or may be mixed with an organometal compound represented by Chemical Formula 401. However, these are exemplified, and a dopant that exhibit excellent effect by combining the composition of the first host and the second host according to the present invention is a dopant represented by Chemical Formula 8 that will be described later.

<Chemical Formula 401>

$$\left[ \begin{array}{c} A_{401} \\ X_{402} \\ X_{404} \\ A_{402} \end{array} \begin{array}{c} X_{401} \\ X_{403} \end{array} M-(L_{401})_{xc2} \right]_{xc1}$$

In Chemical Formula 401, M is selected from Ir, Pt, Os, Ti, Zr, Hf, Eu, Tb, and Tm; $X_{401}$ to $X_{404}$ are independently nitrogen or carbon; $A_{401}$ and $A_{402}$ rings are independently selected from a substituted or unsubstituted benzene, a substituted or unsubstituted naphthalene, a substituted or unsubstituted fluorene, a substituted or unsubstituted spirofluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; wherein "substituted" refers to replacement of at least one hydrogen of a substituent or a compound by deuterium, a halogen, a hydroxyl group, a cyano group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heterocyclic group, a C1 to C20 alkoxy group, a C1 to C10 trifluoroalkyl group, or a combination thereof; $L_{401}$ is an organic ligand; xc1 is 1, 2, or 3; and xc2 is 0, 1, 2, or 3.

$L_{401}$ may be any monovalent, divalent, or trivalent organic ligand. For example, $L_{401}$ may be selected from a halogen ligand (for example, Cl, F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, benzoate), a carbon monooxide ligand, an isonitrile ligand, a cyano ligand, and a phosphorus ligand (for example, phosphine, phosphite), but is not limited thereto.

When $A_{401}$ of Chemical Formula 401 has two or more substituents, they may be combined with two or more substituents of $A_{401}$ to form a saturated or unsaturated ring.

When $A_{402}$ of Chemical Formula 401 has two or more substituents, they may be combined with two or more substituents of $A_{402}$ to form a saturated or unsaturated ring.

When xc1 of Chemical Formula 401 is two or more, a plurality of ligands

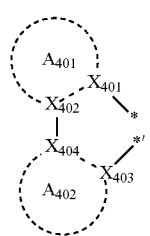

of Chemical Formula 401 may be the same or different. When xc1 of Chemical Formula 401 is two or more, $A_{401}$ and $A_{402}$ may be independently linked with $A_{401}$ and $A_{402}$ of adjacent other ligand directly or by a linking group (for example, a C1 to C5 alkylene group, —N(R')— (wherein, R' is a C1 to C10 alkyl group or a C6 to C20 aryl group), or —C(=O)—).

PD70

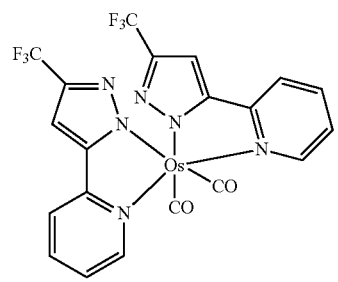

PD71

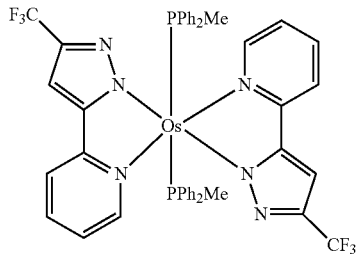

PD72

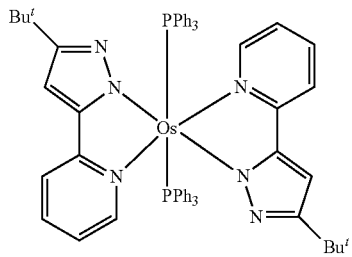

PD73

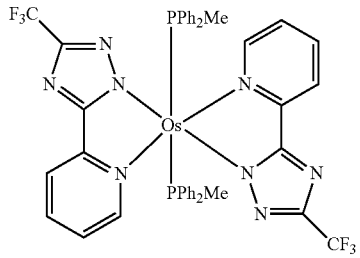

PD74

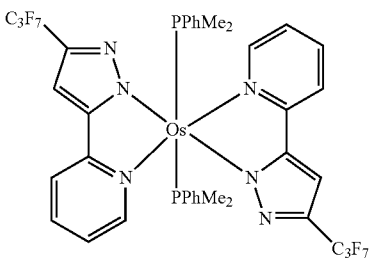

-continued

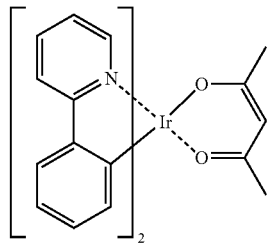
PD75

In other words, in an example embodiment of the present invention, an organometal compound represented by Chemical Formula 8 is used.

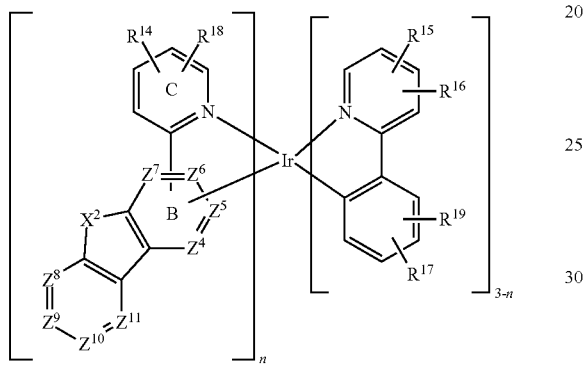
[Chemical Formula 8]

In Chemical Formula 8, $Z^4$ to $Z^{11}$ are independently N, C, or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is one of integers of 1 to 3.

The composition including the first and second hosts may be combined with the phosphorescent dopant including a dibenzofuranyl group, a dibenzothiophenyl group, or derivative groups thereof including at least one N to secure a combination/matching advantage of packing of host and dopant materials, an energy transport, and the like and thus to obtain characteristics of a low driving, a long life-span, and high efficiency.

In an example embodiment of the present invention, in Chemical Formula 8, one of $Z^4$ to $Z^{11}$ may be preferably N, and two, three, or four of $Z^4$ to $Z^{11}$ may be N.

The phosphorescent dopant may be for example represented by one of Chemical Formula 8-1 to Chemical Formula 8-6.

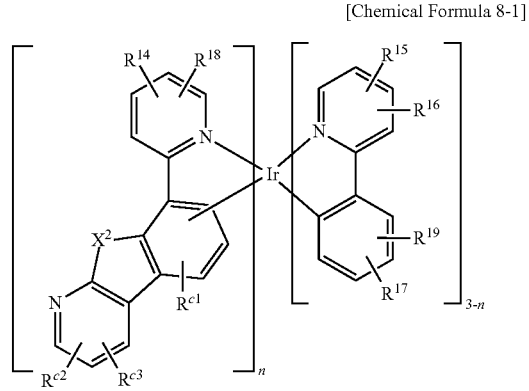
[Chemical Formula 8-1]

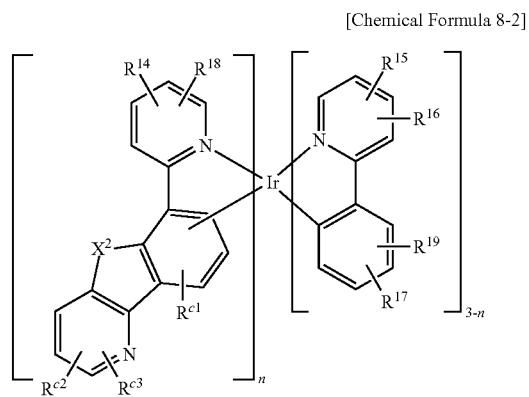
[Chemical Formula 8-2]

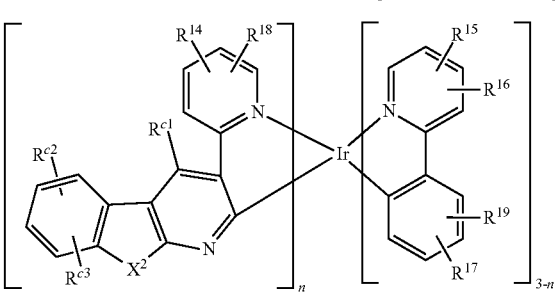
[Chemical Formula 8-3]

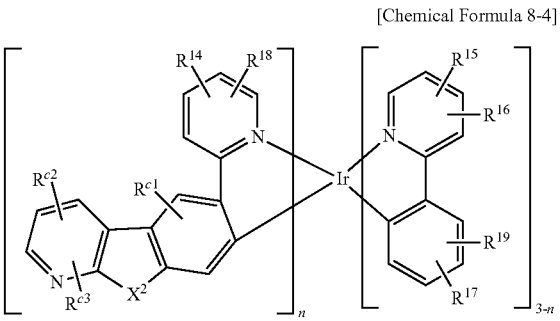
[Chemical Formula 8-4]

[Chemical Formula 8-5]

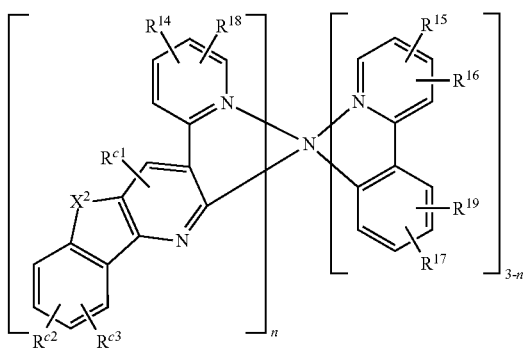

[Chemical Formula 8-6]

The phosphorescent dopant may be for example selected from compounds of Group 3, but is not limited thereto.

[Group 3]

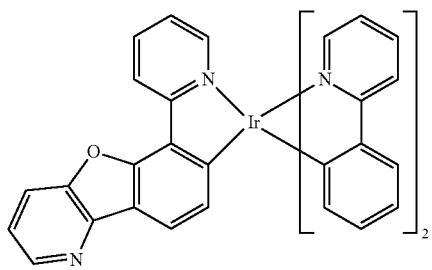

[E-1]

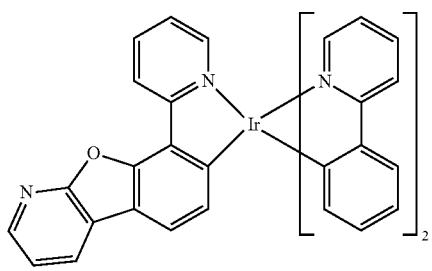

[E-2]

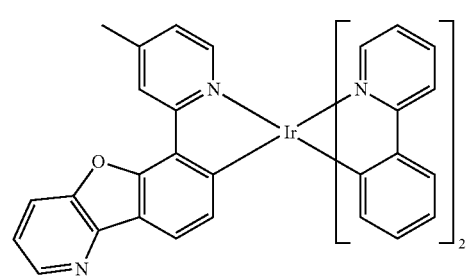

[E-3]

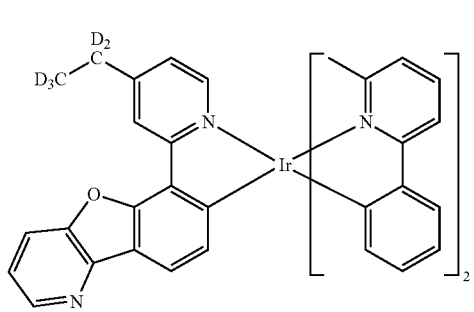

[E-4]

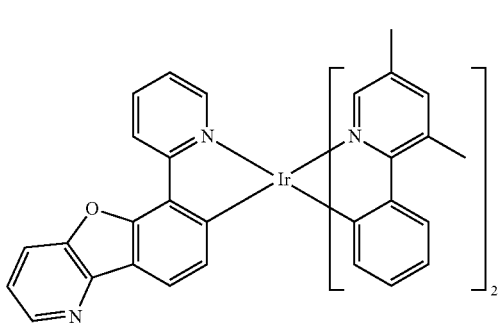

[E-5]

In Chemical Formula 8-1 to Chemical Formula 8-6, $X^2$, $R^{14}$ to $R^{17}$, and n are the same as described above, and $R^{c1}$, $R^{c2}$ and $R^{c3}$ are the same as $R^c$.

In a specific embodiment of the present invention, $R^c$, $R^{c1}$, $R^{c2}$, $R^{c3}$, and $R^{14}$ to $R^{17}$ may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C20 aryl group, for example $R^c$, $R^{c1}$, $R^{c2}$, $R^{c3}$, and $R^{14}$ to $R^{17}$ may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C12 aryl group, desirably $R^c$, $R^{c1}$, $R^{c2}$, $R^{c3}$, and $R^{14}$ to $R^{17}$ may independently be hydrogen, deuterium, a halogen, a silyl group that is substituted or unsubstituted with deuterium or a halogen, a methyl group that is substituted or unsubstituted with deuterium or a halogen, an isopropyl group that is substituted or unsubstituted with deuterium or a halogen, a tert-butyl group that is substituted or unsubstituted with deuterium or a halogen, or a silyl group that is substituted or unsubstituted with a C1 to C4 alkyl group.

[E-6]
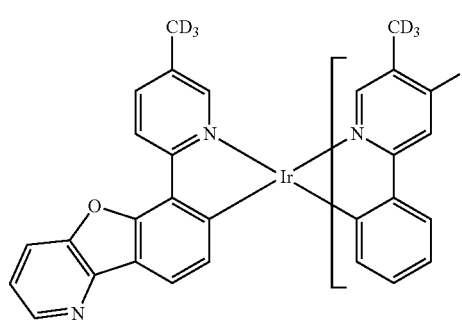
[E-7]
[E-8]
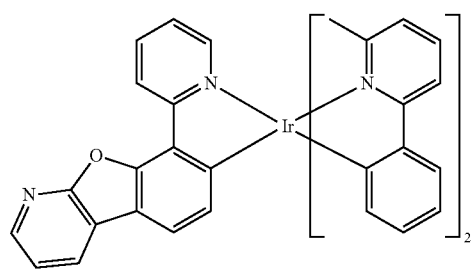
[E-9]
[E-10]
[E-11]
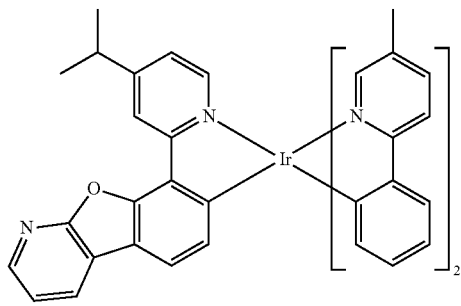
[E-12]
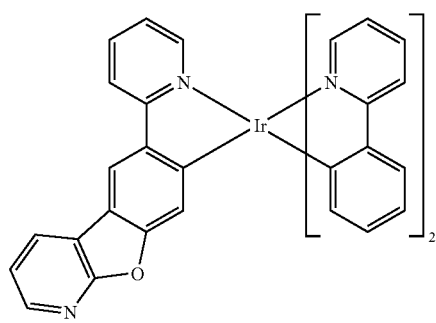
[E-13]
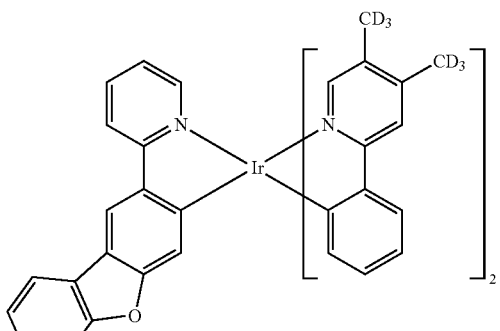
[E-14]
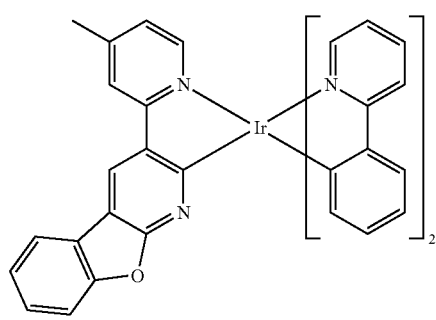

[E-15]
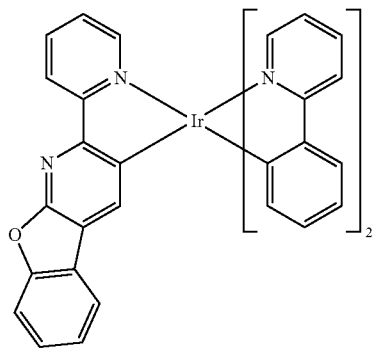
[E-16]
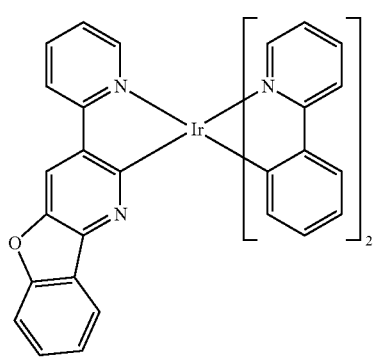
[E-17]
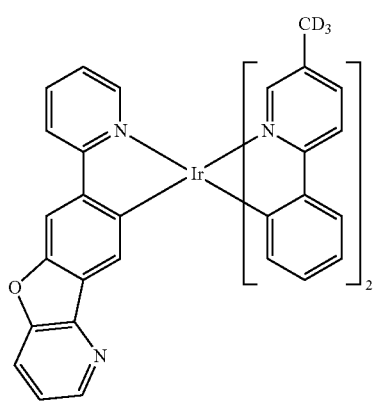
[E-18]
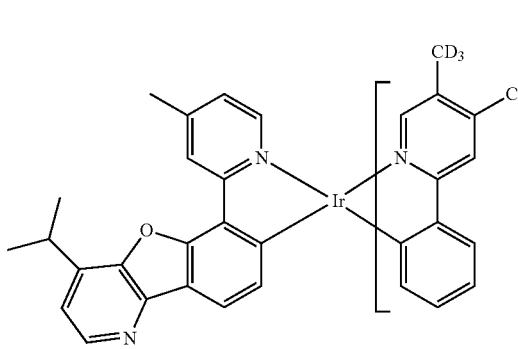
[E-19]
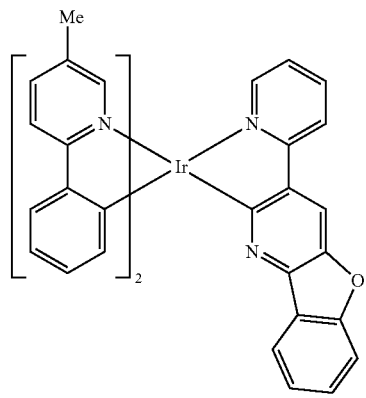
[E-20]
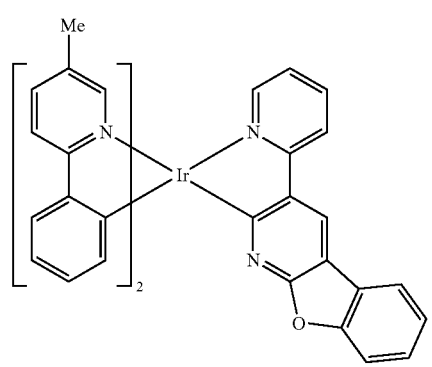
[E-21]
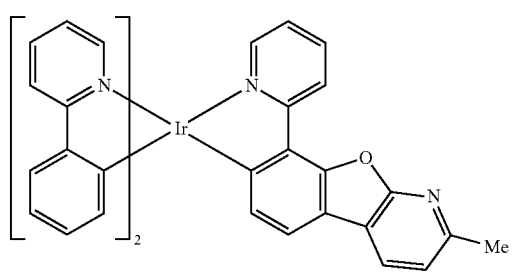
[E-22]
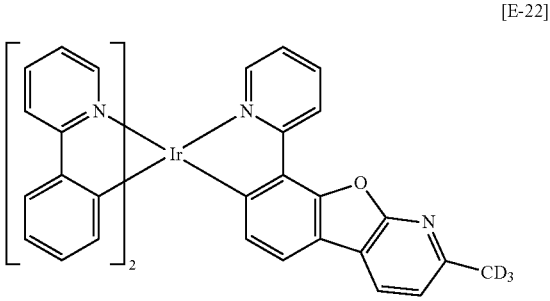

[E-23]
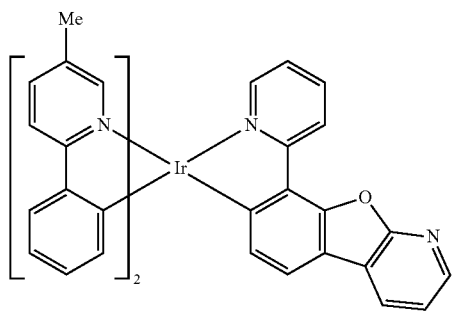
[E-27]
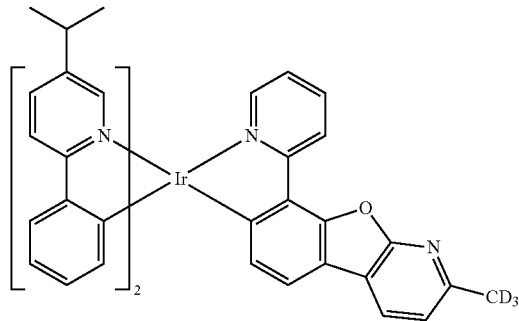
[E-24]
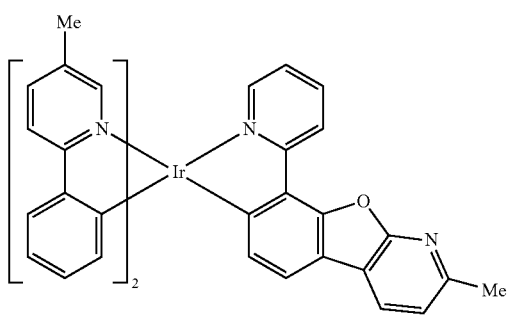
[E-28]
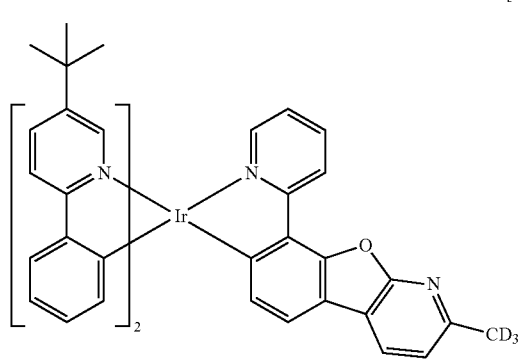
[E-25]
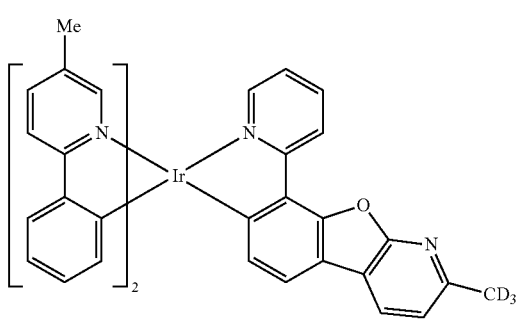
[E-29]
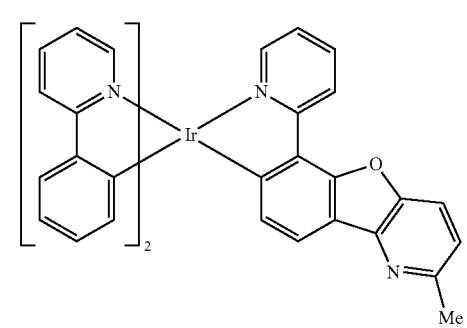
[E-26]
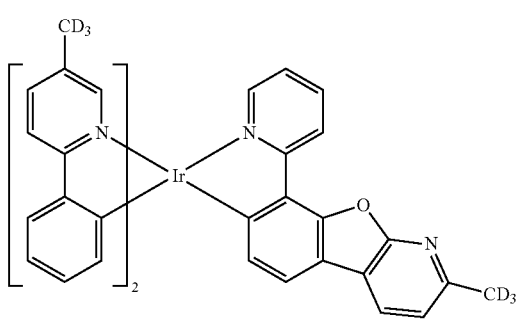
[E-30]
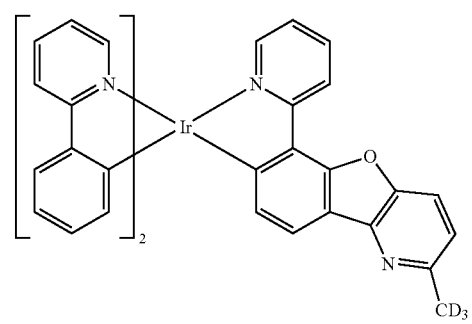

[E-31]
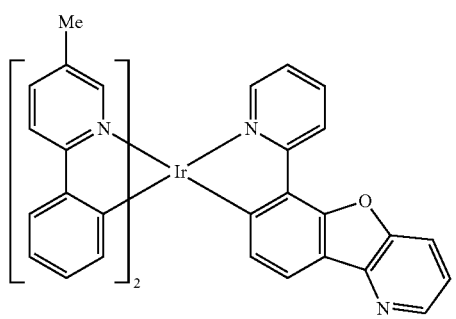
[E-35]
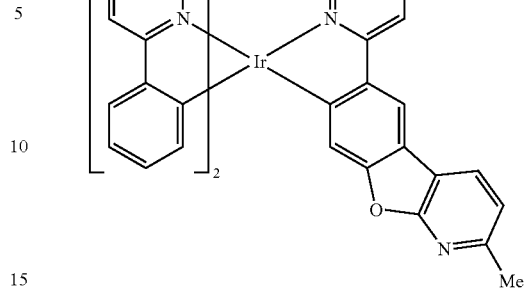
[E-32]
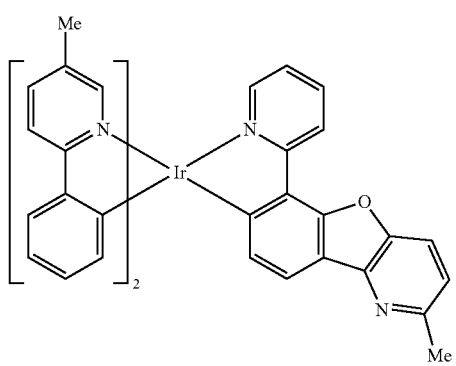
[E-36]
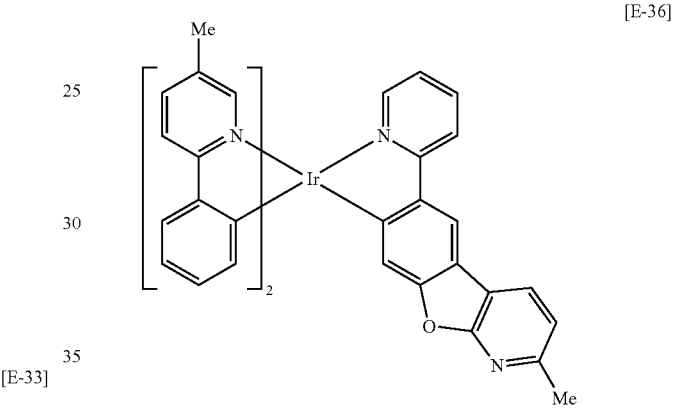
[E-33]
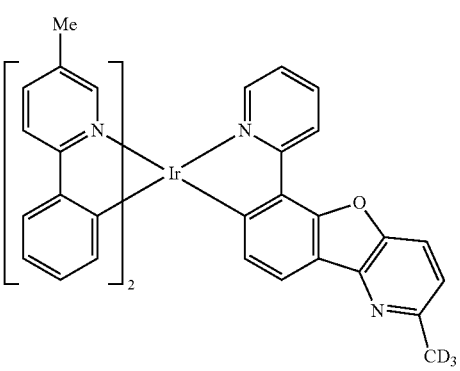
[E-37]
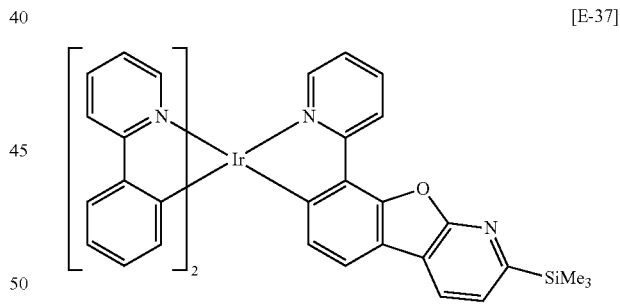
[E-34]
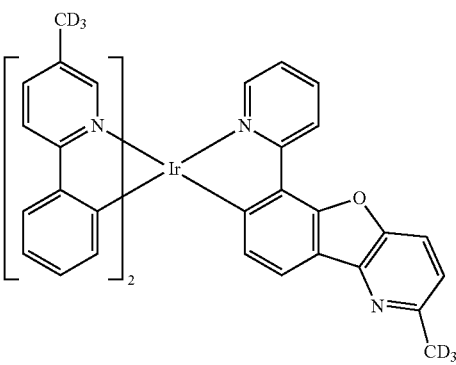
[E-38]
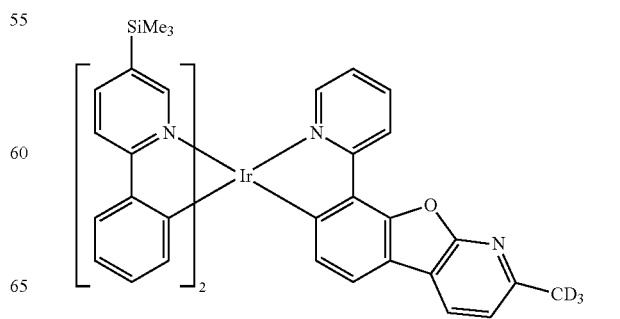

-continued

[E-39]

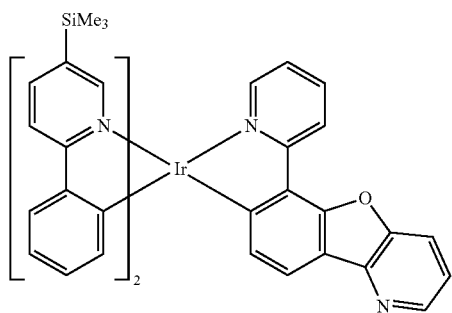

[E-40]

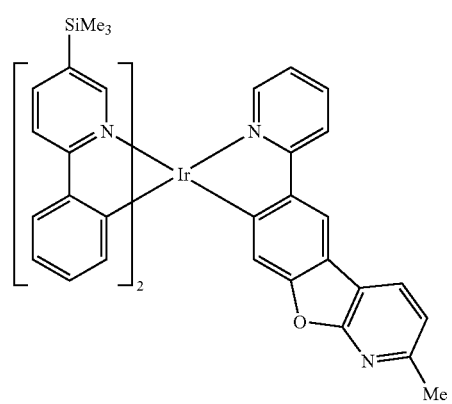

More specifically, the first host and the second host may be included in a weight ratio of 1:9 to 6:4, 2:8 to 6:4, 3:7 to 6:4, more preferably, the first host and the second host may be included in a weight ratio of 1:9 to 5:5, 2:8 to 5:5, 3:7 to 5:5, and the most preferably the first host and the second host may be included in a weight ratio of 4:6 to 5:5.

The phosphorescent dopant may be included in an amount of about 0.1 wt % to 15 wt %, preferably 1 wt % to 15 wt %, and more preferably 5 wt % to 15 wt % based on 100 wt % of the composition of the first host and second host. For example, the first host and the second host may be included in a weight ratio of 3:7 and the phosphorescent dopant may be included in an amount of 5 wt % to 15 wt % based on 100 wt % of the composition of the first host and second host.

The organic light emitting diode may be applied to a display device, for example an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there are no particular descriptions or were synthesized by known methods.

The compound as one specific examples of the present invention was synthesized through the following steps.

(Preparation of First Host)

Synthesis Example 1: Synthesis of Intermediate 1

[Reaction Scheme]

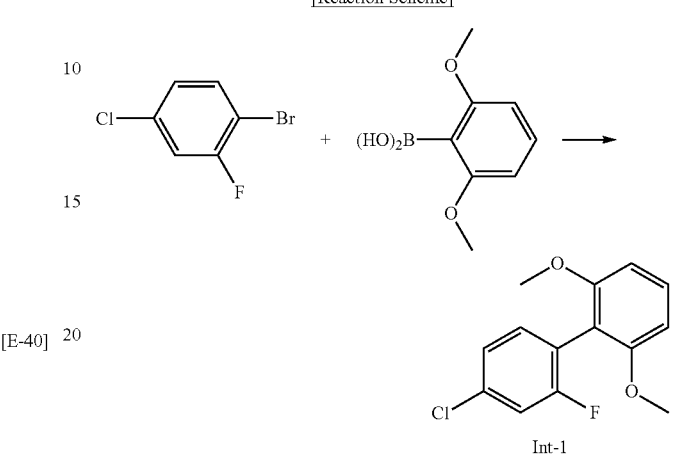

1-Bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were put in a round-bottomed flask and then dissolved in 500 ml of THF and 200 ml of distilled water, and the solution was refluxed and stirred at 60° C. for 12 hours. When a reaction was complete, an aqueous layer was removed therefrom, and 38 g (51%) of Intermediate (Int-1) was obtained through column chromatography (hexane: DCM (20%)).

Synthesis Example 2: Synthesis of Intermediate 2

[Reaction Scheme]

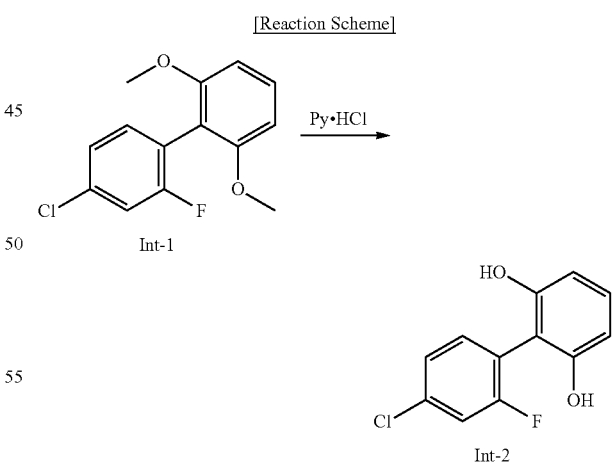

Intermediate (Int-1) (38 g, 142 mmol) and pyridine hydrochloride (165 g, 1425 mmol) were put in a round-bottomed flask and then, refluxed and stirred at 200° C. for 24 hours. When a reaction was complete, the resultants were cooled down to room temperature and then, slowly poured into distilled water, and the mixture was stirred for 1 hour. A solid was filtered therefrom to obtain 23 g (68%) of an intermediate (Int-2).

Synthesis Example 3: Synthesis of Intermediate 3

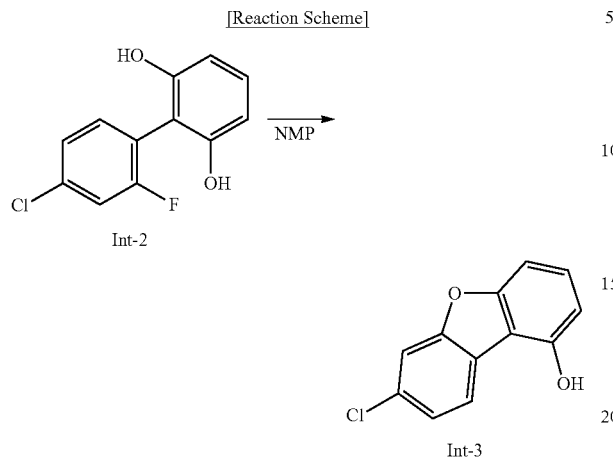

Intermediate (Int-2) (23 g, 96 mmol) and K₂CO₃ (20 g, 144 mmol) were put in a round-bottomed flask and then, dissolved in 100 ml of NMP, and the solution was refluxed and stirred at 180° C. for 12 hours. When a reaction was complete, the mixture was poured into an excessive amount of distilled water. A solid therein was filtered, dissolved in ethylacetate, and dried with MgSO₄, and an organic layer was removed therefrom under a reduced pressure. 16 g (76%) of Intermediate (Int-3) was obtained through column chromatography (Hexane:Ethyl Acetate (30%)).

Synthesis Example 4: Synthesis of Intermediate 4

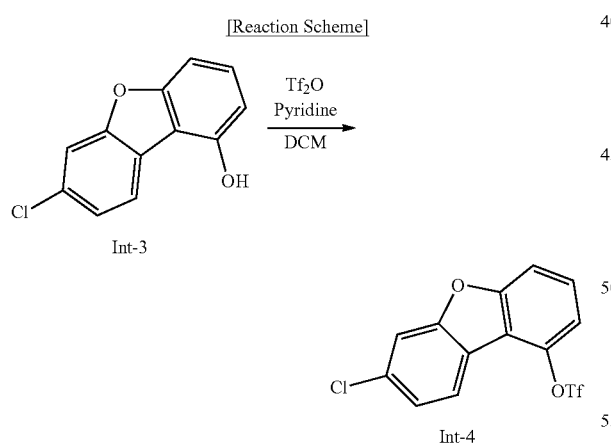

Intermediate (Int-3) (16 g, 73 mmol) and pyridine (12 ml, 146 mmol) were put in a round-bottomed flask and dissolved in 200 ml of DCM. A temperature of the solution was cooled down to 0° C., and trifluoromethane sulfonic anhydride (14.7 ml, 88 mmol) was slowly added thereto in a dropwise fashion. After stirring the mixture for 6 hours, when a reaction was complete, an excessive amount of distilled water was added thereto, and the mixture was stirred for 30 minutes and extracted with DCM. An organic solvent was removed therefrom under a reduced pressure, and a resultant was vacuum-dried to obtain 22.5 g (88%) of Intermediate (Int-4).

Synthesis Example 5: Synthesis of Intermediate 5

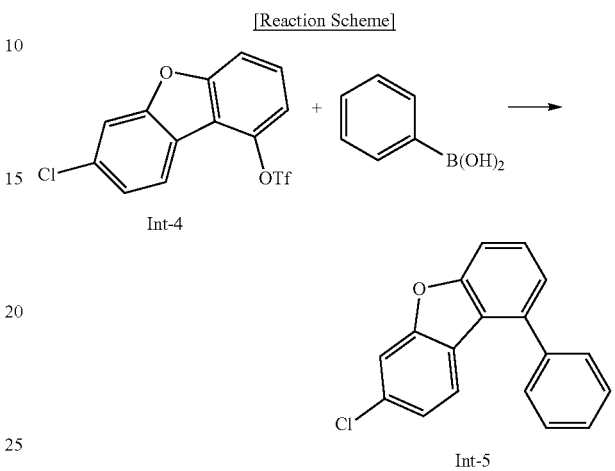

14.4 g (81%) of Intermediate (Int-5) was synthesized according to the same method as Synthesis Example 1 by using Intermediate (Int-4) (22.5 g, 64 mmol), phenylboronic acid (7.8 g, 64 mmol), K₂CO₃ (13.3 g, 96 mmol), and Pd(PPh₃)₄ (3.7 g, 3.2 mmol).

Synthesis Example 6: Synthesis of Intermediate 6

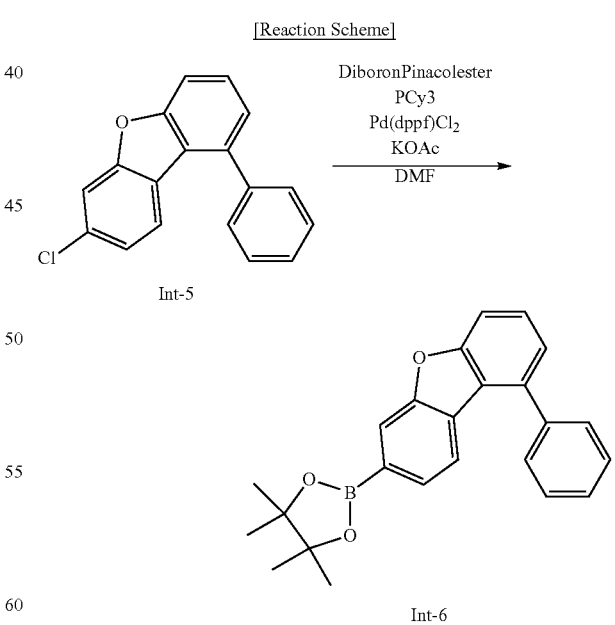

Intermediate (Int-5) (22.5 g, 80 mmol), bis(pinacolato) diboron (24.6 g, 97 mmol), Pd(dppf)Cl₂ (2 g, 2.4 mmol), tricyclohexylphosphine (3.9 g, 16 mmol), and potassium acetate (16 g, 161 mmol) were put in a round-bottomed flask and dissolved in 320 ml of DMF. The mixture is refluxed and stirred at 120° C. for 10 hours. When a reaction was complete, the resultant was poured into an excessive amount of distilled water, and the obtained mixture was stirred for one hour. A solid therein was filtered and dissolved in DCM. After removing moisture therefrom with MgSO₄, an organic solvent was filtered therefrom by using a silica gel pad and then, removed under a reduced pressure. A solid therein was recrystallized by using ethyl acetate and hexane to obtain 26.9 g (90%) of Intermediate (Int-6).

Synthesis Example 7: Synthesis of Intermediate 7

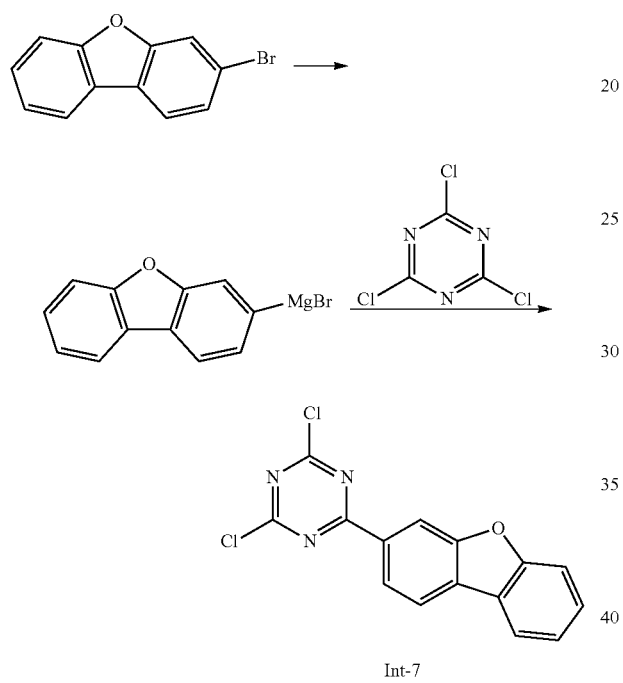

Int-7

Synthesis Example 8: Synthesis of Intermediate 8

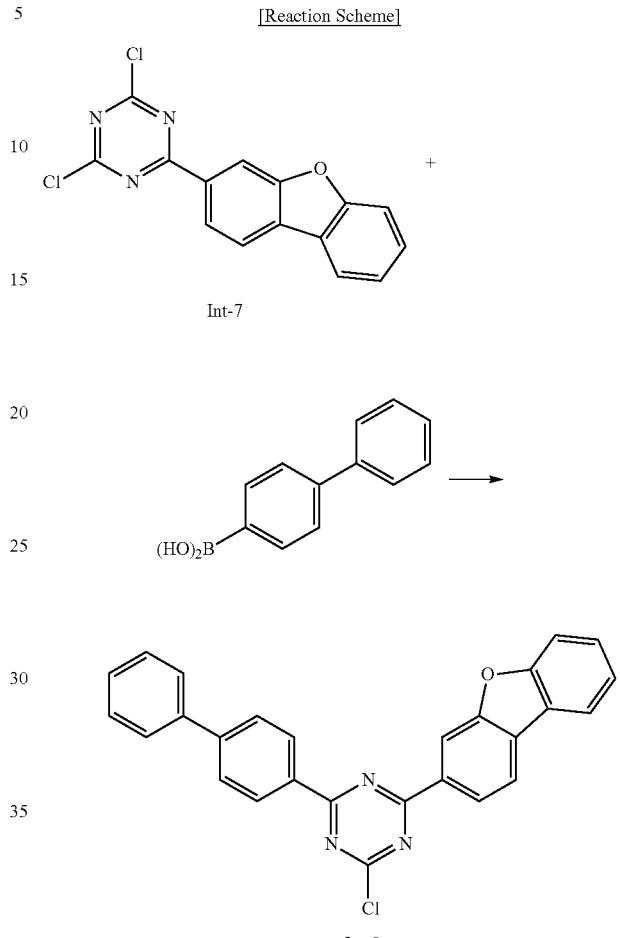

Int-8

Mg (4.9 g, 202 mmol) was put in a round-bottomed flask under a nitrogen condition and heated by a heat gun. When moderately cooled down, Iodine (0.5 g, 2 mmol) was added thereto, then, 30 ml of THF was added thereto, and the obtained mixture was stirred. 3-Bromodibenzofuran (50 g, 202 mmol) dissolved in 100 ml of THF was put in a dropping funnel and then, slowly added in a dropwise fashion to the round-bottomed flask. The mixed solution was stirred when it started to become transparent and hot until completely transparent. In a new round-bottomed flask, cyanuric chloride (37.3 g, 202 mmol) was dissolved in 200 ml of THF and put under an ice bath condition. Subsequently, a Grignard reagent prepared in advance was slowly added thereto in a dropwise fashion. After additionally stirring the mixture for 1 hour, distilled water was added thereto to complete a reaction. An organic layer was separated therefrom, and a solvent was removed therefrom under a reduced pressure. Then, a small amount of DCM was added thereto to dissolve it, the solution was added in a dropwise fashion to an excessive amount of methanol, and a solid precipitated therein was filtered to obtain 38 g (60%) of Intermediate (Int-7).

15.1 g (58%) of intermediate (Int-8) was obtained according to the same method as Synthesis Example 1 by synthesizing Intermediate (Int-7) (19 g, 60 mmol), 4-biphenylboronic acid (11.9 g, 60 mmol), K₂CO₃ (12.5 g, 90 mmol), and Pd(PPh₃)₄ (3.5 g, 3 mmol) in a round-bottomed flask under a nitrogen condition.

Synthesis Example 9: Synthesis of Intermediate 9

[Reaction Scheme]

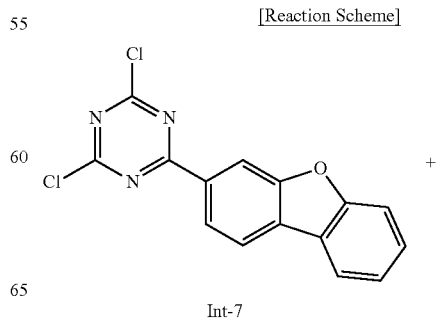

Int-7

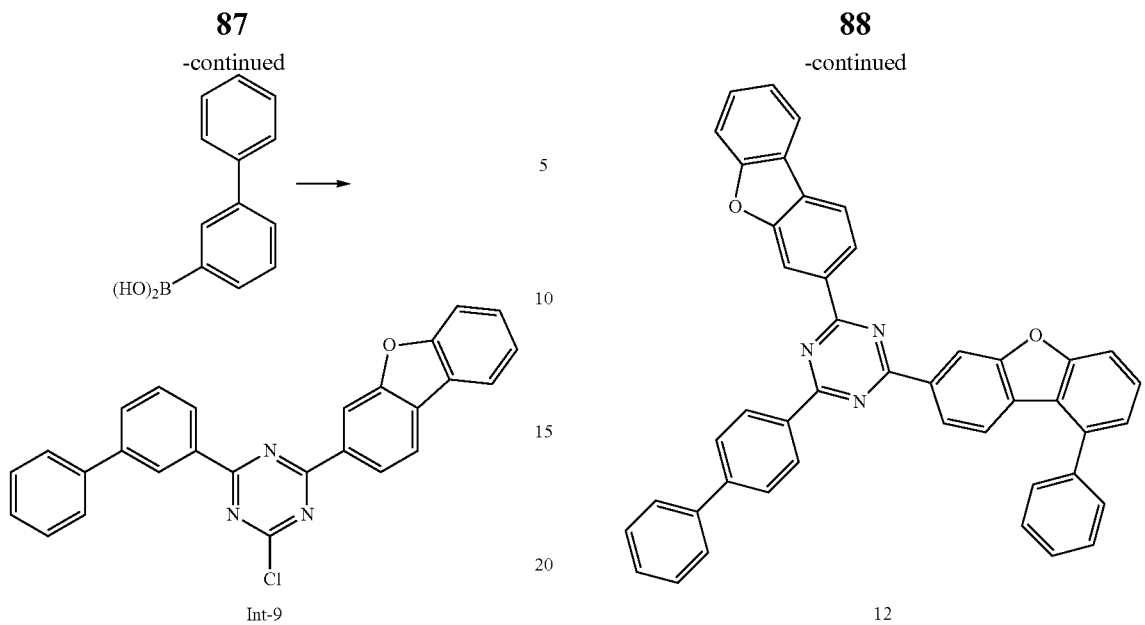

15.9 g (61%) of Intermediate (Int-9) was obtained according to the same method as Synthesis Example 1 by synthesizing Intermediate (Int-7) (19 g, 60 mmol), 3-biphenylboronic acid (11.9 g, 60 mmol), $K_2CO_3$ (12.5 g, 90 mmol), and $Pd(PPh_3)_4$ (3.5 g, 3 mmol) in a round-bottomed flask under a nitrogen condition.

Synthesis Example 10: Synthesis of Compound 12

15.5 g (70%) of Compound 12 was obtained according to the same method as Synthesis Example 1 by synthesizing Intermediate (Int-8) (15 g, 35 mmol), Intermediate (Int-6) (12.8 g, 35 mmol), $K_2CO_3$ (7.2 g, 52 mmol), and $Pd(PPh_3)_4$ (2 g, 1.7 mmol) in a round-bottomed flask under a nitrogen condition. LC/MS calculated for: $C_{45}H_{27}N_3O_2$ Exact Mass: 641.21. found for: 642.64.

Synthesis Example 11: Synthesis of Compound 16

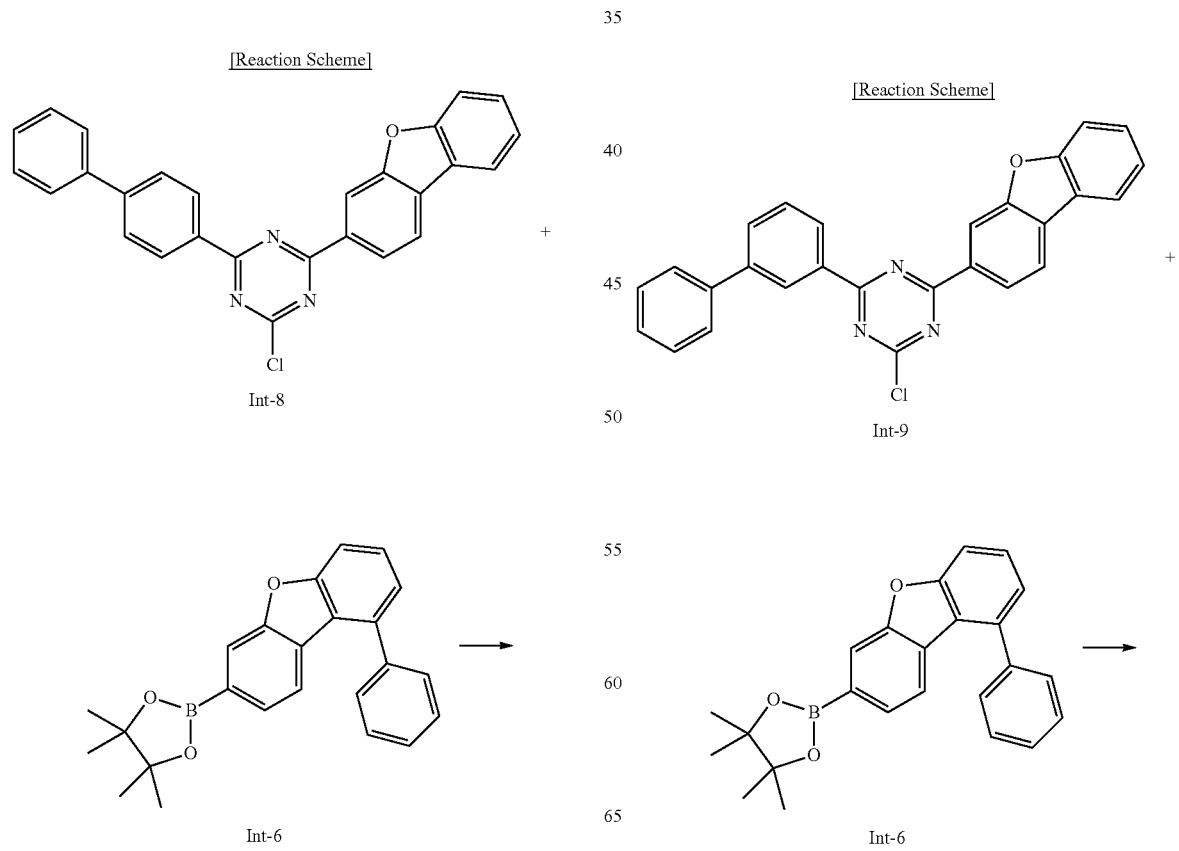

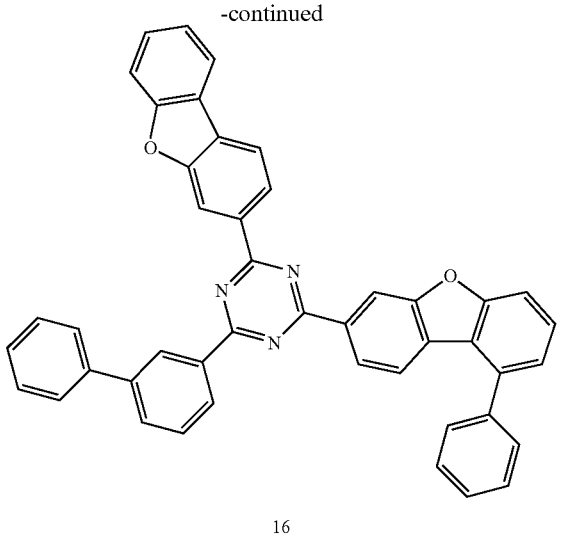

16

18.8 g (80%) of Compound 12 was obtained according to the same method as Synthesis Example 1 by synthesizing Intermediate (Int-9) (15.9 g, 37 mmol), Intermediate (Int-6) (15 g, 40 mmol), $K_2CO_3$ (7.6 g, 55 mmol), and $Pd(PPh_3)_4$ (2.1 g, 1.8 mmol) in a round-bottomed flask under a nitrogen condition. LC/MS calculated for: $C_{45}H_{27}N_3O_2$ Exact Mass: 641.21. found for: 642.16.

Synthesis Example 12: Synthesis of Intermediate 10

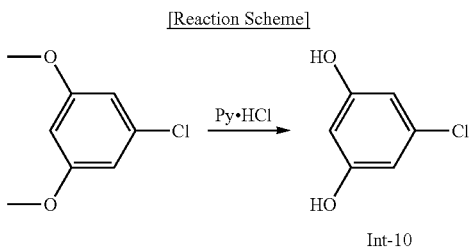

1-Chloro-3,5-dimethoxybenzene (70 g, 406 mmol) and pyridine hydrochloride (468 g, 4055 mmol) were put in a round-bottomed flask and then, refluxed and stirred at 200° C. for 24 hours. When a reaction was complete, the resultants were cooled down to room temperature and then, slowly poured into distilled water, and the mixture was stirred for 1 hour. A solid therein was filtered to obtain 51.6 g (88%) of Intermediate (Int-10).

Synthesis Example 13: Synthesis of Intermediate 11

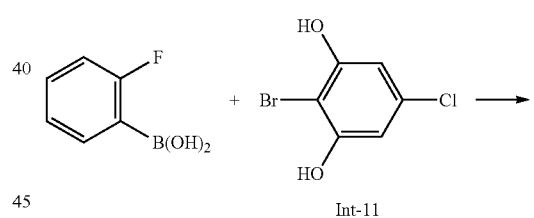

Intermediate (Int-10) (51.6 g, 357 mmol) and p-toluenesulfonic acid monohydrate (6.8 g, 36 mmol) were put in a round-bottomed flask and dissolved in 500 ml of methanol. Subsequently, NBS (63.5 g, 357 mmol) was dissolved in 1 L of methanol, and the solution was slowly added thereto in a dropwise fashion at 0° C. for 30 minutes. After stirring the mixture for 1 hour at room temperature, when a reaction was complete, a sodium thiosulfate-saturated solution was added thereto, and the obtained mixture was stirred. DCM was added thereto for an extraction, and a solvent was removed therefrom under a reduced pressure. A product therein was separated through flash column chromatography to obtain 72 g (90%) of Intermediate (Int-11).

Synthesis Example 14: Synthesis of Intermediate 12

34.5 g (45%) of Intermediate (Int-12) was obtained according to the same method as Synthesis Example 1 by using 2-fluorophenylboronic acid (45 g, 322 mmol), Intermediate (Int-11) (72 g, 322 mmol), $K_2CO_3$ (97.8 g, 708 mmol), and $Pd(PPh_3)_4$ (11.2 g, 9.7 mmol) in a round-bottomed flask under a nitrogen condition.

Synthesis Example 15: Synthesis of Intermediate 13

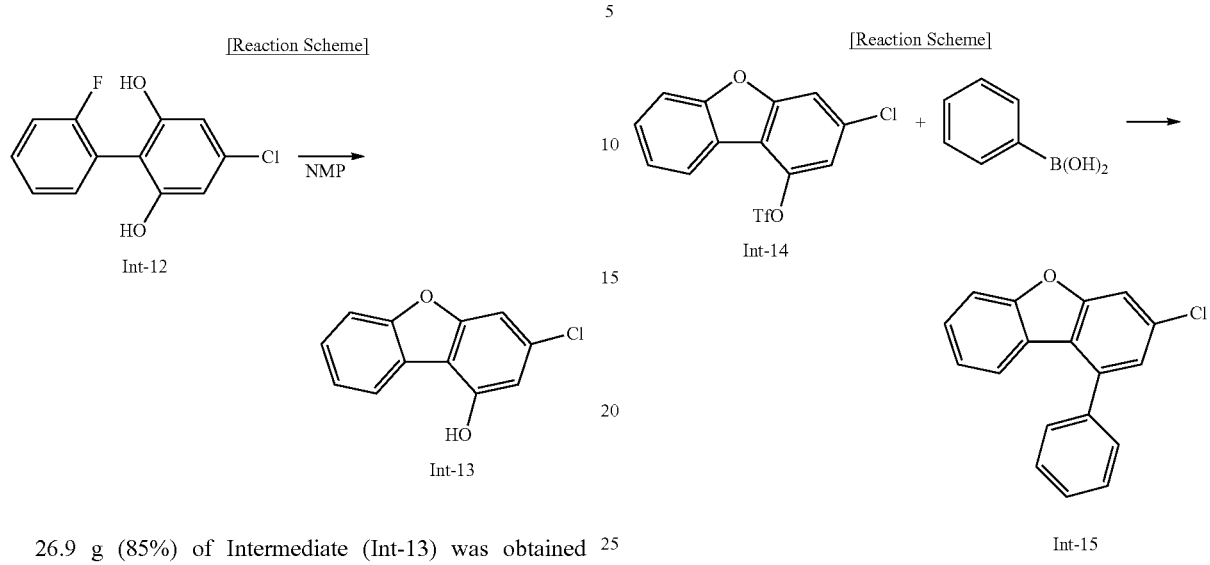

26.9 g (85%) of Intermediate (Int-13) was obtained according to the same method as Synthesis Example 3 by putting Intermediate (Int-12) (34.5 g, 145 mmol) and $K_2CO_3$ (26 g, 188 mmol) in a round-bottomed flask and dissolving them in 450 ml of NMP.

Synthesis Example 16: Synthesis of Intermediate 14

[Reaction Scheme]

Intermediate (Int-13) (26.9 g, 123 mmol) and pyridine (20 ml, 246 mmol) were put in a round-bottomed flask and dissolved in 300 ml of DCM. After cooled down to 0° C., trifluoromethane sulfonic anhydride (24.7 ml, 148 mmol) was slowly added thereto in a dropwise fashion. The obtained mixture was stirred for 6 hours, when a reaction was complete, an excessive amount of distilled water was added thereto, and the obtained mixture was stirred for 30 minutes and extracted with DCM. After removing an organic solvent therefrom under a reduced pressure, an extract therein was vacuum-dried to obtain 36.2 g (84%) of Intermediate (Int-14).

Synthesis Example 17: Synthesis of Intermediate 15

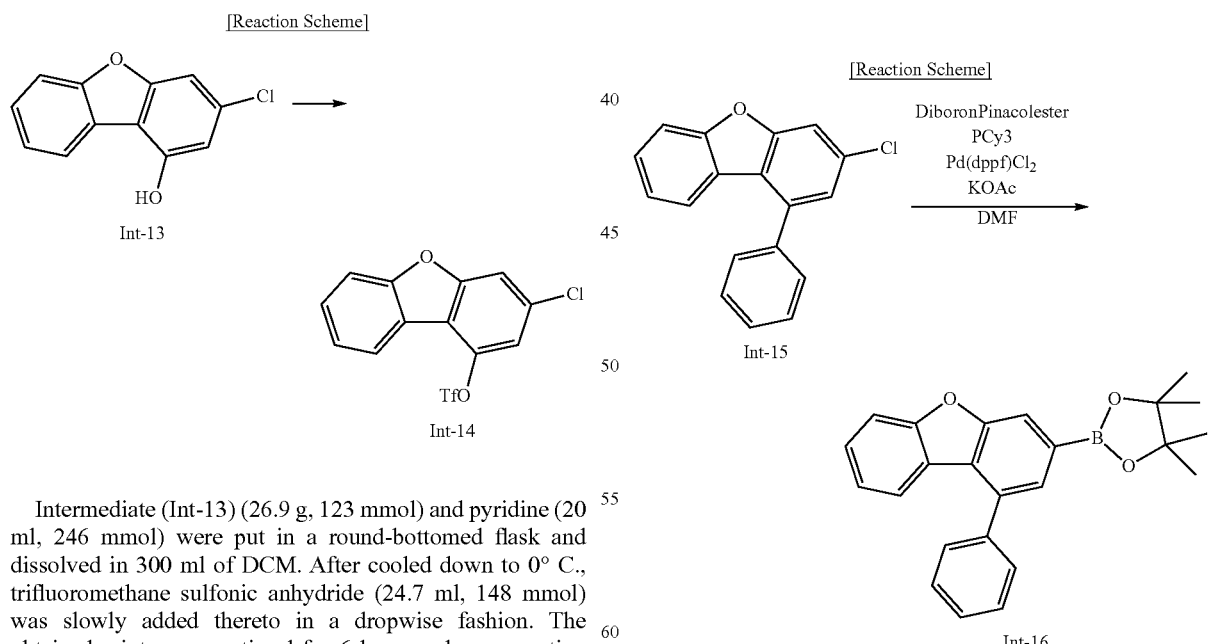

25.9 g (90%) of Intermediate (Int-15) was obtained according to the same method as Synthesis Example 1 by using Intermediate (Int-14) (36.2 g, 103 mmol), phenylboronic acid (12.6 g, 103 mmol), $K_2CO_3$ (21.4 g, 155 mmol), and $Pd(PPh_3)_4$ (5.9 g, 5 mmol).

Synthesis Example 18: Synthesis of Intermediate 16

[Reaction Scheme]

25.8 g (75%) of Intermediate (Int-16) was obtained according to the same method as Synthesis Example 6 by using Intermediate (Int-15) (25.9 g, 93 mmol), bis(pinacolato)diboron (28.3 g, 112 mmol), $Pd(dppf)Cl_2$ (2.3 g, 2.8 mmol), tricyclohexylphosphine (4.5 g, 18.6 mmol), and potassium acetate (18.2 g, 186 mmol) in a round-bottomed flask and dissolving them in 350 ml of DMF.

Synthesis Example 19: Synthesis of Compound 9

[Reaction Scheme]

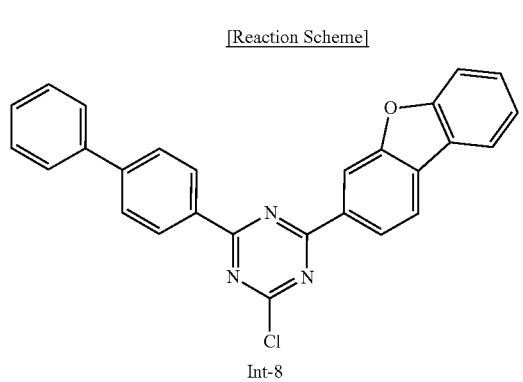
Int-8

+

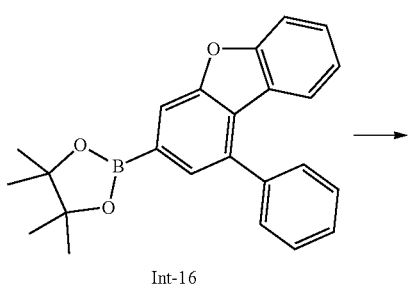
Int-16

→

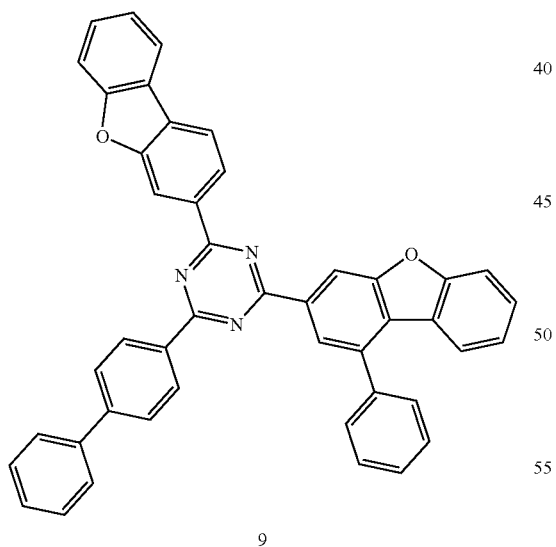
9

20.2 g (77%) of Compound 9 was obtained according to the same method as Synthesis Example 1 by using Intermediate (Int-8) (12 g, 28 mmol), Intermediate (Int-16) (11 g, 30 mmol), $K_2CO_3$ (5.7 g, 41 mmol), and Pd(PPh$_3$)$_4$ (1.6 g, 1.4 mmol) in a round-bottomed flask under a nitrogen condition. LC/MS calculated for: $C_{45}H_{27}N_3O_2$ Exact Mass: 641.21. found for: 642.31.

Synthesis Example 20: Synthesis of Compound 33

[Reaction Scheme]

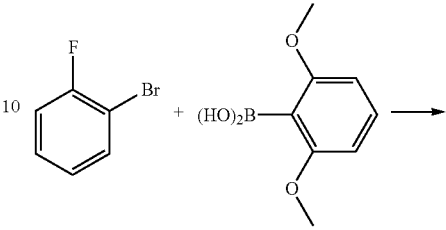

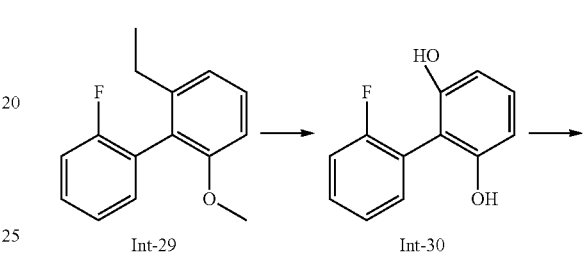
Int-29    Int-30

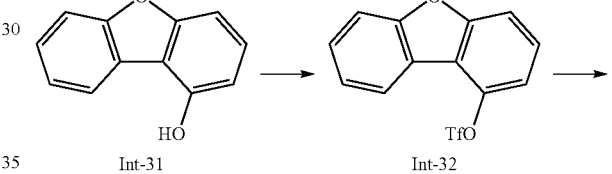
Int-31    Int-32

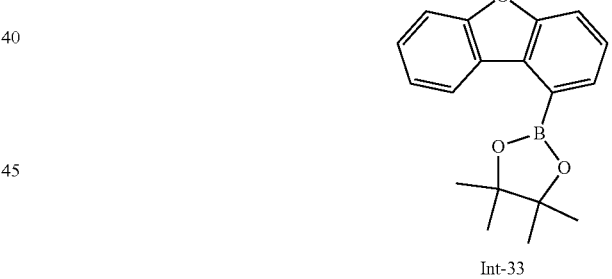
Int-33

27.4 g (38%) of intermediate (Int-32) was obtained according to the same method as Synthesis Example 1 to Synthesis Example 4 by using 1-bromo-2-fluorobenzene (42 g, 240 mmol) instead of 1-bromo-4-chloro-2-fluorobenzene to synthesize Intermediates (Int-29 to Int-32).

Intermediate (Int-32) (27.4 g, 86.6 mmol), bis(pinacolato) diboron (26.4 g, 104 mmol), Pd(dppf)Cl$_2$ (2.2 g, 2.6 mmol), and potassium acetate (12.8 g, 130 mmol) were dissolved in toluene (350 ml) in a round-bottomed flask under a nitrogen condition, and the mixed solution was stirred under reflux at 120° C. condition for 15 hours. When a reaction was complete, the resultant was filtered with Celite to remove a solid therefrom, and 1 L of hot toluene was poured thereinto. The filtered solution was removed under a reduced pressure, and was recrystallized with ethyl acetate to obtain 11.5 g (45%) of intermediate (Int-33).

[Reaction Scheme]

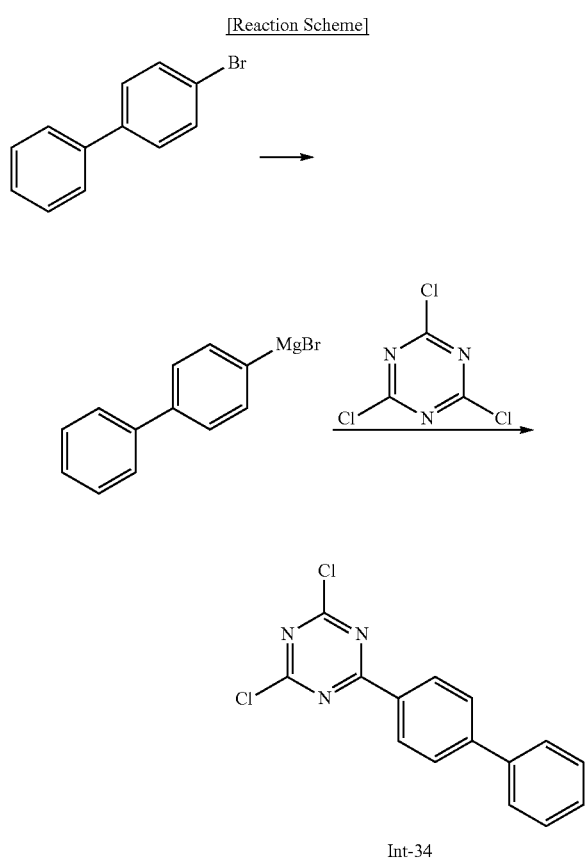

Int-34

24.5 g (63%) of intermediate (Int-34) was obtained according to the same method as Synthesis Example 7 by using 4-bromobiphenyl (30 g, 128.7 mmol) instead of 3-bromodibenzofuran.

[Reaction Scheme]

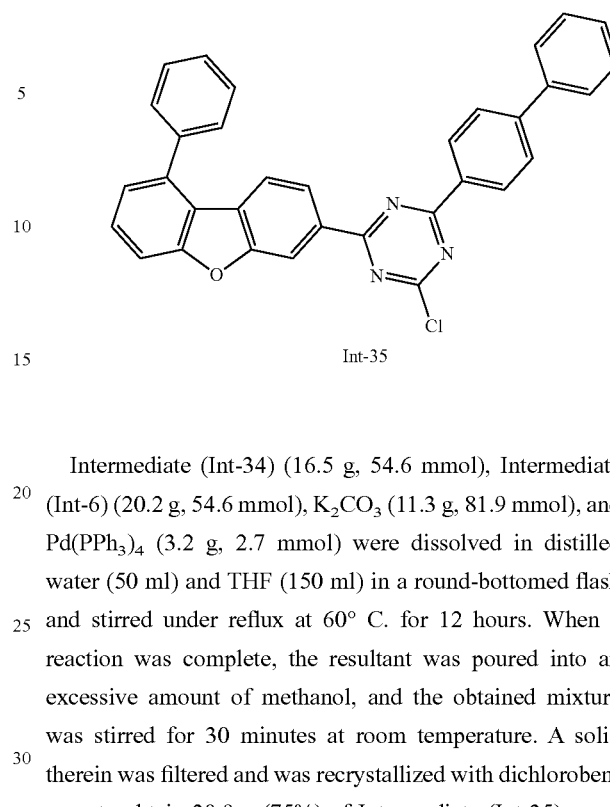

Int-35

Intermediate (Int-34) (16.5 g, 54.6 mmol), Intermediate (Int-6) (20.2 g, 54.6 mmol), $K_2CO_3$ (11.3 g, 81.9 mmol), and $Pd(PPh_3)_4$ (3.2 g, 2.7 mmol) were dissolved in distilled water (50 ml) and THF (150 ml) in a round-bottomed flask and stirred under reflux at 60° C. for 12 hours. When a reaction was complete, the resultant was poured into an excessive amount of methanol, and the obtained mixture was stirred for 30 minutes at room temperature. A solid therein was filtered and was recrystallized with dichlorobenzene to obtain 20.9 g (75%) of Intermediate (Int-35).

[Reaction Scheme]

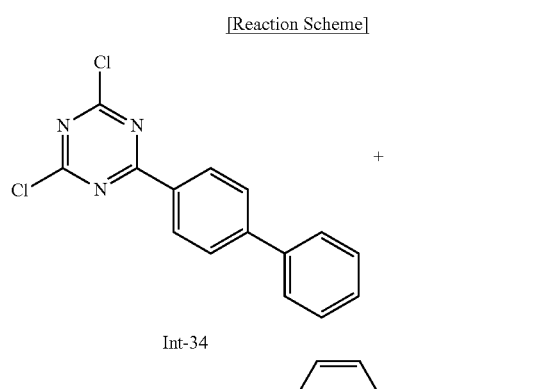

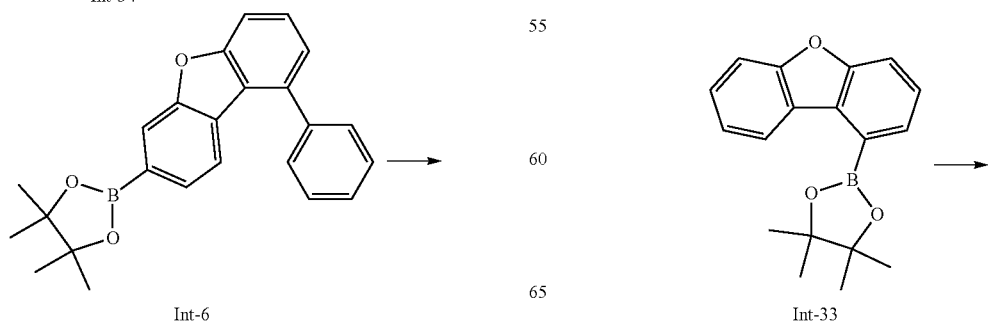

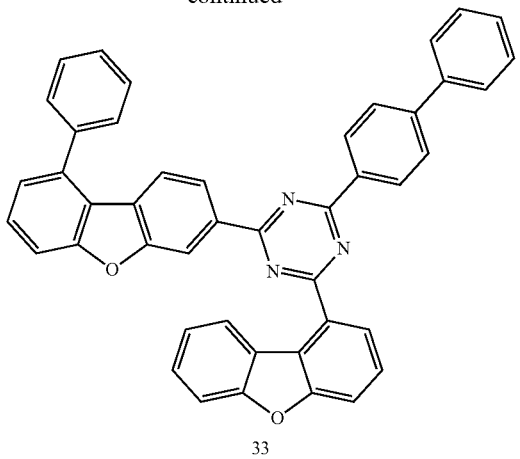

33

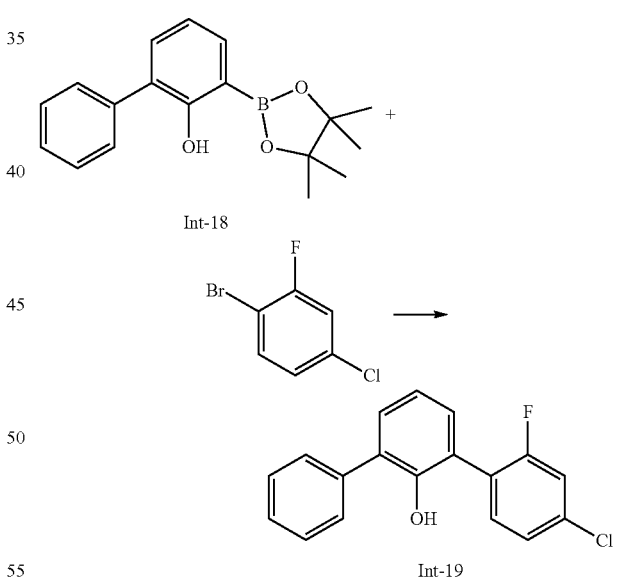

Int-17

Int-18

Intermediate (Int-35) (19.9 g, 39 mmol), Intermediate (Int-33) (11.5 g, 39 mmol), K$_2$CO$_3$ (8.1 g, 58.5 mmol), and Pd(PPh$_3$)$_4$ (2.25 g, 1.95 mmol) were dissolved in distilled water (50 ml) and THF (150 ml) in a round-bottomed flask and stirred under reflux at 60° C. for 12 hours. When a reaction was complete, the resultant was poured into an excessive amount of methanol, and the obtained mixture was stirred for 30 minutes at room temperature. A solid therein was filtered and was recrystallized with dichlorobenzene to obtain 13 g (52%) of Compound 33. LC/MS calculated for: C$_{45}$H$_{27}$N$_3$O$_2$ Exact Mass: 641.21. found for: 642.30.

Intermediate (Int-17) (74 g, 297 mmol), bis(pinacolato)diboron (90.5 g, 356 mmol), Pd(dppf)Cl$_2$ (7.3 g, 8.9 mmol), and potassium acetate (43.7 g, 446 mmol) were dissolved in toluene (1100 ml) in a round-bottomed flask under a nitrogen condition, and the mixed solution was stirred under reflux at 120° C. condition for 15 hours. When a reaction was complete, the resultant was filtered with Celite to remove a solid therefrom, and 1 L of hot toluene was poured thereinto. The filtered solution was removed under a reduced pressure, and was recrystallized with ethyl acetate to obtain 39.6 g (45%) of Intermediate (Int-18).

Comparative Synthesis Example 1: Synthesis of Compound X

[Reaction Scheme]

Int-17

2-phenylphenol (60 g, 352 mmol) and p-toluenesulfonic acid monohydrate (6.7 g, 35 mmol) were put in a round-bottomed flask and dissolved in 400 ml of methanol. On the other hand, NBS (62.7 g, 352 mmol) was dissolved in 1 L of methanol, and the solution was slowly added to the above solution in a dropwise fashion at 0° C. for 30 minutes. The obtained mixture was stirred for 1 hour at room temperature, and when a reaction was complete, a sodium thiosulfate-saturated solution was added thereto, and the obtained mixture was stirred. DCM was added thereto for an extraction, and a solvent was removed therefrom under a reduced pressure. The obtained extract was separated through flash column chromatography to obtain 74 g (84%) of Intermediate (Int-17).

Intermediate (Int-18) (39.6 g, 134 mmol), 1-bromo-4-chloro-2-fluorobenzene (28 g, 134 mmol), K$_2$CO$_3$ (37 g, 267 mmol), and Pd(PPh$_3$)$_4$ (4.6 g, 4 mmol) were dissolved in 180 ml of distilled water and 650 ml of THF in a round-bottomed flask and then, stirred under reflux at 60° C. for 12 hours. When a reaction was complete, the resultant was poured into an excessive amount of methanol, and the obtained mixture was stirred for 30 minutes at room temperature. A solid therein was filtered, dried, and 26 g (65%) of Intermediate (Int-19) was obtained through column chromatography (hexane:DCM (30%)).

[Reaction Scheme]

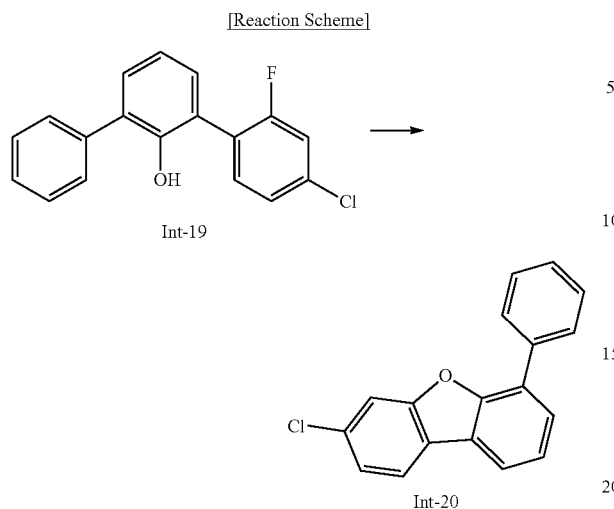

22 g (91%) of Intermediate (Int-20) was obtained according to the same method as Synthesis Example 3 by dissolving intermediate (Int-19) (26 g, 87 mmol), K$_2$CO$_3$ (15.6 g, 113 mmol) in 290 ml of NMP in a round-bottomed flask.

[Reaction Scheme]

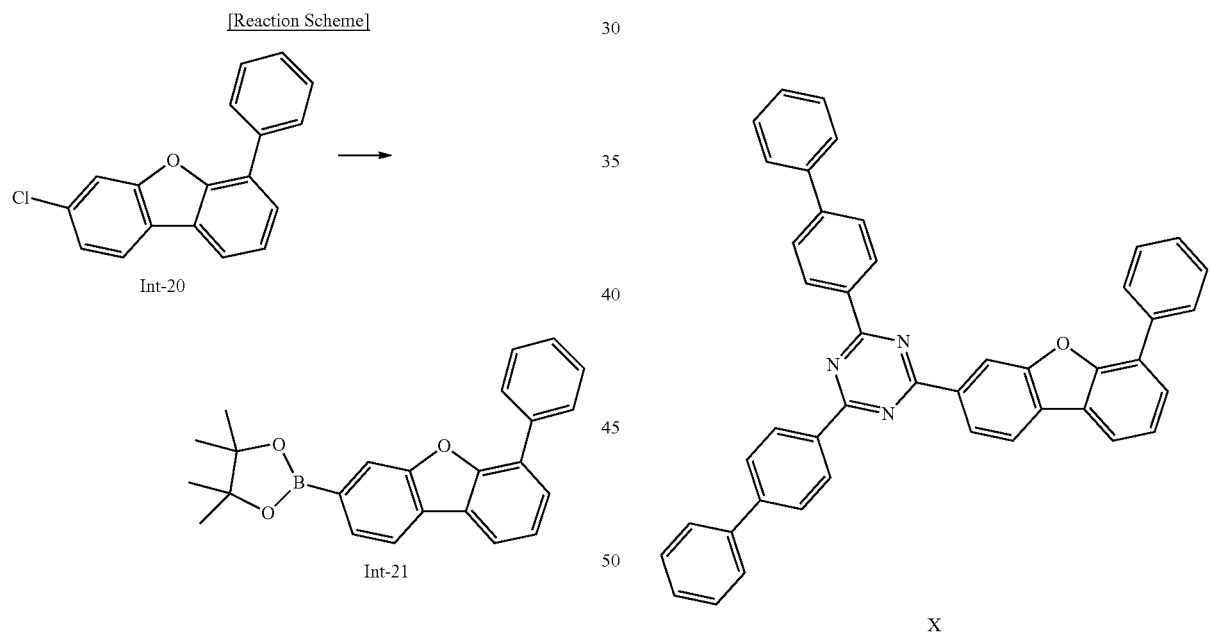

Intermediate (Int-20) (22 g, 79 mmol), bis(pinacolato)diboron (24 g, 95 mmol), Pd(dppf)Cl$_2$ (1.9 g, 2.4 mmol), tricyclohexylphosphine (3.8 g, 15.8 mmol), and potassium acetate (15.5 g, 158 mmol) were dissolved in 310 ml of DMF in a round-bottomed flask. The mixture was stirred under reflux at 120° C. for 12 hours. When a reaction was complete, the resultant was poured into an excessive amount of distilled water, and the obtained mixture was stirred for one hour. A solid therein was filtered and dissolved in DCM. After removing moisture therefrom with MgSO$_4$, an organic solvent was filtered with a silica gel pad and then, removed under a reduced pressure. A solid therefrom was recrystallized by using ethyl acetate and hexane to obtain 23.4 g (80%) of Intermediate (Int-21).

[Reaction Scheme]

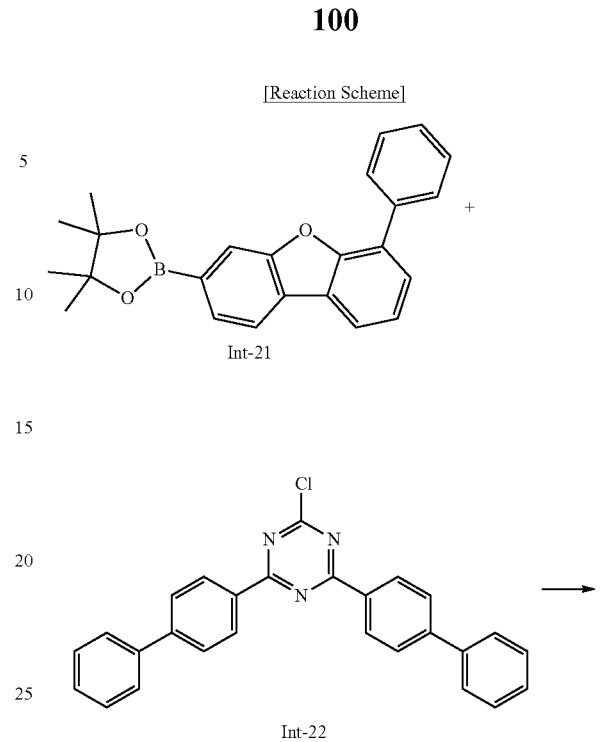

Intermediate (Int-21) (13 g, 35 mmol), Intermediate (Int-22) (14.7 g, 35 mmol), K$_2$CO$_3$ (9.7 g, 70 mmol), and Pd(PPh$_3$)$_4$ (1.2 g, 1 mmol) were dissolved in 50 ml of distilled water and 180 ml of THF and then, stirred under reflux at 60° C. for 12 hours. When a reaction was complete, the resultant was poured into an excessive amount of methanol, and the obtained mixture was stirred for 30 minutes at room temperature. A solid therein was filtered and vacuum-dried. The solid was recrystallized with monochlorobenzene to obtain 12.1 g (55%) of Compound X.

LC/MS calculated for: C$_{45}$H$_{29}$N$_3$O Exact Mass: 627.23. found for: 628.11.

Comparative Synthesis Example 2: Synthesis of Compound Y

[Reaction Scheme]

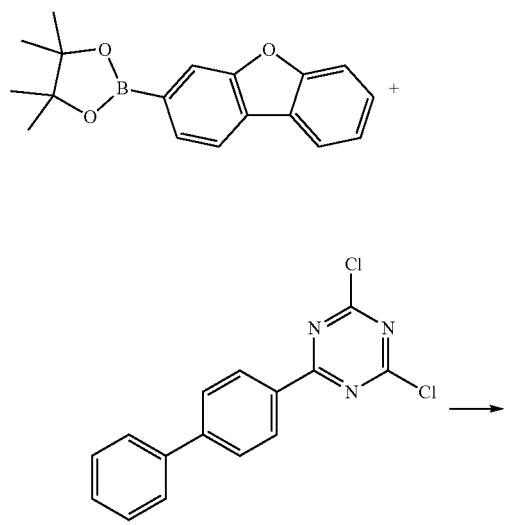

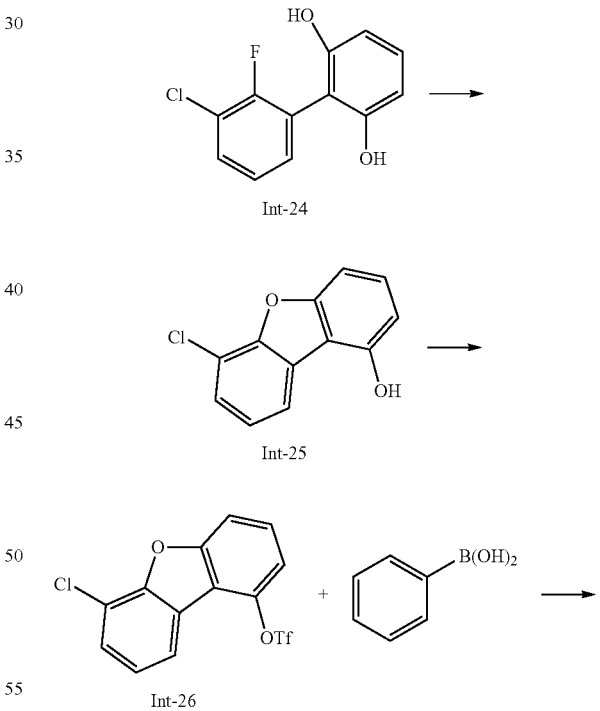

Y 2,4-bis(4-biphenylyl)-6-chloro-1,3,5-triazine (11 g, 36.4 mmol), 3-(4,4,5,5-tetramethyl-1,3,2-dioxaborolan-2-yl)-dibenzofuran (23.6 g, 80.1 mmol) $K_2CO_3$ (11.1 g, 80.1 mmol), and $Pd(PPh_3)_4$ (2.1 g, 1.8 mmol) were dissolved in 60 ml of distilled water and 190 ml of THF in a round-bottomed flask under a nitrogen condition and then stirred under reflux at 60° C. for 12 hours. When a reaction was complete, the resultant was poured into an excessive amount of methanol, and the obtained mixture was stirred for 30 minutes at room temperature. A solid therein was filtered and vacuum-dried. The solid was recrystallized by using mono-chlorobenzene to obtain 14.4 g (70%) of Compound Y.

LC/MS calculated for: $C_{39}H_{23}N_3O_2$ Exact Mass: 565.18. found for: 566.01.

Comparative Synthesis Example 3: Synthesis of Compound Z

[Reaction Scheme]

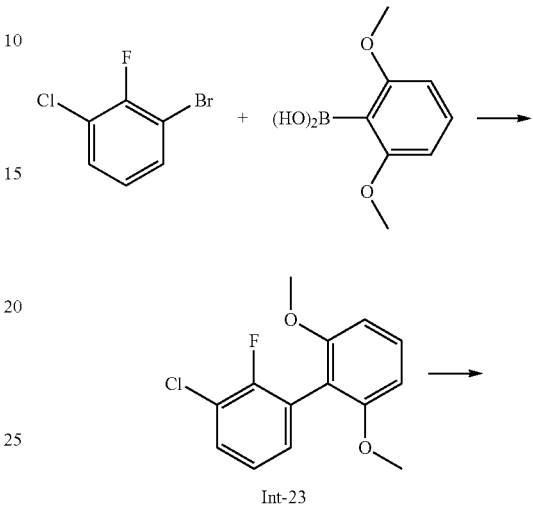

Int-23

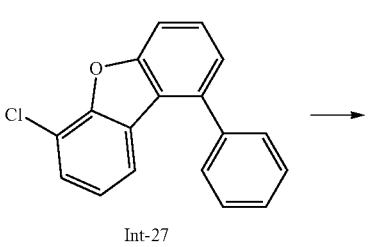

Int-24

Int-25

Int-26

Int-27

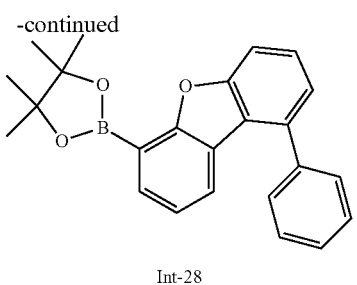

Int-28

13.3 g (15%) of each of Intermediates (Int-23 to Int-28) were obtained according to the same method as Synthesis Example 1 to Synthesis Example 6 by using 1-bromo-3-chloro-2-fluorobenzene (50 g, 239 mmol) instead of 1-bromo-4-chloro-2-fluorobenzene.

[Reaction Scheme]

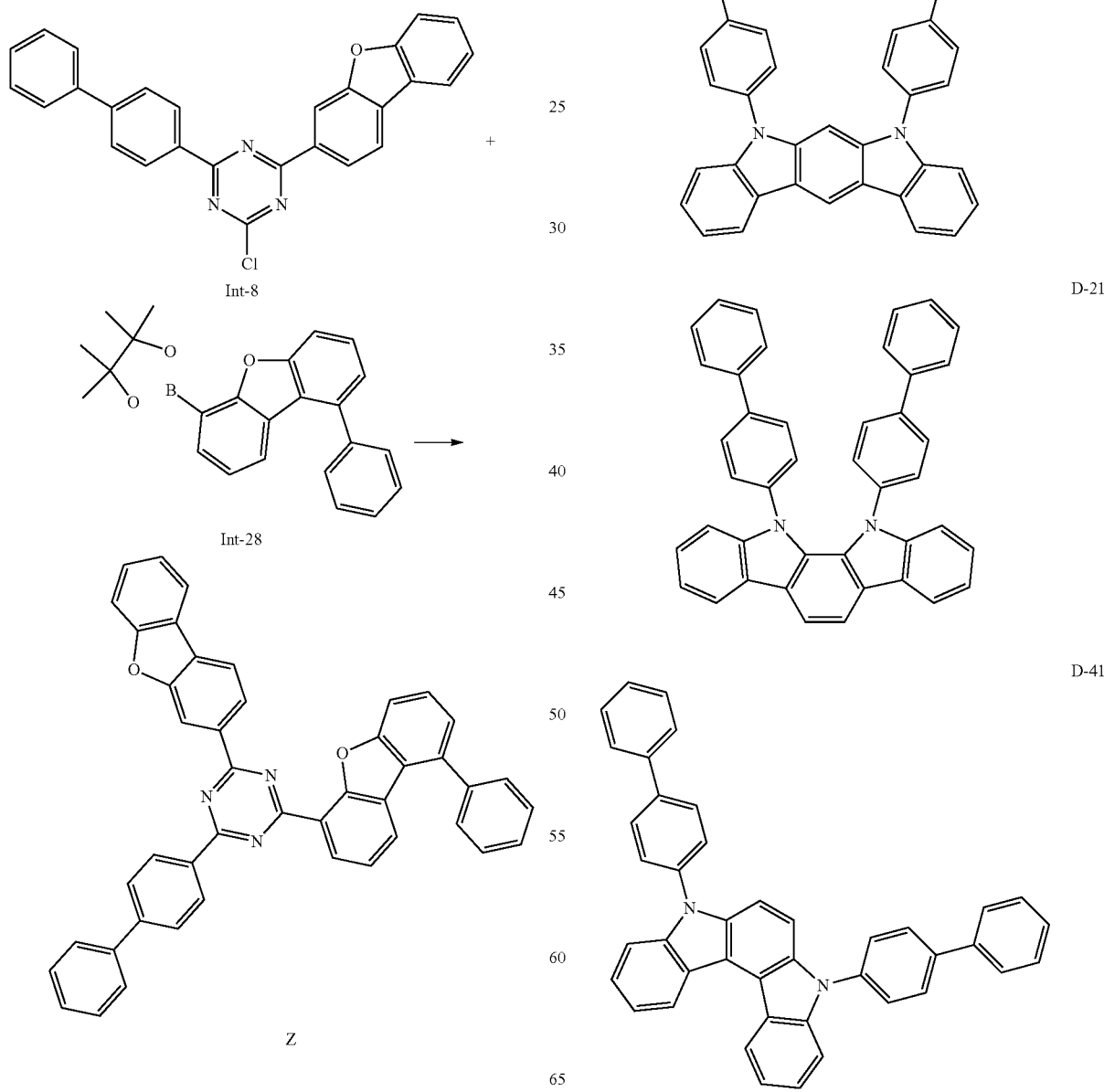

Intermediate (Int-8) (15.6 g, 36 mmol), Intermediate (Int-28) (13.3 g, 36 mmol), $K_2CO_3$ (7.5 g, 54 mmol), and Pd(PPh$_3$)$_4$ (1.3 g, 1.1 mmol) were dissolved in 50 ml of distilled water and 200 ml of THF in a round-bottomed flask under a nitrogen condition and then, stirred under reflux at 60° C. condition for 12 hours. When a reaction was complete, the resultant was poured into an excessive amount of methanol, and the obtained mixture was stirred for 30 minutes at room temperature. A solid therein was filtered and vacuum-dried. The solid was recrystallized with monochlorobenzene to obtain 13.2 g (57%) of Compound Z.

LC/MS calculated for: $C_{45}H_{27}N_3O_2$ Exact Mass: 641.21. found for: 642.05.

(Preparation of Second Host)

Synthesis Example 21: Synthesis of Compound D-1

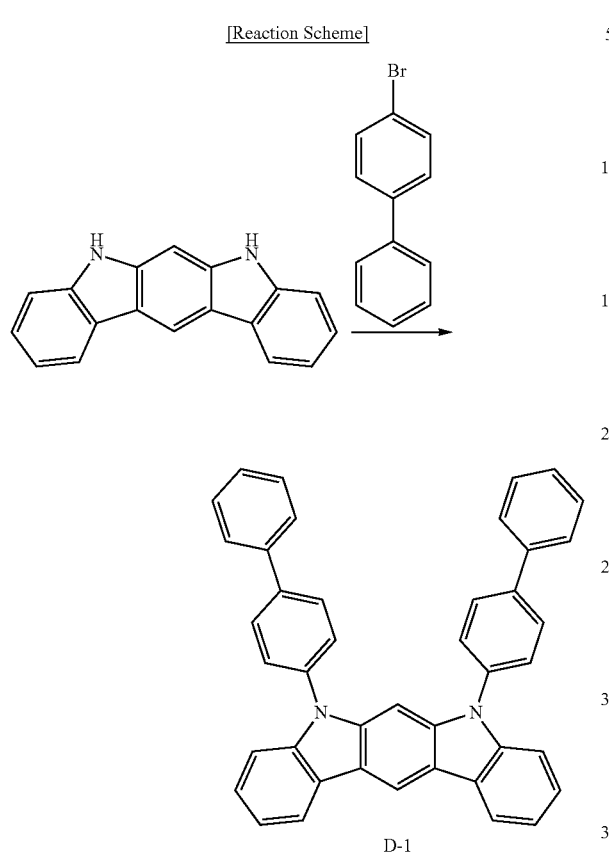

Compound D-1 was synthesized according to the same method as Synthesis Example 3 by using 1 equivalent of the synthesized intermediate of 5,7-dihydro-indolo[2,3-b]carbazole (cas: 111296-90-3) and 2.5 equivalent of 4-bromo-1,1'-biphenyl (cas: 92-66-0).

LC/MS calculated for: $C_{42}H_{28}N_2$ Exact Mass: 560.2252. found for: 561.24.

Synthesis Example 22 and Synthesis Example 23: Synthesis of Compound D-21 and Compound D-41

Compound D-21 and Compound D-41 were respectively synthesized according to the same method as the method of synthesizing Compound D-1 of Synthesis Example 21 by using each intermediate of 11,12-dihydro-indolo[2,3-a]carbazole (cas: 60511-85-5) and 5,8-dihydro-indolo[2,3-c]carbazole (cas: 200339-30-6).

(Preparation of Phosphorescent Dopant)

Synthesis Example 24: Synthesis of Compound E-24

Compound E-24 as a dopant was synthesized according to the same reaction as the method of preparing Compound II-1 in US2014-0131676 except that an indium complex described in [Reaction Scheme] was used as a starting material.

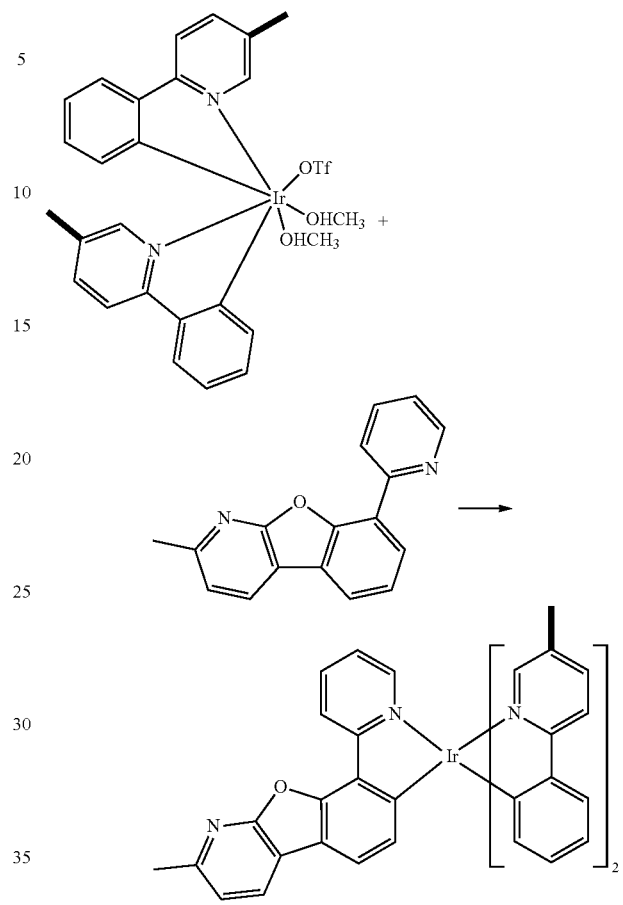

(Manufacture of Organic Light Emitting Diode)

Example 1

A glass substrate coated with ITO (indium tin oxide) as a 1500 Å-thick thin film was ultrasonic wave-washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, a 700 Å-thick hole injection layer was formed on the ITO substrate by vacuum depositing Compound A, and a hole transport layer was formed on the injection layer by depositing Compound B to be 50 Å thick and Compound C to be 1020 Å thick. On the hole transport layer, a 400 Å-thick light emitting layer was formed by vacuum-depositing Compound 12 as a host and being doped with 10 wt % of E-24 as a phosphorescent dopant. Herein, Compound 12 and Compound D-1 were used in a weight ratio of 4:6 and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a multi-layered organic thin layer structure as follows:

a structure of ITO/Compound A (700 Å)/Compound B (50 Å)/Compound C (1020 Å)/EML[Compound 12: Compound E-24 (10 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone

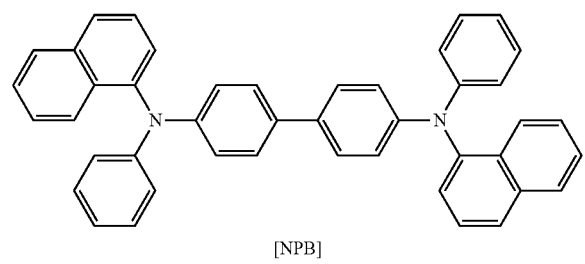

[NPB]

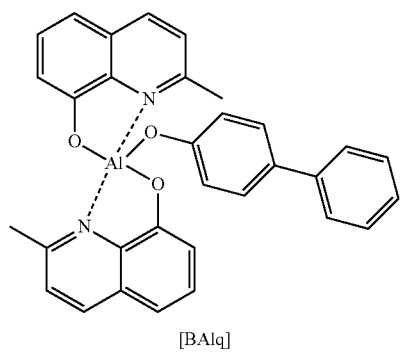

[BAlq]

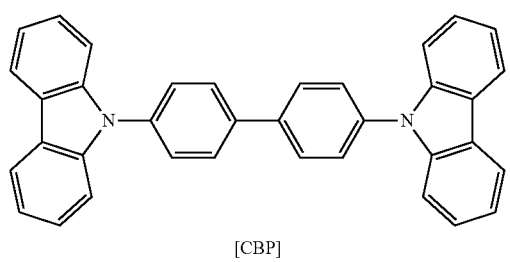

[CBP]

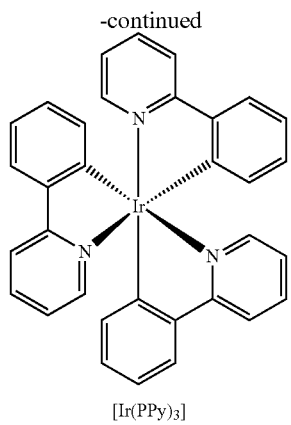

[Ir(PPy)$_3$]

Example 2 to Example 11 and Comparative Example 1 to Comparative Example 7

Organic light emitting diodes were respectively manufactured according to the same method as Example 1, except that compositions of the first host, the second host and the phosphorescent dopant were changed as described in Table 1.

Evaluation 1: Synergic Effect of Luminous Efficiency and Life-Span

Luminous efficiency and life-span characteristics of the organic light emitting diodes according to Example 1 to Example 11 and Comparative Example 1 to Comparative Example 7 were evaluated. Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T95 life-spans of the organic light emitting diodes according to Example 1 to Example 11 and Comparative Example 1 to Comparative Example 7 were measured as a time when their luminance decreased down to 95% relative to the initial luminance after emitting light with 5000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$.

TABLE 1

| | First host | Second host | Ratio of first and second hosts | Dopant | Color | Efficiency Cd/A | Life-span T95 | Driving (Vd) |
|---|---|---|---|---|---|---|---|---|
| Example 1 | Compound 12 | — | alone | E-24 | green | 51 | 22 | 4.4 |
| Example 2 | Compound 16 | — | alone | E-24 | green | 53 | 25 | 4.6 |
| Example 3 | Compound 9 | D-21 | 4:6 | E-24 | green | 65 | 137 | 4.2 |
| Example 4 | Compound 9 | D-41 | 4:6 | E-24 | green | 61 | 133 | 4.0 |
| Example 5 | Compound 12 | D-21 | 4:6 | E-24 | green | 63 | 136 | 4 |
| Example 6 | Compound 16 | D-21 | 4:6 | E-24 | green | 62 | 135 | 4.1 |
| Example 7 | Compound 12 | D-41 | 4:6 | E-24 | green | 68 | 140 | 4 |
| Example 8 | Compound 16 | D-41 | 4:6 | E-24 | green | 66 | 142 | 3.9 |
| Example 9 | Compound 33 | — | alone | E-24 | green | 56 | 30 | 4.2 |
| Example 10 | Compound 33 | D-21 | 4:6 | E-24 | green | 68 | 155 | 3.9 |
| Example 11 | Compound 33 | D-41 | 4:6 | E-24 | green | 66 | 158 | 3.8 |
| Comparative Example 1 | Compound X | — | alone | E-24 | green | 34 | 26 | 5.1 |
| Comparative Example 2 | Compound X | D-41 | 4:6 | E-24 | green | 55 | 118 | 4.8 |
| Comparative Example 3 | Compound Y | — | alone | E-24 | green | 39 | 15 | 5.2 |
| Comparative Example 4 | Compound Y | D-41 | 4:6 | E-24 | green | 56 | 82 | 4.7 |
| Comparative Example 5 | Compound Z | — | alone | E-24 | green | 40 | 17 | 5.5 |
| Comparative Example 6 | Compound Z | D-41 | 4:6 | E-24 | green | 56 | 95 | 5.1 |
| Comparative Example 7 | Compound Z | D-41 | 4:6 | Ir(ppy)$_3$ | green | 49 | 90 | 5.6 |

Referring to Table 1, the organic light emitting diodes using a compound represented by Chemical Formula 1 as a host or a compound represented by Chemical Formula 1 as a first host and indolocarbazole as a second host showed a large advantage in terms of driving and efficiency compared with the organic light emitting diodes using a compound not represented by Chemical Formula 1 as a first host alone or another compound as a second host. In addition, the organic light emitting diode using Compound E-24 of a phosphorescent dopant including a dibenzofuran group showed a large advantage in terms of efficiency compared with the organic light emitting diode using Ir(ppy)$_3$ of a phosphorescent dopant including no dibenzofuran group. In particular, the compound having a structure substituted with an aryl group at a No. 1 position (refer to FIG. 3.) of dibenzofuran as a first host showed an effect of additionally decreasing a driving voltage and increasing a life-span.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic diode represented by Chemical Formula 1:

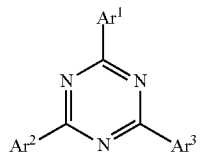

[Chemical Formula 1]

wherein, in Chemical Formula 1,

Ar$^1$ is an unsubstituted biphenyl group or an unsubstituted terphenyl group,

Ar$^2$ is represented by one of Chemical Formula 2A, Chemical Formula 3A, and Chemical Formula 4A, and Ar$^3$ is represented by Chemical Formula 2B or Chemical Formula 4B,

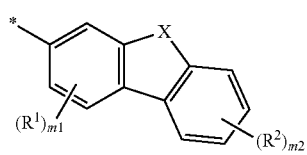

[Chemical Formula 2A]

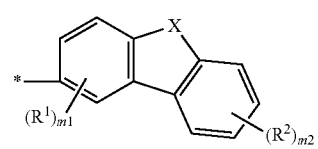

[Chemical Formula 3A]

[Chemical Formula 4A]

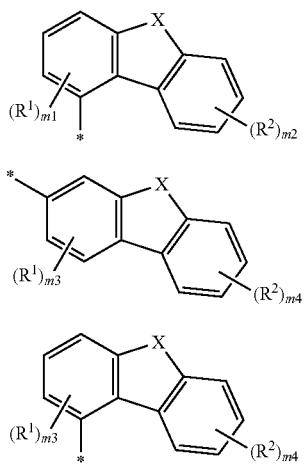

[Chemical Formula 2B]

[Chemical Formula 4B]

wherein, in Chemical Formula 2A, Chemical Formula 3A, Chemical Formula 4A, Chemical Formula 2B and Chemical Formula 4B, X is O, $R^1$ and $R^2$ are independently an unsubstituted phenyl group, $R^1$ is bonded to the moiety that includes X at the 1 or 4 position, $R^2$ is bonded to the moiety that includes X at the 9 position, m1 and m2 are each 0, m3 and m4 are each independently 0 or 1, and m1+m2+m3+m4=1, and

* is a linking point.

2. The compound for the organic optoelectronic diode of claim 1, wherein $Ar^2$ is represented by Chemical Formula 2-3, Chemical Formula 3-3, or Chemical Formula 4-2 and $Ar^3$ is represented by Chemical Formula 2-1, Chemical Formula 2-2, or Chemical Formula 4-1:

[Chemical Formula 2-1]

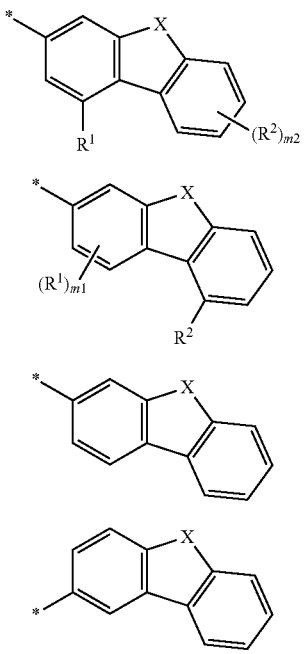

[Chemical Formula 2-2]

[Chemical Formula 2-3]

[Chemical Formula 3-3]

[Chemical Formula 4-1]

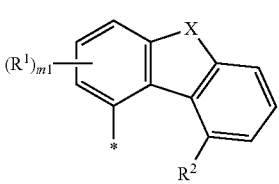

[Chemical Formula 4-2]

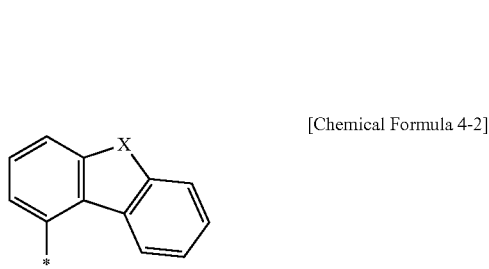

wherein, in Chemical Formula 2-1, Chemical Formula 2-2, Chemical Formula 2-3, Chemical Formula 3-3, Chemical Formula 4-1, and Chemical Formula 4-2, X is O, $R^1$ and $R^2$ are independently an unsubstituted phenyl group, m1 and m2 are each 0, and

* is a linking point.

3. The compound for the organic optoelectronic diode of claim 1, wherein the compound for an organic optoelectronic diode represented by Chemical Formula 1 is selected from compounds of Group 1:

9

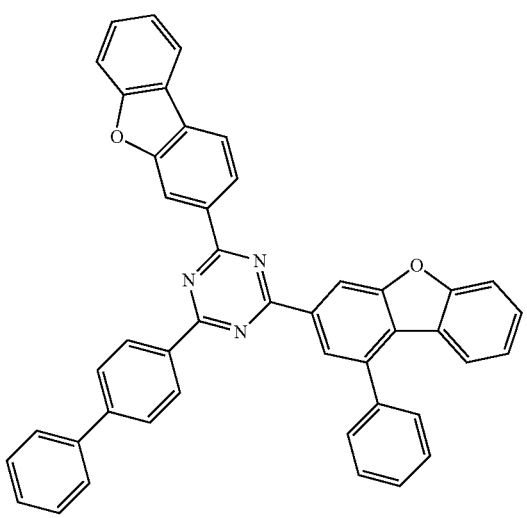

12
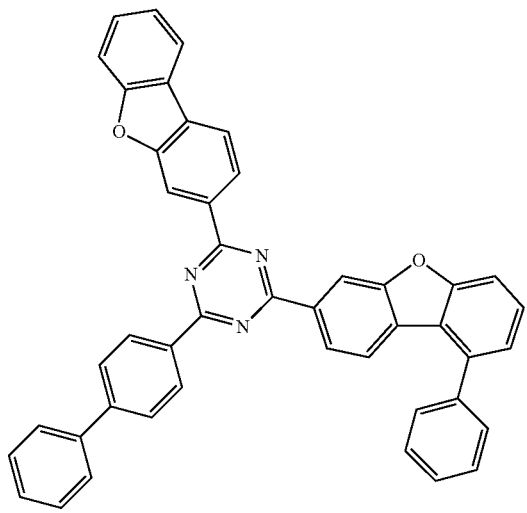
13
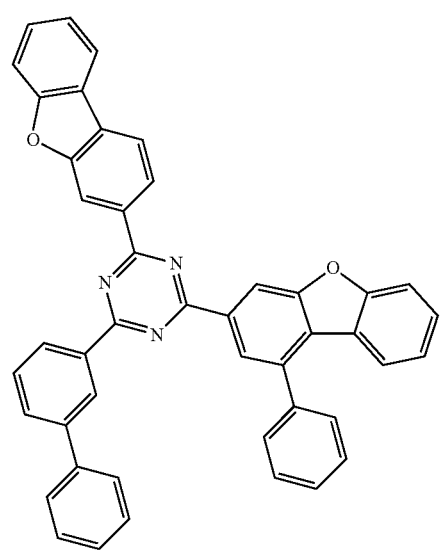
16
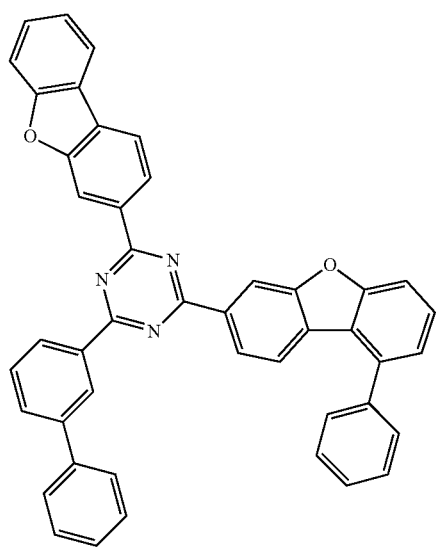
27
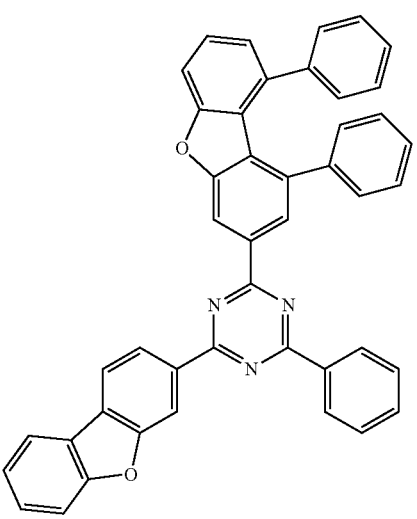
33
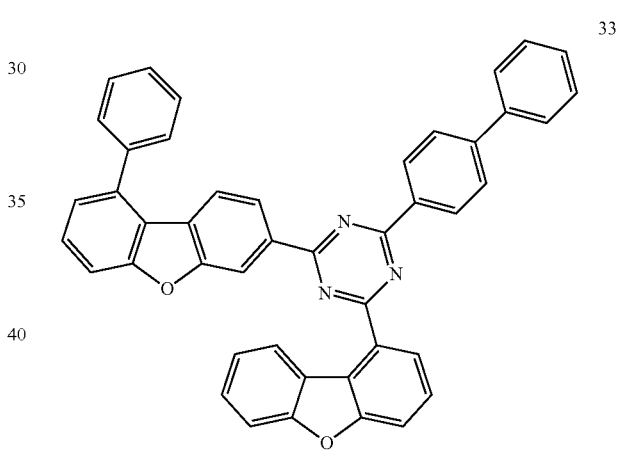
36
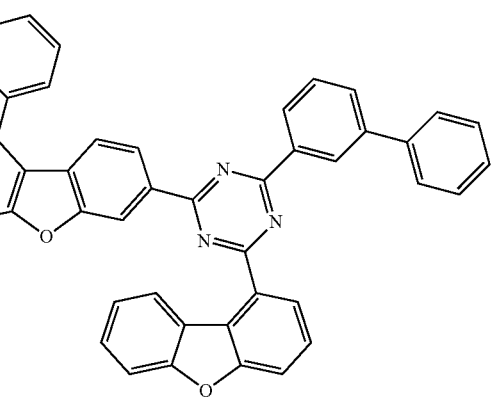

-continued

41

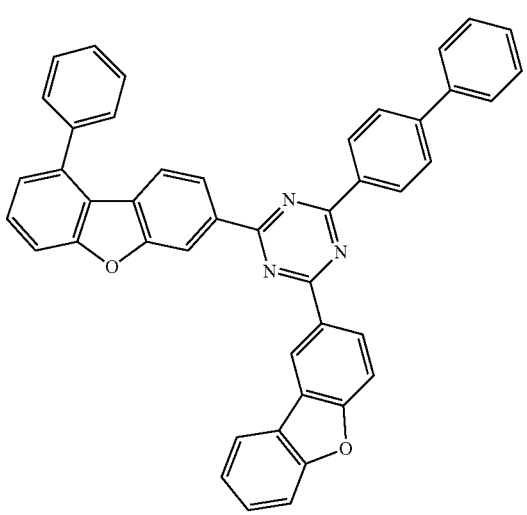

44

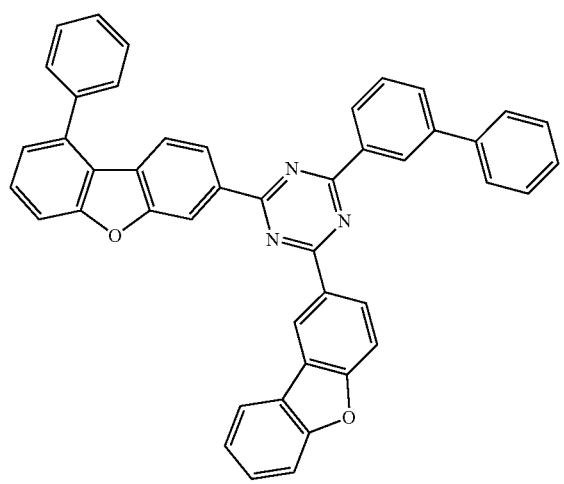

54

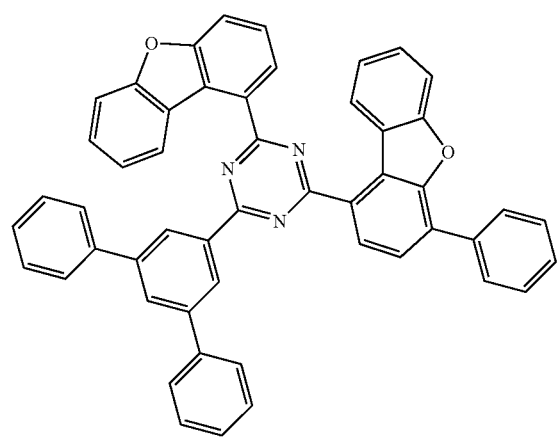

-continued

56

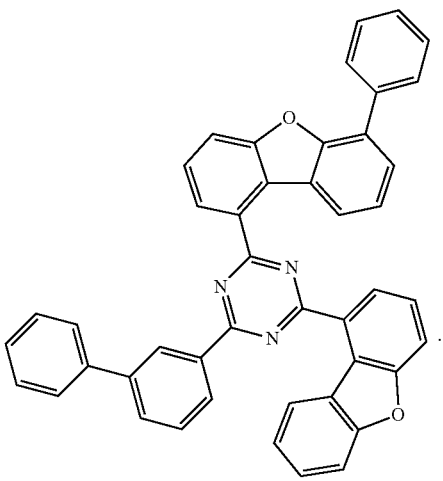

4. A composition for an organic optoelectronic diode comprising the compound of claim 1.

5. An organic optoelectronic diode, comprising
an anode and a cathode facing each other, and
an organic layer disposed between the anode and the cathode,
wherein the organic layer comprises at least one of a hole injection layer, a hole transport layer, a light emitting layer, and an electron transport layer, and
the light emitting layer comprises the composition for an organic optoelectronic diode of claim 4 as a first host.

6. The organic optoelectronic diode of claim 5, wherein the light emitting layer further comprises a compound represented by a combination of Chemical Formula 6 and Chemical Formula 7 as a second host:

[Chemical Formula 6]

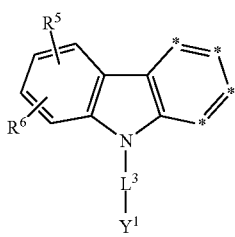

[Chemical Formula 7]

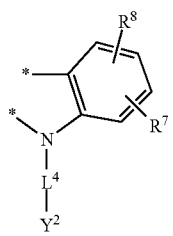

wherein, in Chemical Formula 6 to Chemical Formula 7,
$Y^1$ and $Y^2$ are independently a substituted or unsubstituted C6 to C20 aryl group, or a substituted or unsubstituted C2 to C30 heterocyclic group,
adjacent two *'s of Chemical Formula 6 are linked to Chemical Formula 7,
*'s of Chemical Formula 6 not linked to Chemical Formula 7 is independently C-$L^a$-$R^b$,
$L^a$, $L^3$, and $L^4$ are independently a single bond, or a substituted or unsubstituted C6 to C20 arylene group, and $R^b$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

7. The organic optoelectronic diode of claim 6, wherein the compound represented by the combination of Chemical Formula 6 and Chemical Formula 7 is represented by one of Chemical Formula 6A, Chemical Formula 6B, Chemical Formula 6C, and Chemical Formula 6D:

[Chemical Formula 6A]

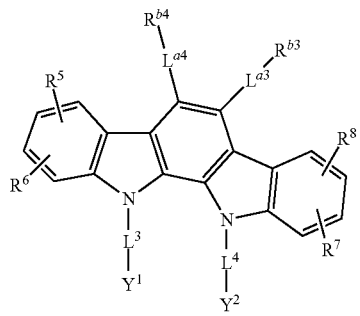

[Chemical Formula 6B]

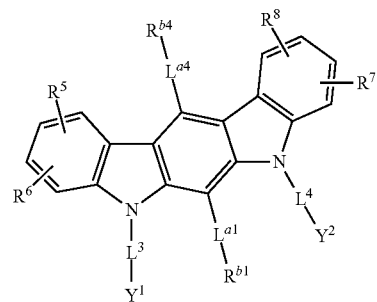

[Chemical Formula 6C]

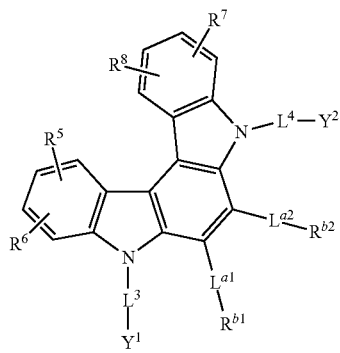

[Chemical Formula 6D]

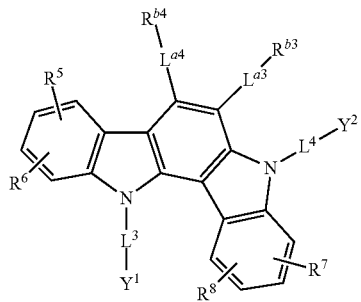

wherein, in Chemical Formula 6A to Chemical Formula 6D, $Y^1$ and $Y^2$ are independently a substituted or unsubstituted C6 to C20 aryl group, or a substituted or unsubstituted C2 to C30 heterocyclic group, $L^{a1}$ to $L^{a4}$, $L^3$, and $L^4$ are independently a single bond, or a substituted or unsubstituted C6 to C20 arylene group, and $R^{b1}$ to $R^{b4}$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

8. The organic optoelectronic diode of claim 7, wherein $Y^1$ and $Y^2$ are independently a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, and $R^{b1}$ to $R^{b4}$ and $R^5$ to $R^8$ are independently hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group.

9. The organic optoelectronic diode of claim 5, wherein the organic optoelectronic diode further comprises a phosphorescent dopant represented by Chemical Formula 8:

[Chemical Formula 8]

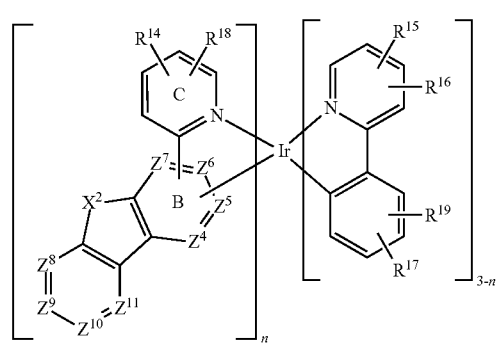

wherein, in Chemical Formula 8, $Z^4$ to $Z^{11}$ are independently N, C or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is one of integers of 1 to 3.

10. The organic optoelectronic diode of claim 9, wherein Chemical Formula 8 is represented by one of Chemical Formula 8-1 to Chemical Formula 8-6:

[Chemical Formula 8-1]

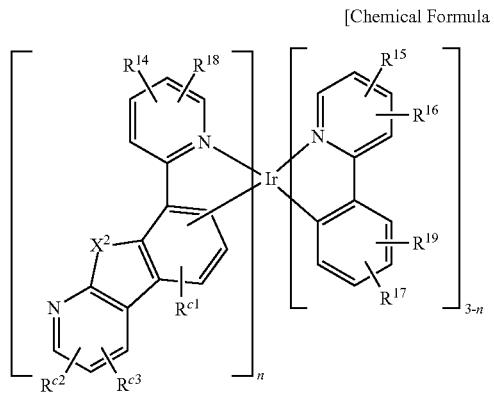

[Chemical Formula 8-2]

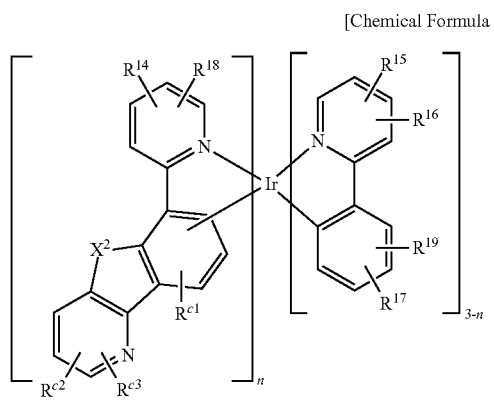

[Chemical Formula 8-3]

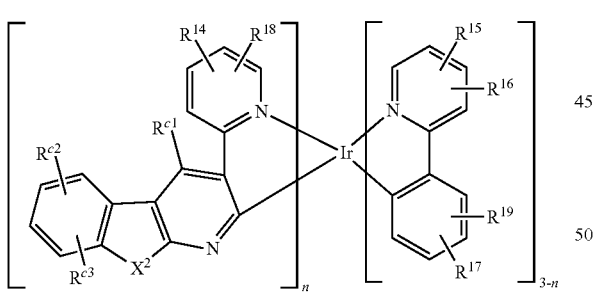

[Chemical Formula 8-4]

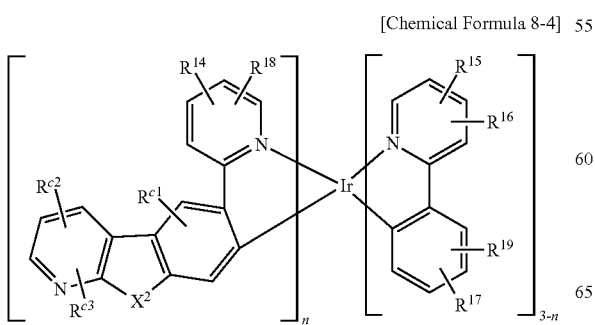

-continued

[Chemical Formula 8-5]

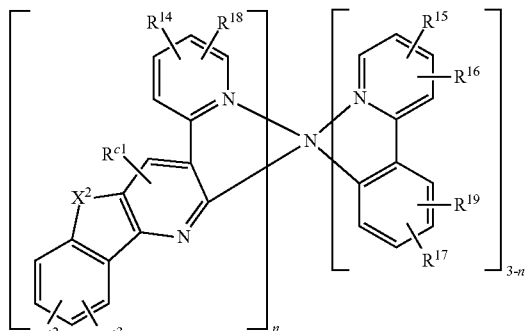

[Chemical Formula 8-6]

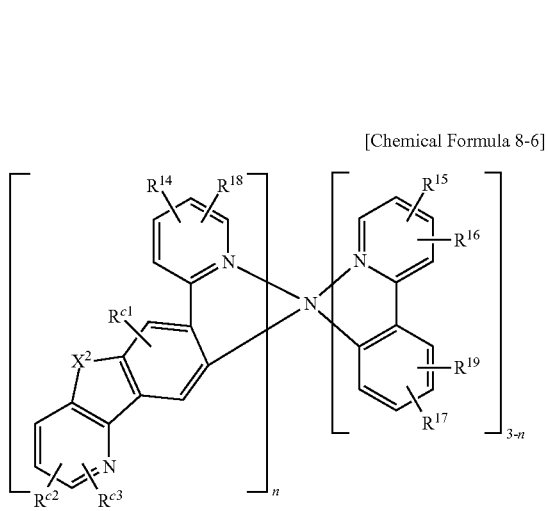

wherein, in Chemical Formula 4-1 to Chemical Formula 4-6, $X^2$ is O or S, $R^{c1}$, $R^{c2}$, $R^{c3}$, and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is one of integers of 1 to 3.

11. A display device comprising the organic optoelectronic diode of claim 5.

12. The organic optoelectronic diode of claim 6, wherein, in Chemical Formula 6 and Chemical Formula 7, moiety -$L^3$-$Y^1$ and moiety -$L^4$-$Y^2$ do not include a terphenyl group.

13. The organic optoelectronic diode of claim 6, wherein the compound represented by the combination of Chemical Formula 6 and Chemical Formula 7 is represented by Chemical Formula 6A or Chemical Formula 6B:

[Chemical Formula 6A]

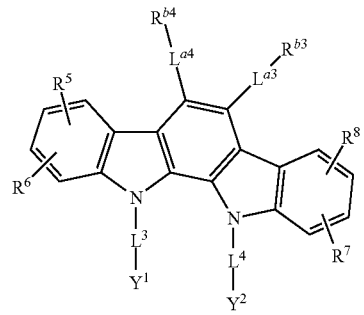

[Chemical Formula 6B]

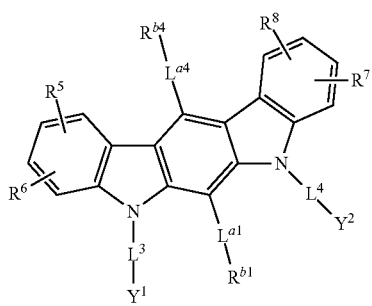

wherein, in Chemical Formula 6A and Chemical Formula 6B, $Y^1$ and $Y^2$ are independently a substituted or unsubstituted C6 to C20 aryl group, or a substituted or unsubstituted C2 to C30 heterocyclic group, $L^{a1}$, $L^{a3}$, $L^{a4}$, $L^3$, and $L^4$ are independently a single bond, or a substituted or unsubstituted C6 to C20 arylene group, and $R^{b1}$, $R^{b3}$, $R^{b4}$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group.

14. The compound for the organic optoelectronic diode of claim 1, wherein the compound for an organic optoelectronic diode represented by Chemical Formula 1 is selected from compounds of Group 2:

[Group 2]

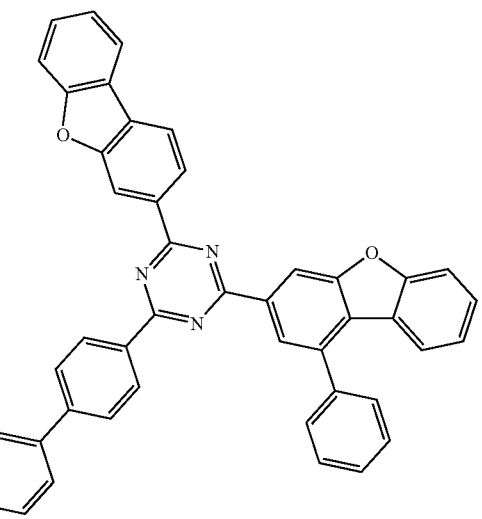

9

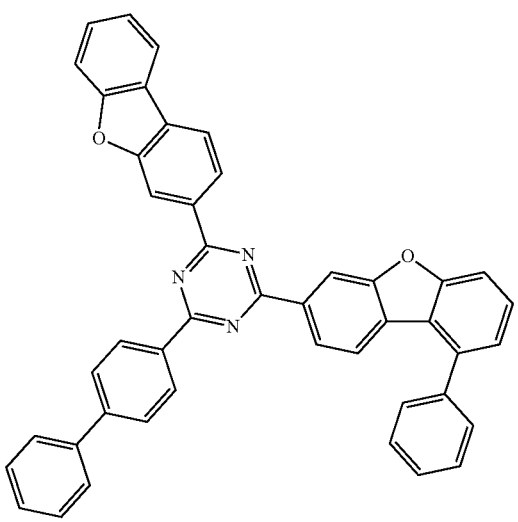

12

123
-continued
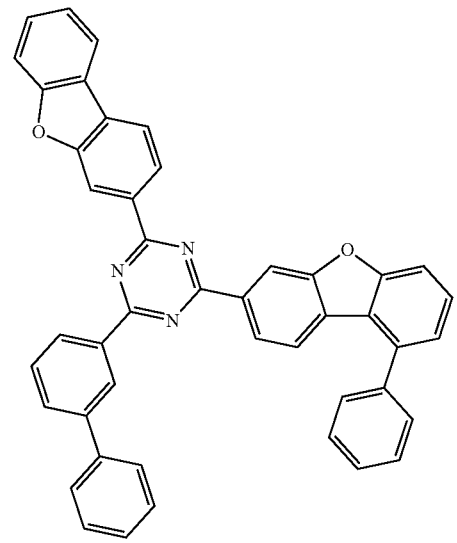
124
-continued
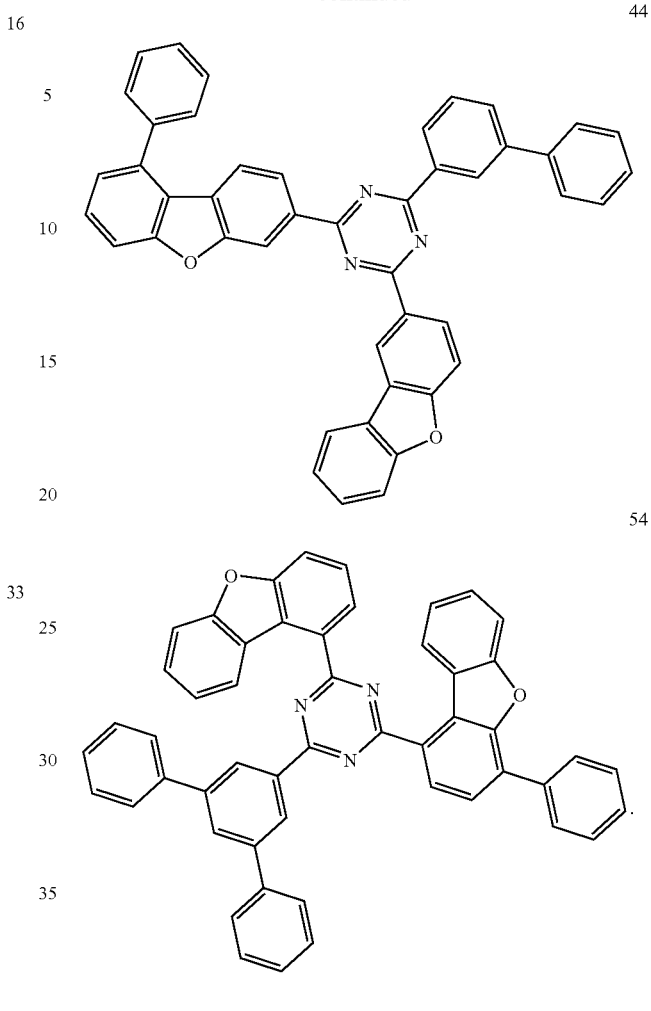
* * * * *